(12) United States Patent
Shaw

(10) Patent No.: US 9,096,843 B2
(45) Date of Patent: Aug. 4, 2015

(54) PEPTIDYL α-HYDROXYGLYCINE α-AMIDATING LYASES

(75) Inventor: Allan C. Shaw, Koebenhavn (DK)

(73) Assignee: Novo Nordisk A/S, Bagsvaerd (DK)

( * ) Notice: Subject to any disclaimer, the term of this patent is extended or adjusted under 35 U.S.C. 154(b) by 380 days.

(21) Appl. No.: 13/513,049

(22) PCT Filed: Dec. 1, 2010

(86) PCT No.: PCT/EP2010/068630
§ 371 (c)(1),
(2), (4) Date: Aug. 8, 2012

(87) PCT Pub. No.: WO2011/067283
PCT Pub. Date: Jun. 9, 2011

(65) Prior Publication Data
US 2012/0322733 A1    Dec. 20, 2012

Related U.S. Application Data

(60) Provisional application No. 61/266,711, filed on Dec. 4, 2009.

(30) Foreign Application Priority Data

Dec. 1, 2009    (EP) .................................... 09177593

(51) Int. Cl.
*C12P 21/06* (2006.01)
*C12N 15/09* (2006.01)
*C12P 21/04* (2006.01)
*C12P 39/00* (2006.01)
*C12N 9/88* (2006.01)

(52) U.S. Cl.
CPC ........................................ *C12N 9/88* (2013.01)
USPC .......... 435/68.1; 435/42; 435/69.1; 435/69.4; 435/71.1; 435/71.2

(58) Field of Classification Search
None
See application file for complete search history.

(56) References Cited

U.S. PATENT DOCUMENTS

| 4,708,934 | A | 11/1987 | Gilligan et al. |
| 5,124,314 | A | 6/1992 | Cooper |
| 5,196,316 | A | 3/1993 | Iwasaki et al. |
| 5,789,234 | A | 8/1998 | Bertelsen et al. |
| 2003/0153488 | A1 | 8/2003 | May et al. |
| 2006/0292672 | A1 | 12/2006 | Miller et al. |

FOREIGN PATENT DOCUMENTS

| CN | 101287840 | A | 10/2008 |
| EP | 382403 | A2 | 8/1990 |
| EP | 404967 | A1 | 1/1991 |
| EP | 448513 | A2 | 9/1991 |
| EP | 465404 | A2 | 1/1992 |
| EP | 2172550 | A1 | 4/2010 |
| WO | 89/02460 | A1 | 3/1989 |
| WO | 90/08194 | A1 | 7/1990 |
| WO | 01/49856 | A2 | 7/2001 |
| WO | 0248192 | A2 | 6/2002 |
| WO | 2005014031 | A1 | 2/2005 |

OTHER PUBLICATIONS

Mizuno et al. (Biochemical and Biophysical Research Communications, vol. 148, Issue 2, Oct. 29, 1987, pp. 546-552).*
Liu S J et al. Function and Structure of Peptide a—Amidating Monooxygenase. Progress in Biochemistry and Biophysics. 1999. vol. 23(3). pp. 196-197.
Kim and Seong "Peptide Amidation: Production of Peptide Hormones in vivo and in vitro" Biotechnol. Bioprocess Eng. vol. 6(4): 244-251 (2001).
Database Uniprot, 2007; EBI; UniProt:A5PDW5.
Database Uniprot; 2007 EBI; UniProt:A6C4A8.
Database Uniprot; 2008; EBI; UniProt:B4CYT3.
Database Uniprot; 2009; EBI; UniProt:C4L4B8.
Tebo, B. et al., Accession; ABCG01000008 Region: 123817.124812 (gi:148829554) Definition: Erythrobacter sp. SD-21 1101482001797, whole aenome shotgun sequence. NCBI Entrez Nucleotide (online). Jun. 14, 2007 uploaded, NCBI, retrieved on Dec. 15, 2014, Retrieved from the Internet, URL, http://www.nebi.nlm.nih.gov/nuccore/abcg01000008.
Tebo, B. et al., "Accession: A5PDW5, entry version 8" UniProt (online) Jan. 20, 2009 uploaded, UniProt Consortium, retrieved on Dec. 15, 2014 Retrieved from the Internet, URL, http://www.uniprot.org/uniprot/A5PDW5.txt? version=8.
Peptidyl-glycine alpha-amidating monooxygenase (IPR000720), InterPro online; EMBL-EBI, retrieved on Dec. 16, 2014, Retrieved from the Internet, URL, http://www.ebi.ac.uk/interpro/entry/IPR000720.
Satani M, Expression and characterization of human bifunctional peptidylglycine alpha-amidating rnonooxygenase, Journal :Protein expression and purification, Year 2003 Apr., vol. 28, No. 2, pp. 293-302.
Lucas, S. et al., "CP001615 Region: 2523328..2524416 gi:229467163, Definition: Exiguobacterium sp, AT1b, complete genome.", NCBI Entrez Nucleotide online Nov. 24, 2009 uploaded, NCBI, (retrieved on Dec. 15, 2014), Retrieved from the Internet, URL, http://wwvv.ncbi.nim.nih.gov/nuccore/229467163?sat=13?satkey= 9082805.
Lucas, S. et al., "Accession; C4L4B8, entry version 4" UniProt online; Sep. 22, 2009 uploaded, UniProt Consortium, (retrieved on Dec. 15, 2014), Retrieved from the Internet, URL, http://www.uniprot.org/uniprot/C4L4B8.txt?version=4.

(Continued)

*Primary Examiner* — Suzanne M Noakes
*Assistant Examiner* — Jae W Lee
(74) *Attorney, Agent, or Firm* — Nonna G. Akopyan

(57) ABSTRACT

The present patent application concerns an enzyme capable of catalysing the conversion of a α-hydroxyglycine to an α-amide and the use of such enzymes for producing a C-terminal α-amidated peptide.

5 Claims, 21 Drawing Sheets

(56) References Cited

OTHER PUBLICATIONS

Kant, R. et al. ABVL01000004 Region: 261629..262591gi:196225940, Definition: Chthoniobacter flavus Ellin428 ctg76, whole genome shotgun sequence. NCBI Entrez Nucleotide online; Aug. 15, 2008 uploaded, NCBI, [retrieved on Dec. 15, 2014], Retrieved from the Internet, URL, http://www.ncbi.nlm.nih.gov/nuccore/abv101000004.

Lucas, S. et al., "Accession: B4CYT3, entry version 3" UniProt (online); Feb. 10, 2009 uploaded, UniProt Consortium, retrieved on Dec. 15, 2014, Retrieved from the Internet, URL, http://www.uniprot.org/uniprot/B4CYT3.txt?version=3.

Amann, R. et al., "ABCE0100009 Region: 23582..24493 gi;148845981, Definition: Planctornyces maris DSM 8797 1101493009176, whole genome shotgun sequence.", NCBI Entrez Nucleotide [online]; Jun. 15, 2007 uploaded, NCBI, retrieved on Dec. 15, 2014, Retrieved from the Internet.

Amann, R. et al., Accession: A6C4A8, entry version 6 UniProt online Jan. 20, 2009 uploaded, UniProt Consortium, retrieved on Dec. 15, 2014, Retrieved from the Internet, URL, http://www.uniprot.org/uniprot/A6C4A8.tx?version=6.

Nielsen H. et al. Identification of prokaryotic and eukaryotic signal peptides and prediction of their cleavage sites, Journal: Protein Engineering Year 1997, vol. 10) issue1, pp. 1-6.

\* cited by examiner

Fig. 3
A
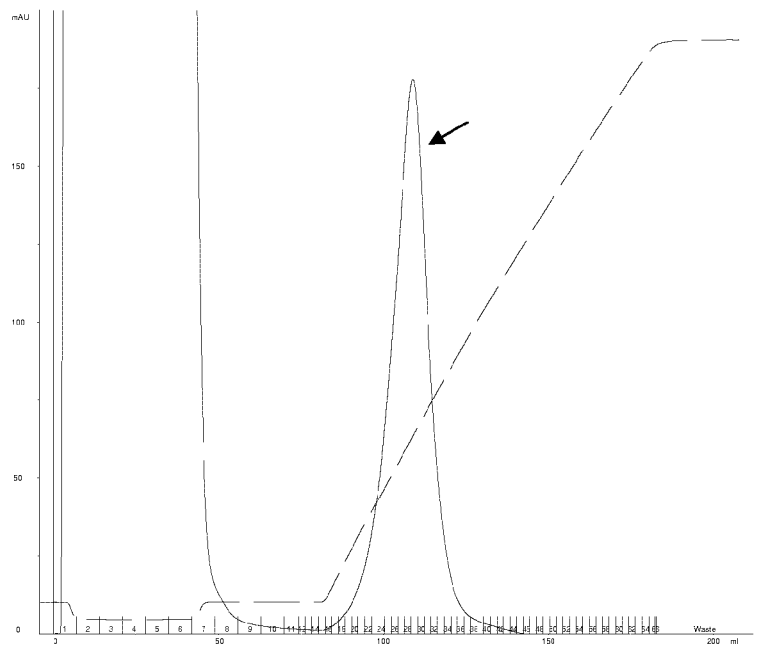
B
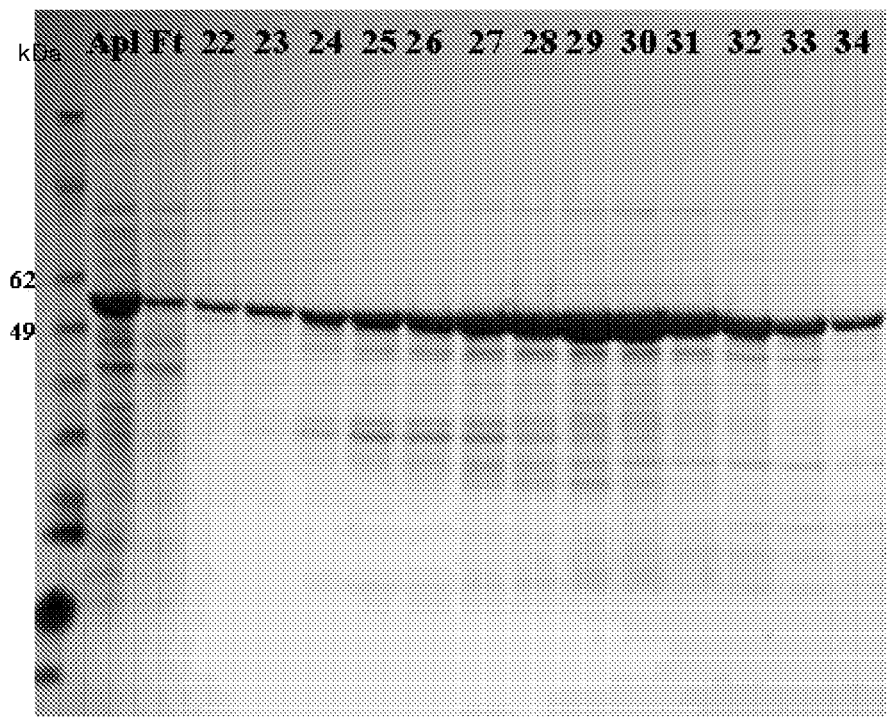

Fig. 4
A
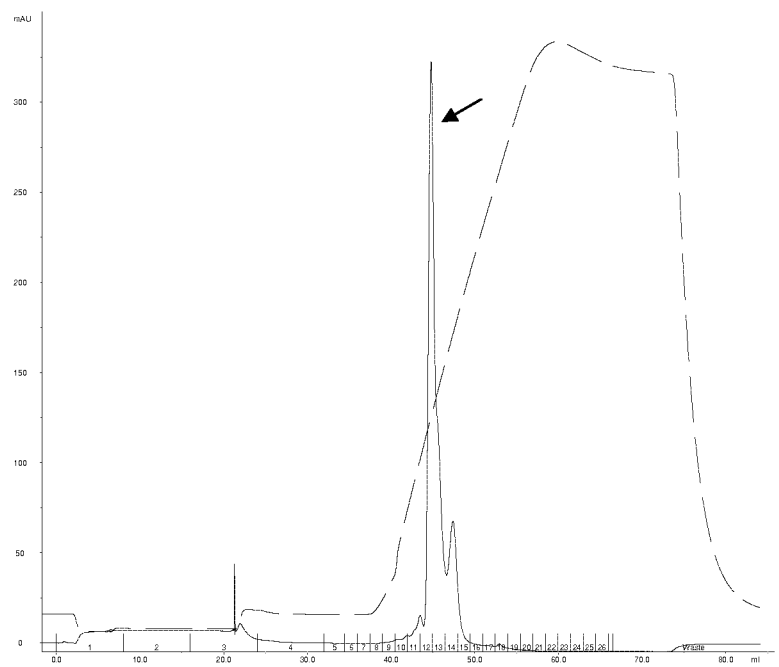
B
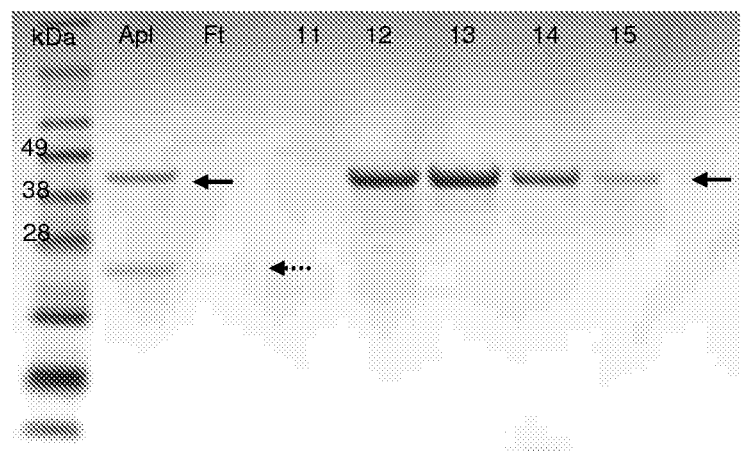

Fig. 5A1
+TAP, MES pH5.5
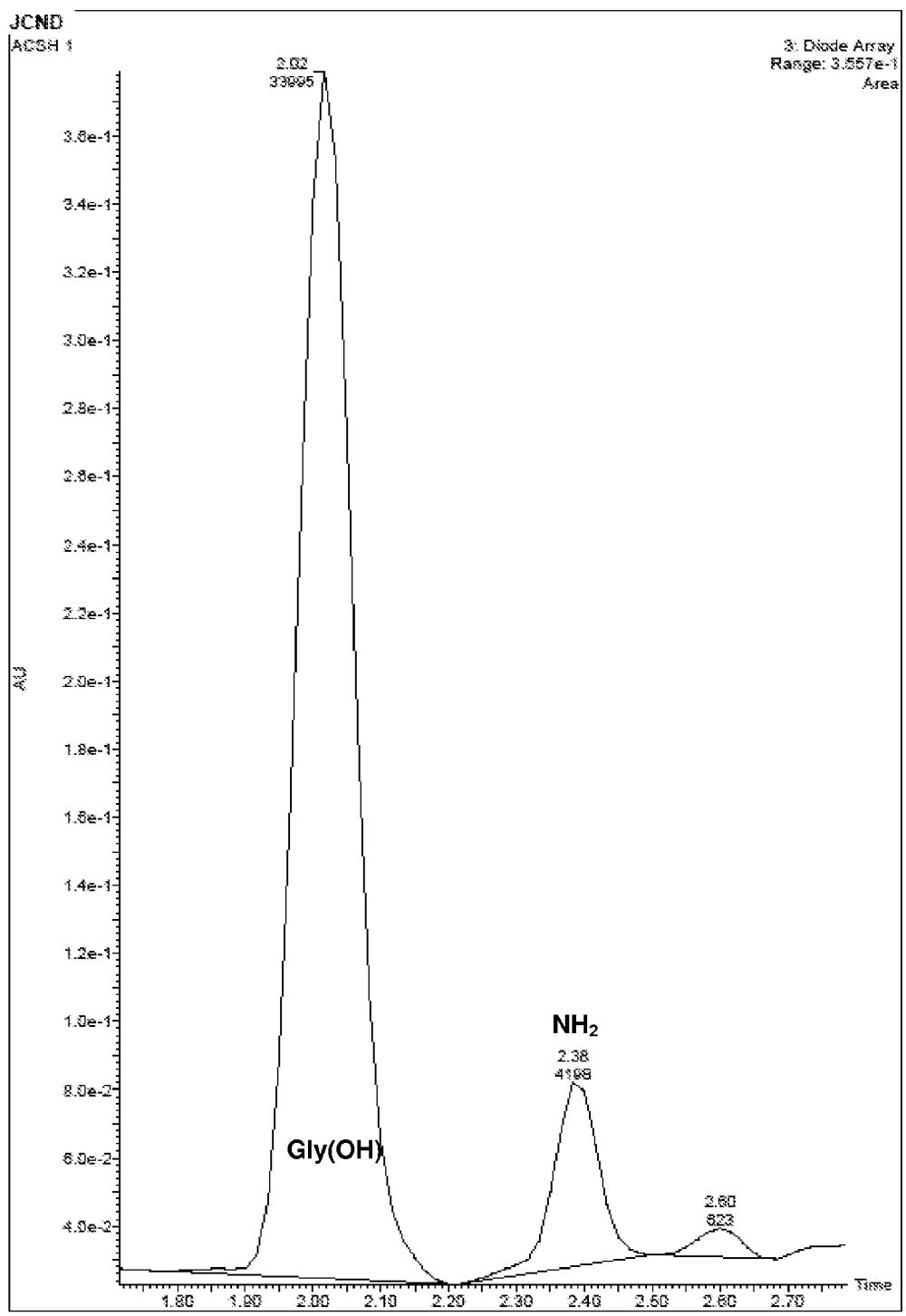

Fig. 5A2
+TAP, Tris pH7.5
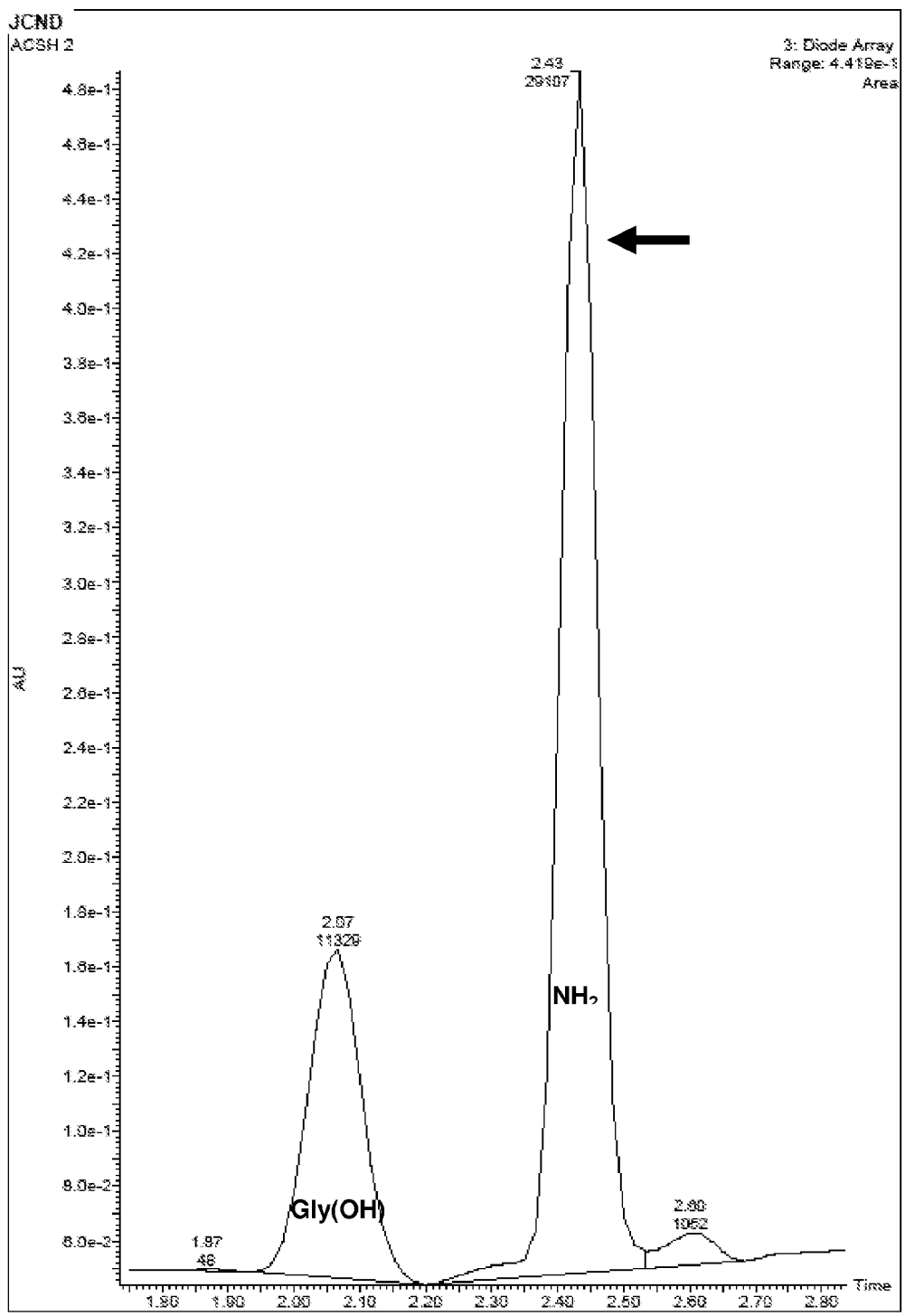

Fig. 5A3
-TAP, MES pH5.5
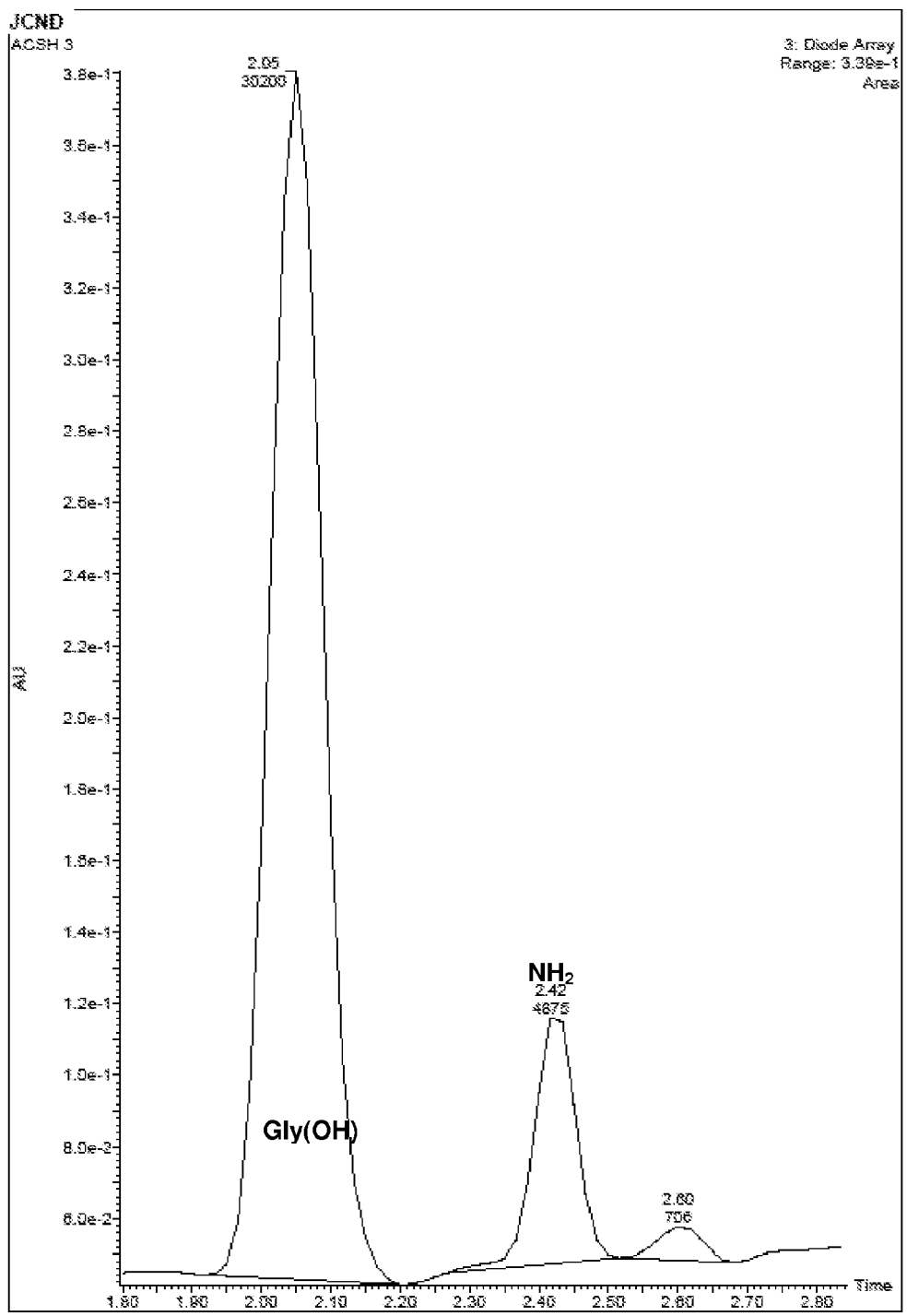

Fig. 5A4
-TAP, Tris pH7.5
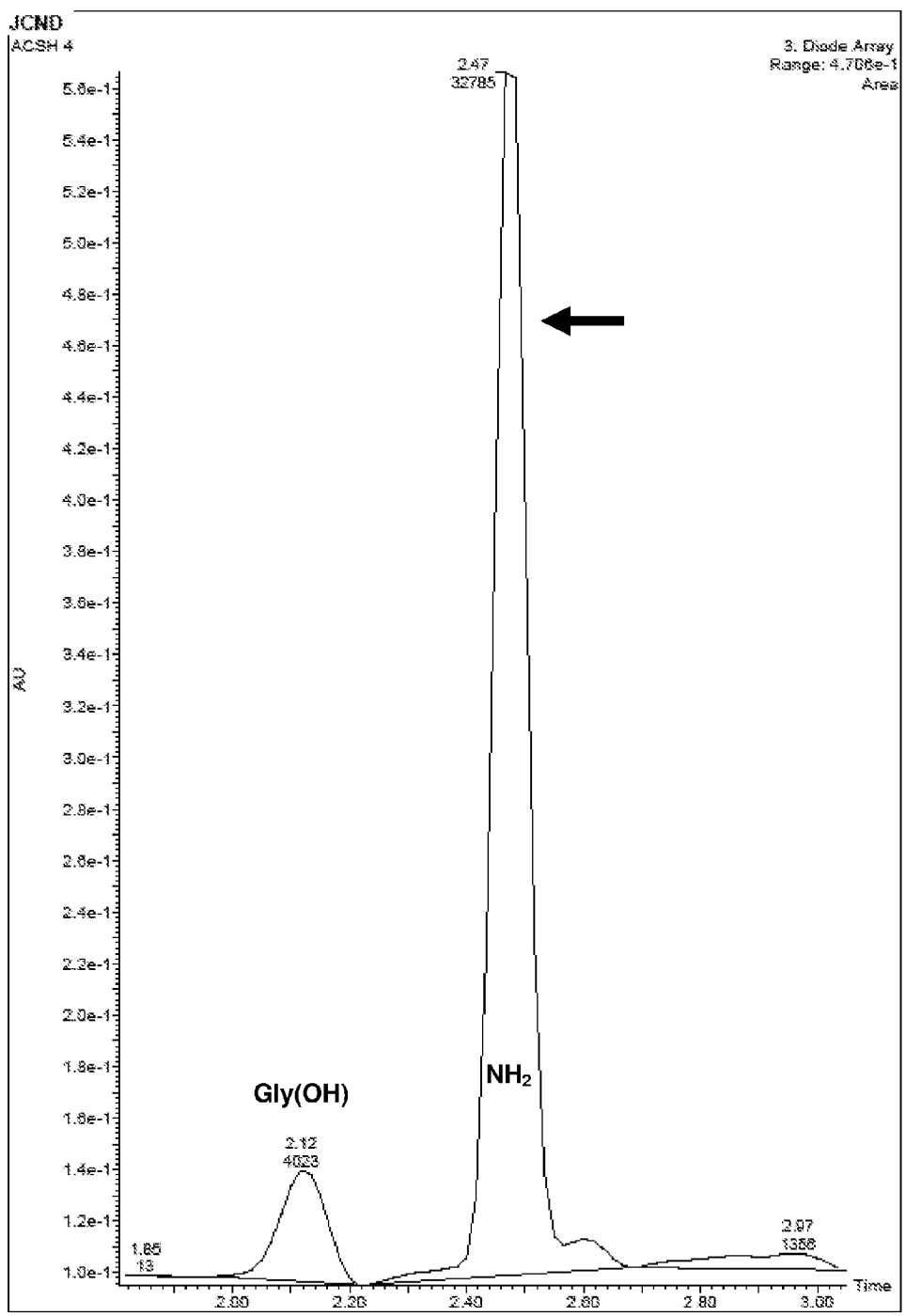

Fig. 5A5
MES pH 5.5, neg.ctrl
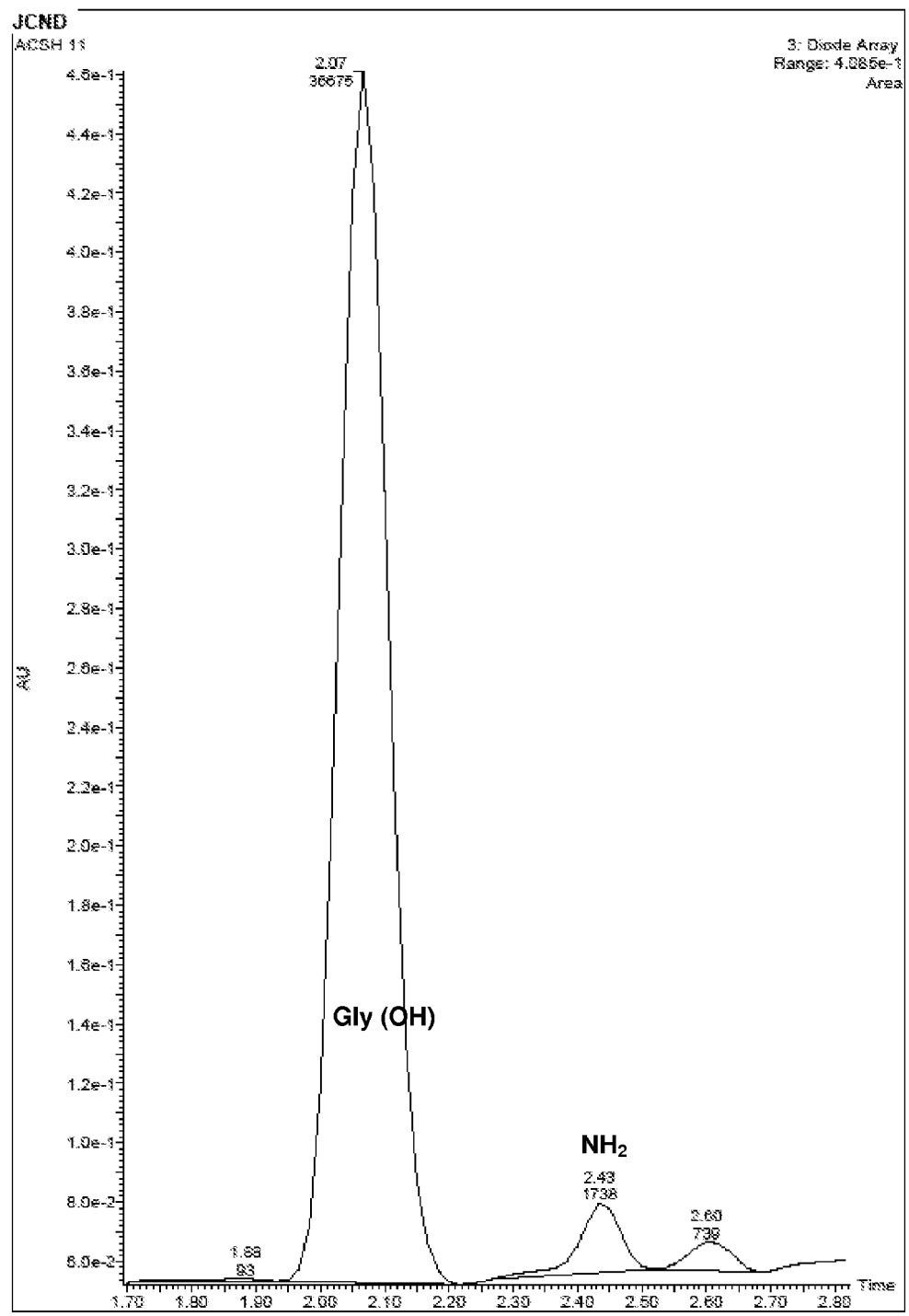

Fig. 5A6
Tris pH 7.5, neg.ctrl
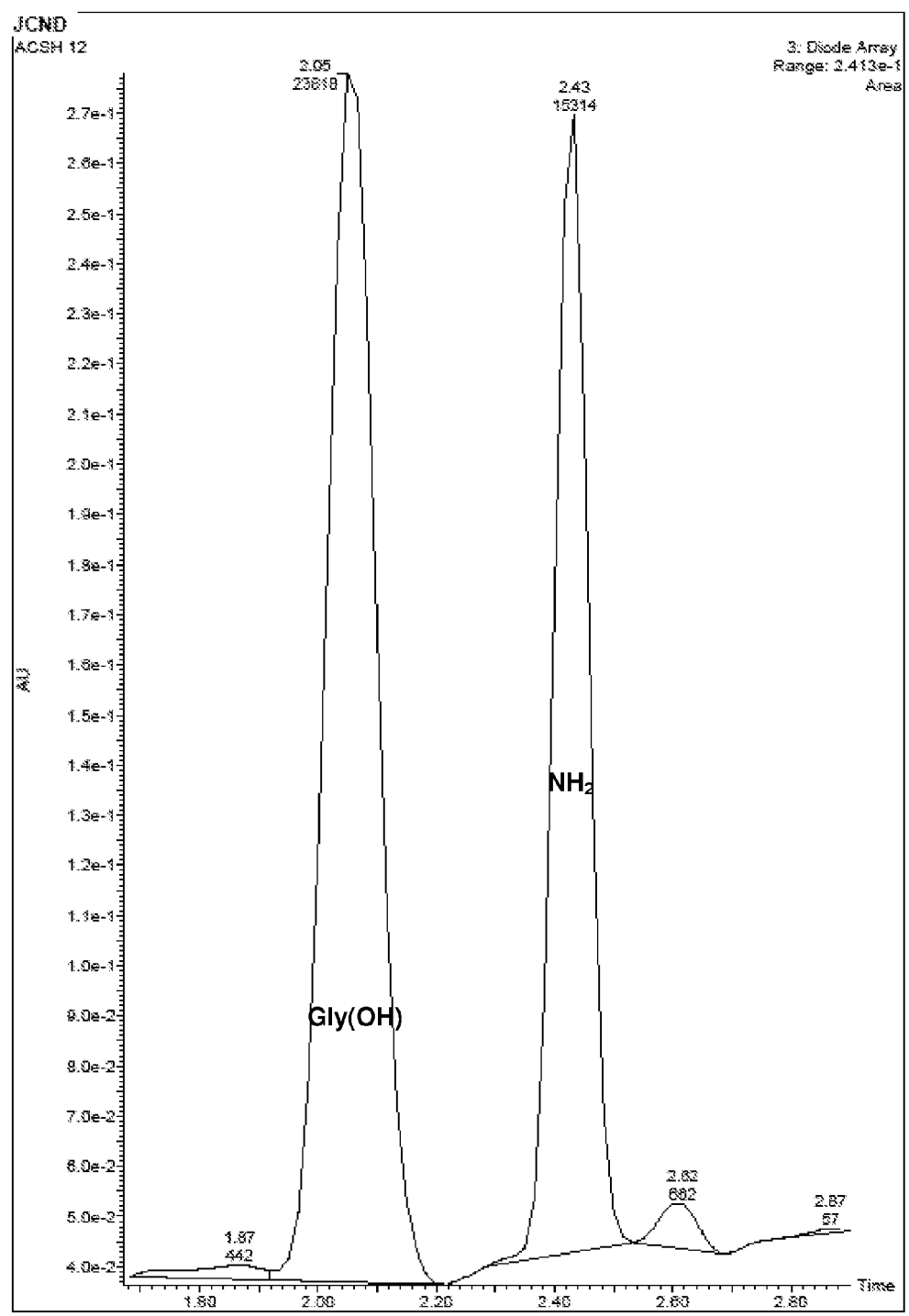

Fig. 5B1
+TAP tag  MES pH 5.5
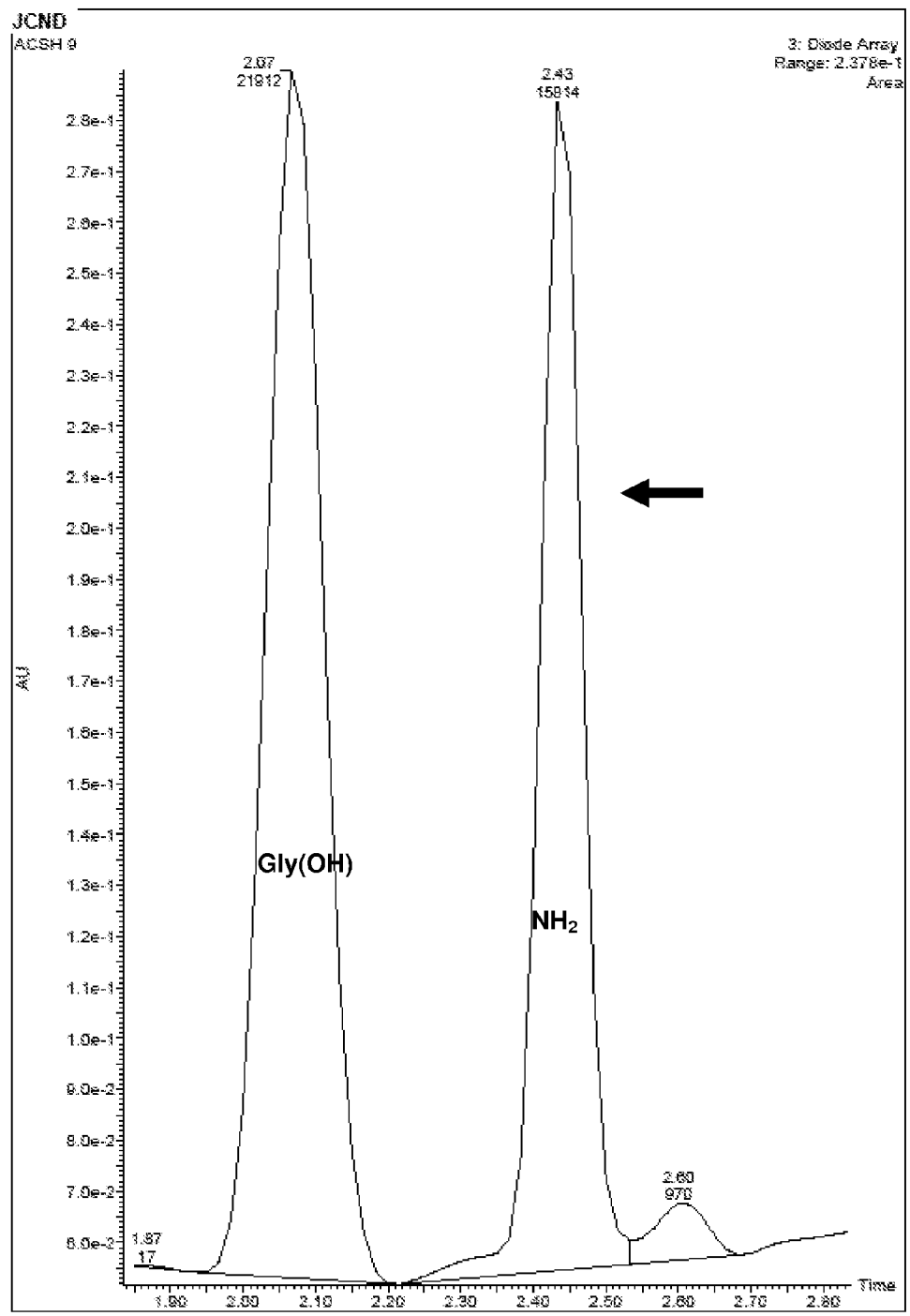

Fig. 5B2
+TAP tag, Tris pH 7.5
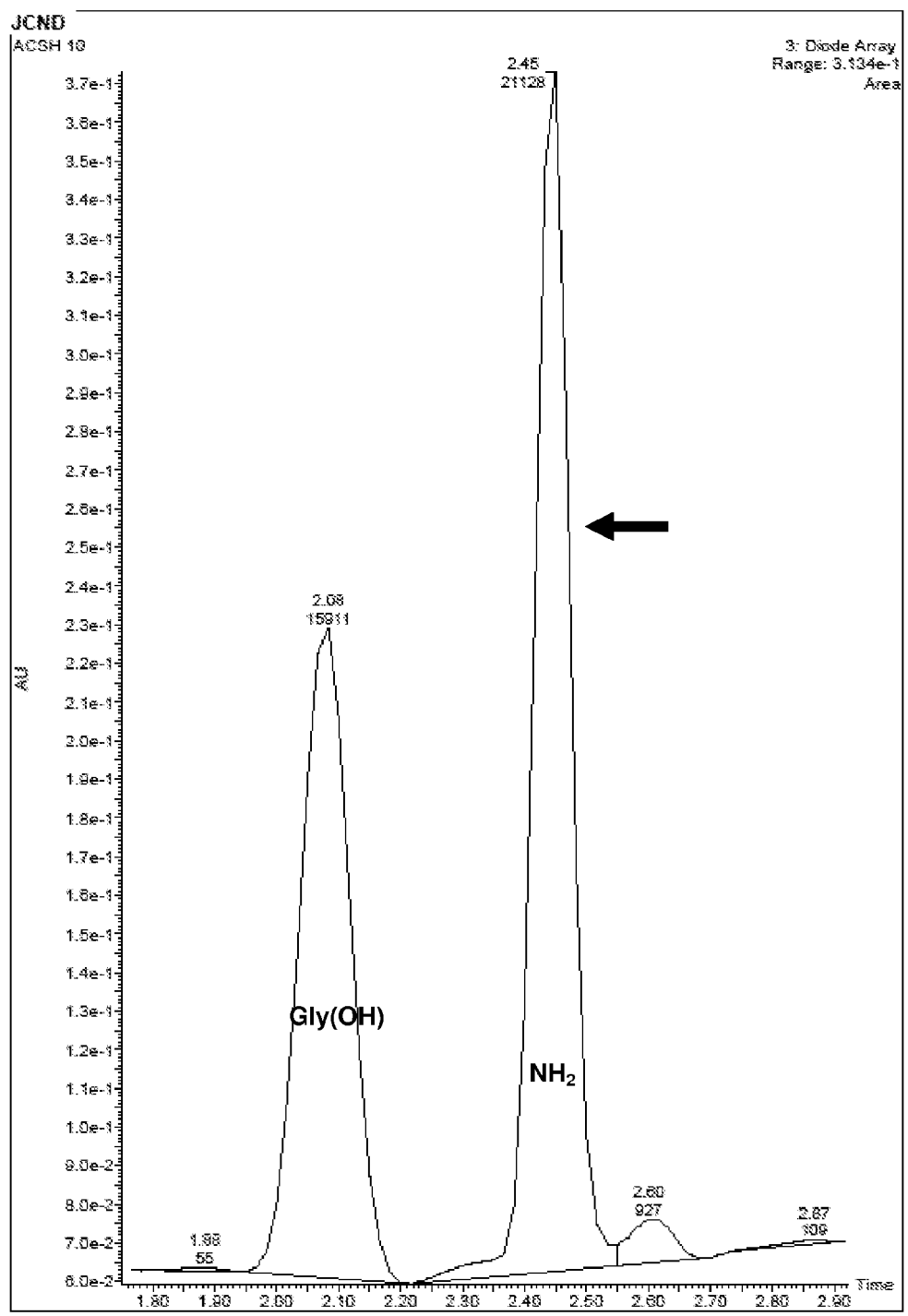

Fig. 5B3
Neg. Ctrl, MES pH 5.5
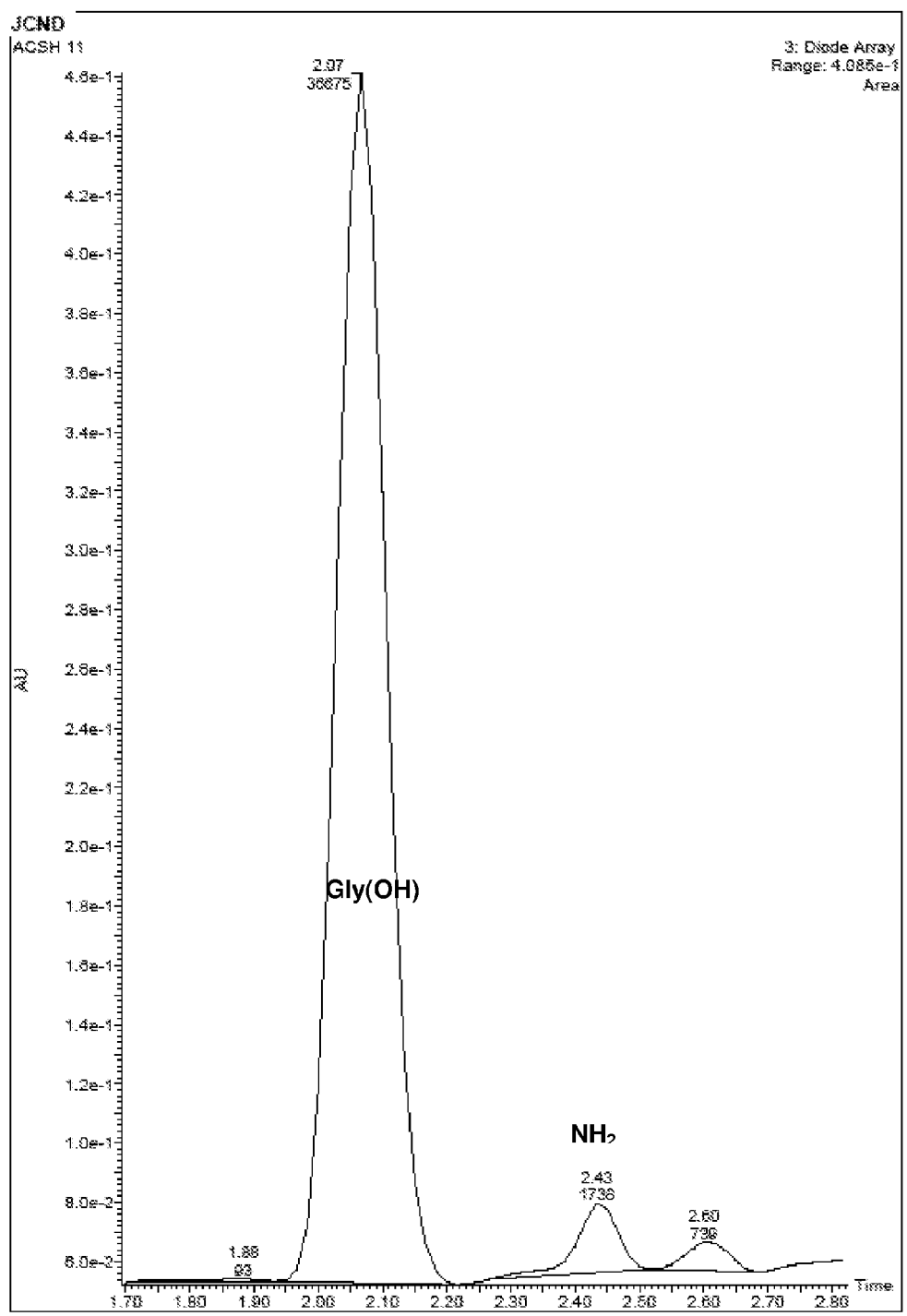

Fig. 5B4
Neg. Ctrl, Tris pH 7.5
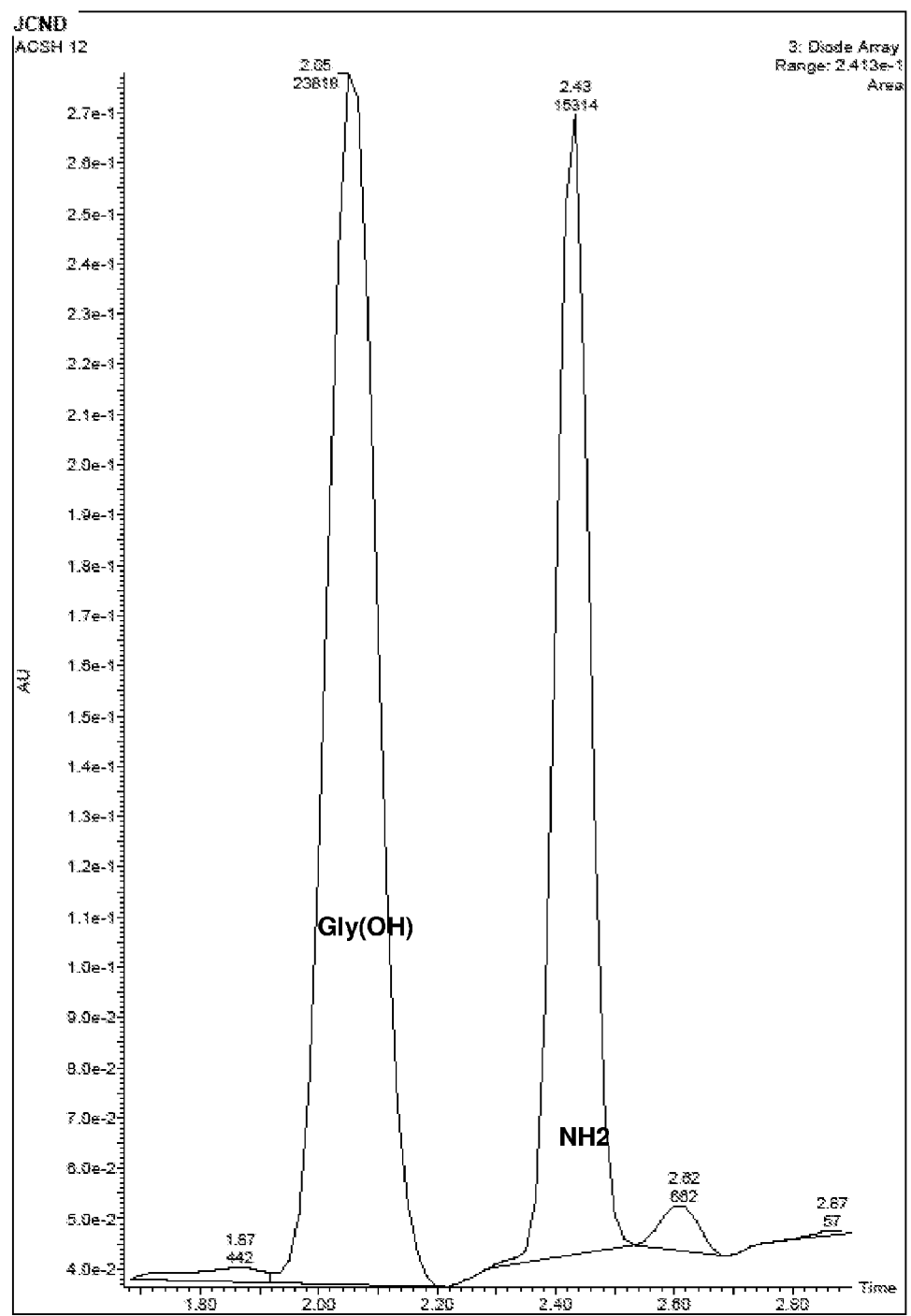

Fig. 7A
Erythrobacter PAL-like domain (SEQ ID NO: 1)
ctrl
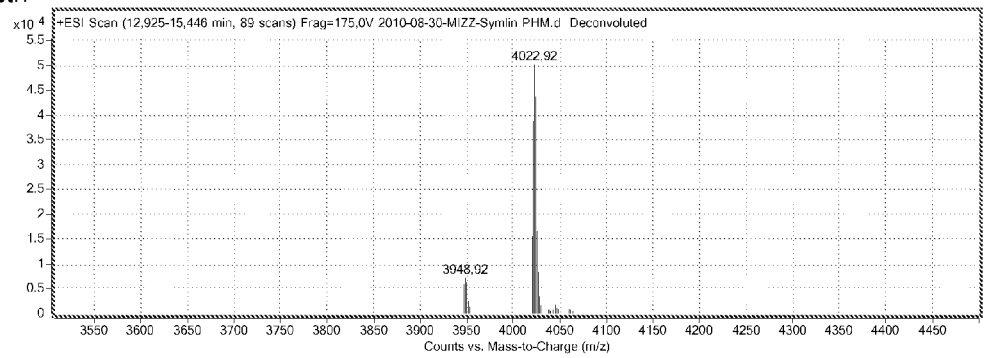
1:1250
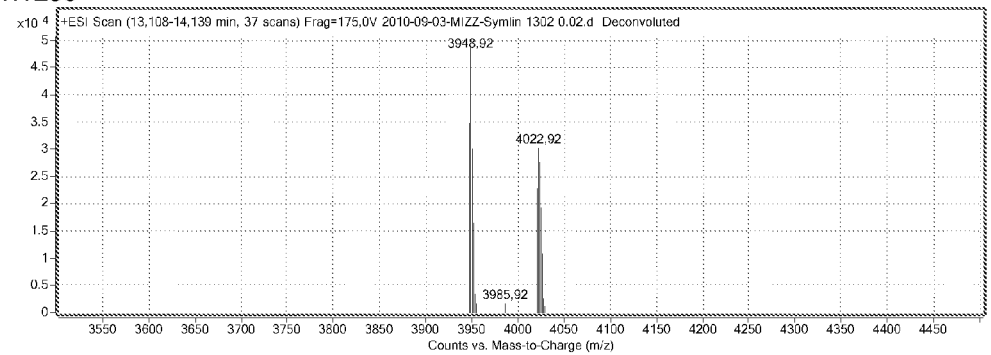
1:500
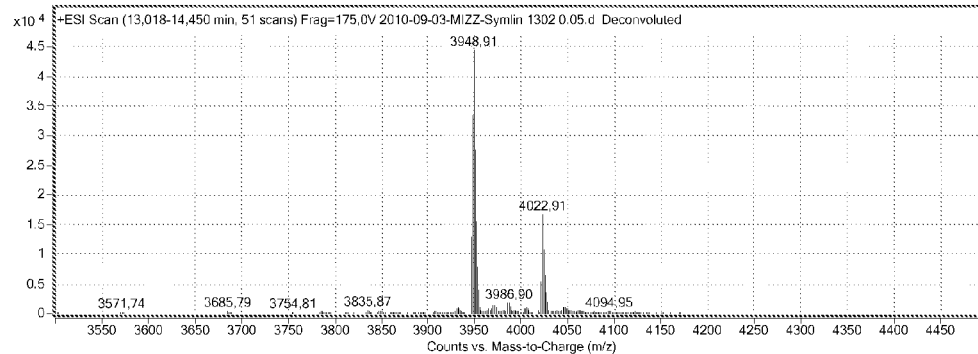

Fig. 7A(Cont.)
1:100
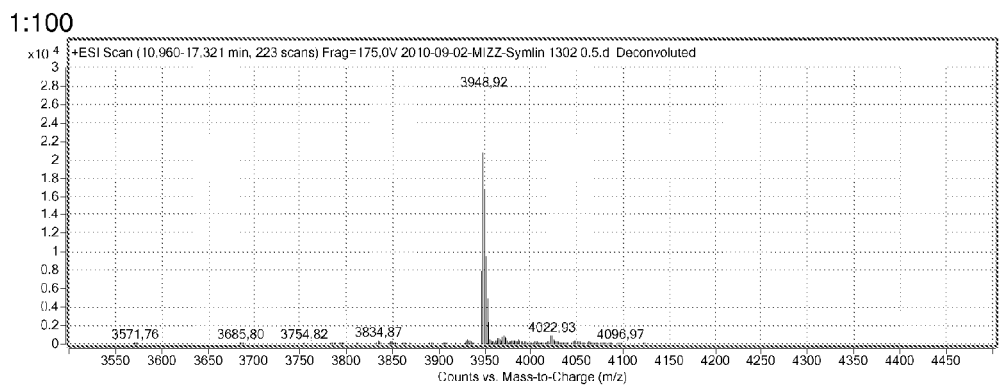
Fig. 7B
Planctomyces PAL-like domain (SEQ ID NO: 4)
ctrl
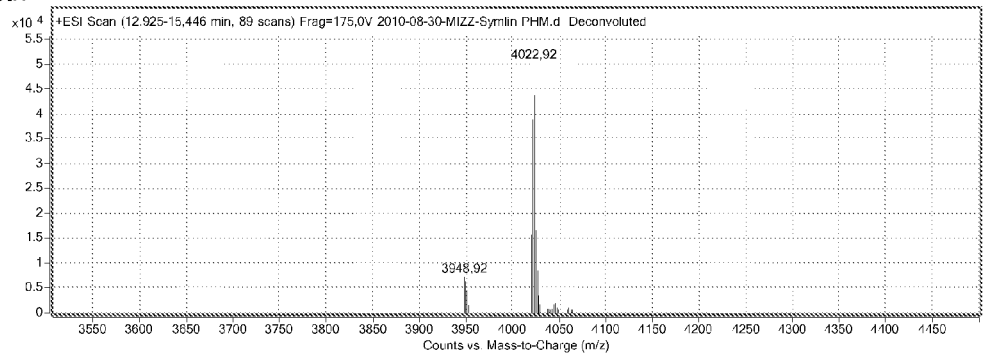
1:1250
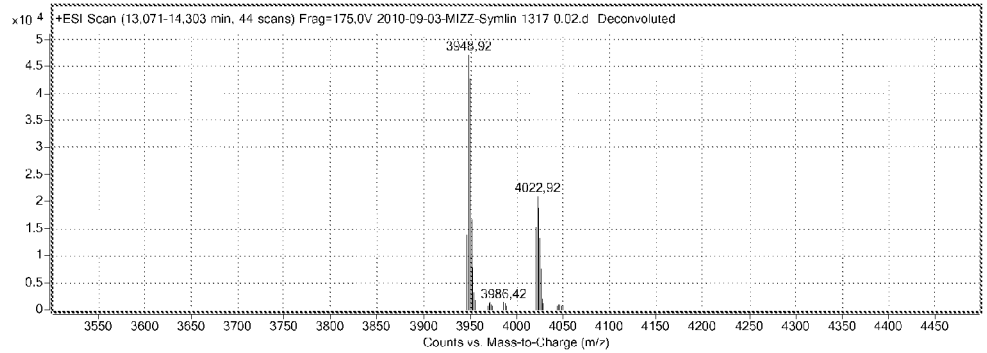

Fig. 7B(Cont.)
1:500
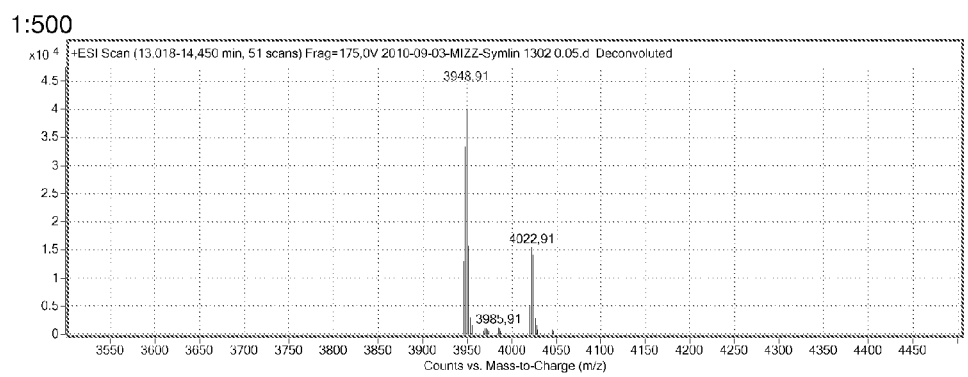
1:100
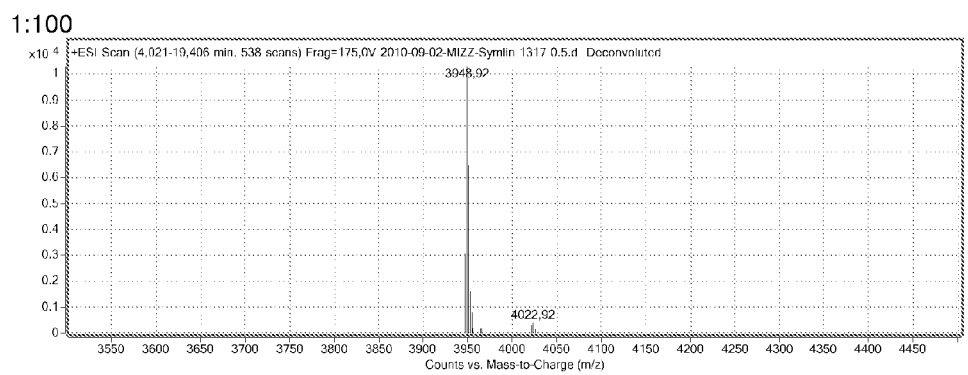
Fig. 7C
Exiguobacterium PAL-like domain (SEQ ID NO: 2)
ctrl
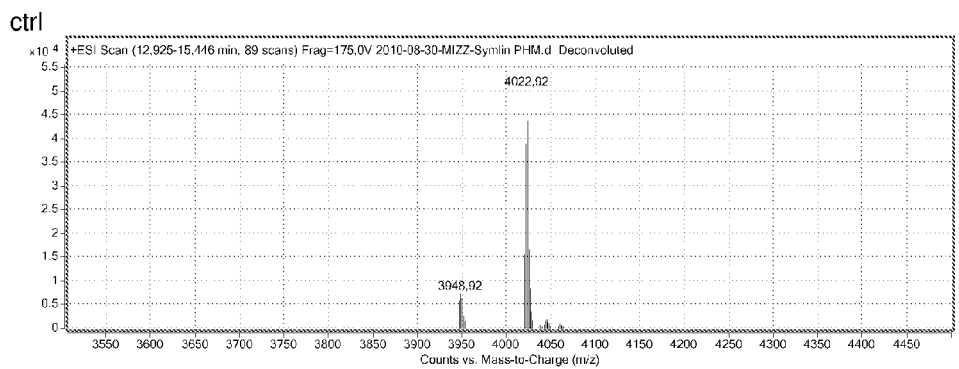

Fig. 7C(Cont.)
1:100
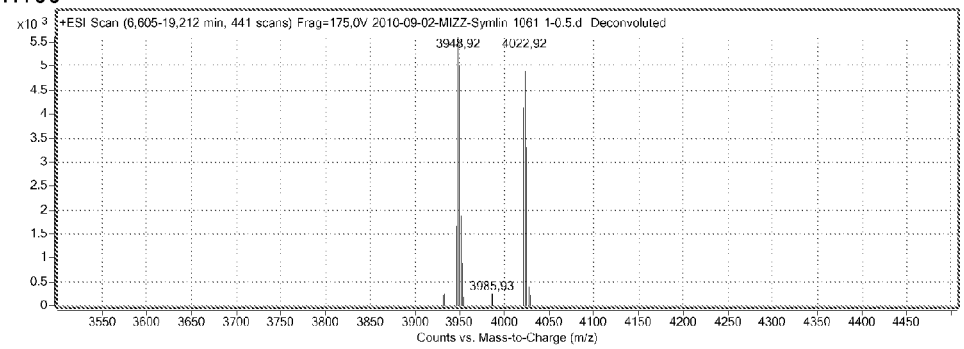
1:50
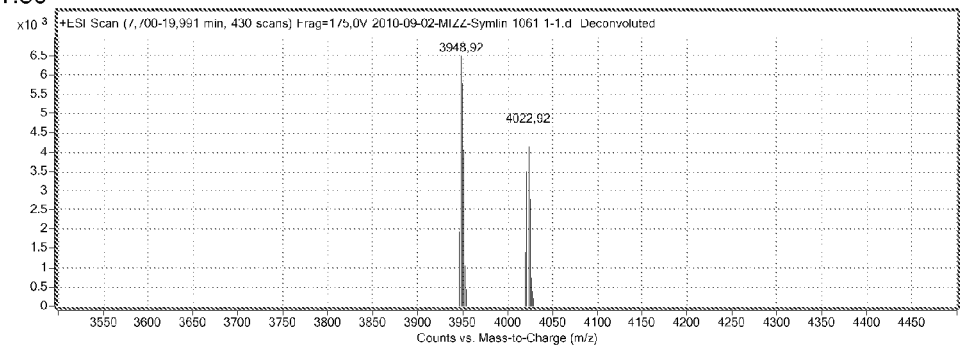
1:25
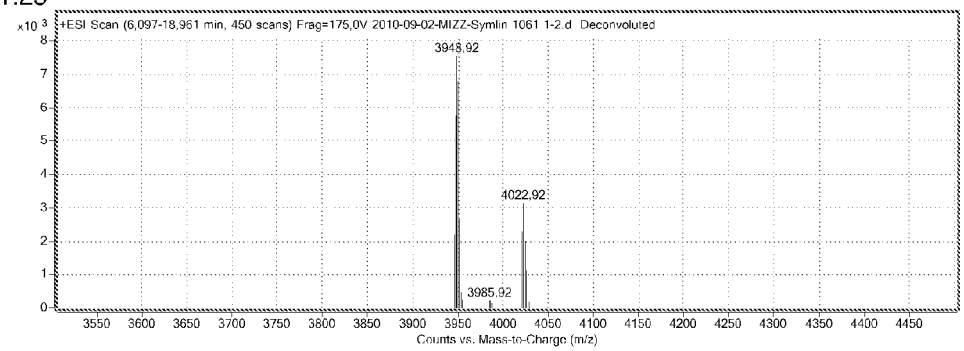

Fig. 7D
Chthoniobacter PAL-like domain (SEQ ID NO: 3)
ctrl
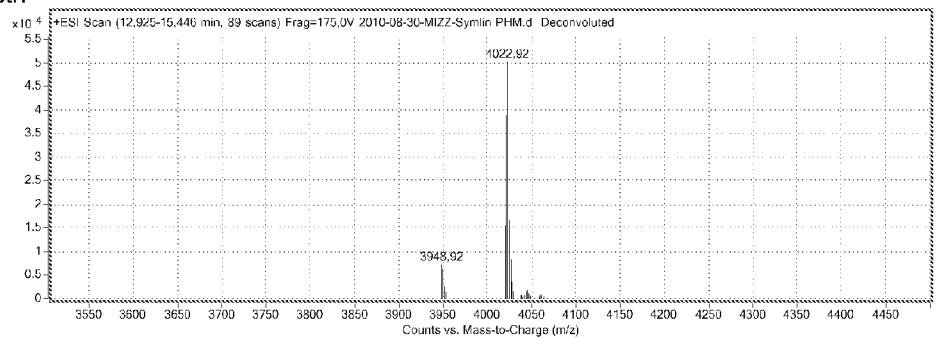
1:100
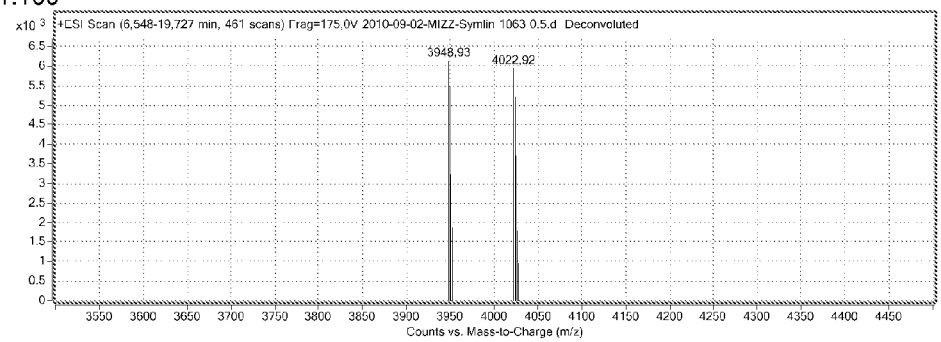
1:50
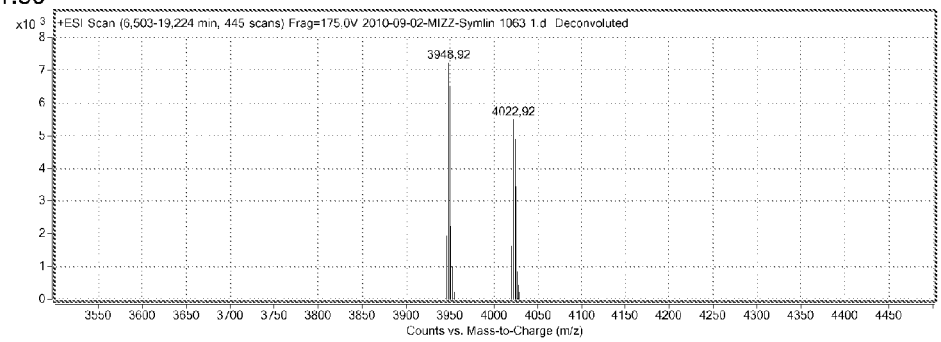

SEQUENCE LISTING

```
<160> NUMBER OF SEQ ID NOS: 18

<210> SEQ ID NO 1
<211> LENGTH: 306
<212> TYPE: PRT
<213> ORGANISM: Erythrobacter

<400> SEQUENCE: 1

Gly Pro Pro Val Thr Ile Asp Glu Ser Trp Pro Asp Ile Pro Glu Ser
1               5                   10                  15

Ala Val Phe Gly Glu Pro Thr Ala Ile Asp Val Asp Ser His Gly His
            20                  25                  30

Ile Phe Val Leu His Arg Ala Gly Arg Glu Trp Thr Gln Pro Phe Pro
        35                  40                  45

Ser Asp Pro Ile Ser Glu Pro Thr Val Phe Met Phe Ala Ala Asn Gly
    50                  55                  60

Lys Leu Leu Ser Lys Trp Gly Ala Gly Glu Leu Val Met Pro His Gly
65                  70                  75                  80

Leu Ser Ile Asp Gly Asp Asn Lys Val Trp Ile Thr Asp Val Ala Arg
                85                  90                  95

Glu Gln Val Leu Arg Phe Thr His Glu Gly Ala Glu Glu Leu Val Leu
            100                 105                 110

Gly Thr Arg Gly Glu Thr Gly Gln Asp Glu Ser His Phe Gly Arg Pro
        115                 120                 125

Ala Asp Val Thr Phe Val Gly Asp Arg Val Leu Val Ala Asp Gly Tyr
    130                 135                 140

Leu Asn Arg Arg Ile Met Val Phe Asp Arg Ala Gly Asn Phe Leu Glu
145                 150                 155                 160

Gln Trp Gly Lys Glu Gly Glu Asp Ala Gly Glu Phe Asn Leu Pro His
                165                 170                 175

Ala Ile Ala Ala Asp Ser Glu Arg Ile Tyr Val Ala Asp Arg Glu Asn
            180                 185                 190
```

```
Ala Arg Val Gln Val Leu Ser Leu Asp Gly Glu Pro Leu Ala Arg Trp
        195                 200                 205

Arg Gln Asp Gly Thr Gly His Pro Tyr Ala Val Lys Pro Ile Gly Ser
    210                 215                 220

Gly Tyr Val Leu Ala Ile Glu Gly Arg Asp Arg Ala Gly Arg Asn Thr
225                 230                 235                 240

Ala Ile Gly Arg Ile Tyr Arg Ala Asp Gly Gly Leu Glu Arg Val Phe
                245                 250                 255

Asp Ala Gly Val Glu Pro His Thr Gly Thr Ser Leu Gly His Asp Val
            260                 265                 270

Ala Ile Gly Pro Asp Gly Ser Ala Tyr Met Val Asp Asn Lys Ala Asn
        275                 280                 285

Arg Val Ile Lys Phe Asp Leu Ser Arg Ala Gly Val Glu Glu Ala Asp
    290                 295                 300

Ala Asp
305

<210> SEQ ID NO 2
<211> LENGTH: 336
<212> TYPE: PRT
<213> ORGANISM: Exiguobacterium

<400> SEQUENCE: 2

Gly Pro Arg Thr Asp Pro Ile Phe Lys Asp Glu Tyr Asp Glu Lys Ala
1               5                   10                  15

Lys Ser Ser Arg Tyr Thr Ser Ser Trp Val Trp Pro Glu Lys Asp Ser
            20                  25                  30

Val Ser His Arg Gly Gly Glu Gly Ser Gly Val Ser Thr Ser Pro Ser
        35                  40                  45

Gly Tyr Val Tyr Tyr Leu His Arg Gly Asp Gly Ser Tyr Ala Asn Glu
    50                  55                  60

Glu Leu Ile Thr Thr Pro Thr Ile Thr Val Phe Asp Pro Asn Thr Asn
65                  70                  75                  80

Glu Ile Val Asp Glu Phe Gly Asp Asn Leu Phe Gln Ser Pro His Gly
                85                  90                  95

Ile Glu Val Asp Ser Gln Asn Asn Ile Trp Val Thr Asp Ile Met Leu
            100                 105                 110

Asn Lys Val Phe Lys Leu Asp Glu Arg Gly Asn Val Leu Ala Thr Phe
        115                 120                 125

Gly Asp Asp Tyr Arg Leu Gly Thr Glu Thr Ser Leu Arg Ile Arg Asn
    130                 135                 140

Glu Leu Pro Asn Phe Pro Val Pro Met Asn Glu Tyr Thr Phe Ala Arg
145                 150                 155                 160

Pro Thr Asp Val Thr Val Met Glu Asp Gly Ser Phe Ile Val Ala Asp
                165                 170                 175

Gly Tyr Arg Asn His Arg Ile Val Lys Phe Asn Arg Asp Gly Asn Ile
            180                 185                 190

Gln Trp Glu Val Asp Ala Tyr Gly Ser Ser Asp Gly Glu Phe Asn Leu
        195                 200                 205

Pro His Gly Ile Thr His Asp Gln Ser Gly Asn Ile Tyr Val Ala Asp
    210                 215                 220

Arg Asn Asn Ala Arg Ile Gln Val Phe Asp Gln Asp Gly Gln His Leu
225                 230                 235                 240

Ser Thr Trp Asp Asp Thr Glu Ile Gly Arg Pro Tyr Gly Ile Asp Ala
                245                 250                 255
```

```
Gly Asn Asp Gly Asn Ile Tyr Leu Val Asp Gly Gly Asp Tyr Leu Asn
                260                 265                 270

Gly Glu Arg Glu Thr Pro Lys Ser Gln Ile Val Val Leu Ser Pro Lys
            275                 280                 285

Gly Glu Val Ile Glu Arg Phe Gly Ser Trp Gly Asn Lys Met Gly Gln
        290                 295                 300

Leu Arg Ile Pro His Asp Leu Thr Val Leu Glu Asp Gly Thr Ile Phe
305                 310                 315                 320

Val Ala Glu Leu Leu Asn Glu Arg Leu Gln Lys Phe Thr Ile Thr Glu
                325                 330                 335

<210> SEQ ID NO 3
<211> LENGTH: 305
<212> TYPE: PRT
<213> ORGANISM: Chthoniobacter flavus

<400> SEQUENCE: 3

Gly Pro Glu Ser Arg Tyr Glu Val Val Pro His Trp Pro Val Leu Pro
1               5                   10                  15

Glu Gly Arg Ser Leu Gly Val Cys Ala Gly Val Gly Val Asp Ser His
            20                  25                  30

Gly Asn Val Phe Val Phe His Arg Asn Glu Arg Asn Trp Thr Ala Ala
        35                  40                  45

Phe Pro Glu Glu Pro Ile Ala Glu Pro Thr Ile Ser Val Phe Asp Gly
    50                  55                  60

Gln Ser Gly Lys Leu Leu Thr Glu Trp Gly Ala Gly Glu Phe Ile Met
65                  70                  75                  80

Pro His Gly Leu Thr Leu Asp Arg Glu Asp Asn Val Trp Leu Thr Asp
                85                  90                  95

Val Gly Arg Gln Gln Val Phe Lys Tyr Ala His Asp Gly His Leu Leu
            100                 105                 110

Leu Thr Leu Gly Glu Arg Gly Val Ala Gly Ser Asp Gln Thr His Phe
        115                 120                 125

Asn Leu Pro Thr Asp Val Ala Val Leu Pro Asp Gly Ser Phe Tyr Val
    130                 135                 140

Ser Asp Gly Tyr Arg Asn Thr Arg Val Val Lys Phe Asp Ala Ala Gly
145                 150                 155                 160

His Tyr Gln Phe Glu Trp Gly Gly Lys Gly Thr Glu Pro Gly Lys Phe
                165                 170                 175

Arg Leu Pro His Gly Val Ala Val Asp Ser His Gly Arg Val Phe Val
            180                 185                 190

Cys Asp Arg Thr Asn Ser Arg Leu Gln Val Phe Asp Pro Lys Gly Lys
        195                 200                 205

Phe Leu Ala Glu Trp Lys Gly Pro Gln Val Gly Arg Pro Tyr Gly Val
    210                 215                 220

Ser Val Ala Ala Asn Asp His Val Phe Val Ile Asp Gly Gly Asp Gln
225                 230                 235                 240

Leu Pro Asn Gln Pro Glu His Ala Lys Ala Val Glu Leu Asp Pro Glu
                245                 250                 255

Gly Asn Val Val Pro Arg Phe Gly Ser Tyr Gly Arg Asp Pro Gly Gln
            260                 265                 270

Phe Gln Leu Gly His Asp Ile Ala Val Ala Pro Asp Gly Ser Val Tyr
        275                 280                 285

Val Gly Asp Ala Lys Gly Lys Arg Val Gln Lys Phe Val Pro Val His
```

Pro
305

<210> SEQ ID NO 4
<211> LENGTH: 279
<212> TYPE: PRT
<213> ORGANISM: Planctomyces maris

<400> SEQUENCE: 4

Gly Pro Ala Asp Lys Ile Asp Phe Glu Pro Ala Ala Ile Asn Ile Glu
1               5                   10                  15

Leu Pro Glu Gly Leu Ala Leu Gly Pro Ala Ser Ala Val Asp Phe Asp
            20                  25                  30

Ser Lys Gly Arg Met Tyr Leu Phe His Arg Gly Pro Gln Pro Ile Leu
        35                  40                  45

Val Phe Asp Gln Ser Gly Lys Phe Val Arg Ser Trp Gly Asp Lys Leu
    50                  55                  60

Ile Ser Gln Ala His Gly Leu Arg Val Ala Pro Asp Glu Thr Ile Trp
65                  70                  75                  80

Val Thr Asp Ile Gly Asn His Met Val Phe Gln Phe Asn Pro Glu Gly
                85                  90                  95

Lys Leu Leu Leu Ala Leu Gly Gln Ala Gly Lys Pro Gly Asp Ser Gln
            100                 105                 110

Asp Gln Phe Asn Lys Pro Thr Asp Ile Ala Phe Gly Pro Gln Gly Glu
        115                 120                 125

Phe Tyr Ile Ser Asp Gly Tyr Gly Asn Ser Arg Val Met Lys Phe Ala
    130                 135                 140

Ala Asn Gly Lys Asn Leu Gly Gln Trp Gly Thr Pro Gly Lys Gly Pro
145                 150                 155                 160

Gly Glu Phe Asn Leu Pro His Ser Ile Leu Val Asp Ala Lys Gly Arg
                165                 170                 175

Val Leu Val Gly Asp Arg Glu Asn Asp Arg Val Gln Ile Phe Asp Leu
            180                 185                 190

Glu Gly Asn Leu Leu Glu Ile Trp Thr Gly Phe Ala Pro Tyr Gly Met
        195                 200                 205

Glu Phe Asp Ser Arg Gly Asn Leu Phe Val Ala Asp Gly Arg Ala Asn
    210                 215                 220

Lys Val Leu Gln Leu Asn Ala Ser Gly Lys Val Glu Asn Ser Trp Gly
225                 230                 235                 240

Lys Thr Gly Lys Glu Pro Gly Glu Tyr Asn Leu Pro His Met Leu Ala
                245                 250                 255

Val Asp Ala Ala Gly Asn Leu Phe Val Thr Glu Ile Gly Gly Lys Arg
            260                 265                 270

Leu Gln Lys Leu Gln Arg Lys
        275

<210> SEQ ID NO 5
<211> LENGTH: 324
<212> TYPE: PRT
<213> ORGANISM: Rattus norvegicus

<400> SEQUENCE: 5

Gly Asp Phe His Val Glu Glu Glu Leu Asp Trp Pro Gly Val Tyr Leu
1               5                   10                  15

Leu Pro Gly Gln Val Ser Gly Val Ala Leu Asp Ser Lys Asn Asn Leu

```
            20                  25                  30
Val Ile Phe His Arg Gly Asp His Val Trp Asp Gly Asn Ser Phe Asp
            35                  40                  45

Ser Lys Phe Val Tyr Gln Gln Arg Gly Leu Gly Pro Ile Glu Glu Asp
50                  55                  60

Thr Ile Leu Val Ile Asp Pro Asn Asn Ala Glu Ile Leu Gln Ser Ser
65                  70                  75                  80

Gly Lys Asn Leu Phe Tyr Leu Pro His Gly Leu Ser Ile Asp Thr Asp
                85                  90                  95

Gly Asn Tyr Trp Val Thr Asp Val Ala Leu His Gln Val Phe Lys Leu
            100                 105                 110

Asp Pro His Ser Lys Glu Gly Pro Leu Leu Ile Leu Gly Arg Ser Met
            115                 120                 125

Gln Pro Gly Ser Asp Gln Asn His Phe Cys Gln Pro Thr Asp Val Ala
130                 135                 140

Val Glu Pro Ser Thr Gly Ala Val Phe Val Ser Asp Gly Tyr Cys Asn
145                 150                 155                 160

Ser Arg Ile Val Gln Phe Ser Pro Ser Gly Lys Phe Val Thr Gln Trp
                165                 170                 175

Gly Glu Glu Ser Ser Gly Ser Ser Pro Arg Pro Gly Gln Phe Ser Val
            180                 185                 190

Pro His Ser Leu Ala Leu Val Pro His Leu Asp Gln Leu Cys Val Ala
            195                 200                 205

Asp Arg Glu Asn Gly Arg Ile Gln Cys Phe Lys Thr Asp Thr Lys Glu
210                 215                 220

Phe Val Arg Glu Ile Lys His Ala Ser Phe Gly Arg Asn Val Phe Ala
225                 230                 235                 240

Ile Ser Tyr Ile Pro Gly Phe Leu Phe Ala Val Asn Gly Lys Pro Tyr
                245                 250                 255

Phe Gly Asp Gln Glu Pro Val Gln Gly Phe Val Met Asn Phe Ser Ser
            260                 265                 270

Gly Glu Ile Ile Asp Val Phe Lys Pro Val Arg Lys His Phe Asp Met
            275                 280                 285

Pro His Asp Ile Val Ala Ser Glu Asp Gly Thr Val Tyr Ile Gly Asp
290                 295                 300

Ala His Thr Asn Thr Val Trp Lys Phe Thr Leu Thr Glu Lys Met Glu
305                 310                 315                 320

His Arg Ser Val

<210> SEQ ID NO 6
<211> LENGTH: 323
<212> TYPE: PRT
<213> ORGANISM: Xenopus laevis

<400> SEQUENCE: 6

Gly Asp Val His Leu Glu Glu Asp Thr Asp Trp Pro Gly Val Asn Leu
1               5                   10                  15

Lys Val Gly Gln Val Ser Gly Leu Ala Leu Asp Pro Lys Asn Asn Leu
            20                  25                  30

Ala Ile Phe His Arg Gly Asp His Val Trp Asp Glu Asn Ser Phe Asp
            35                  40                  45

Arg Asn Phe Val Tyr Gln Gln Arg Gly Ile Gly Pro Ile Gln Glu Ser
50                  55                  60

Thr Ile Leu Val Val Asp Pro Ser Ser Ser Lys Val Leu Lys Ser Thr
```

```
                65                  70                  75                  80
Gly Lys Asn Leu Phe Phe Leu Pro His Gly Leu Thr Ile Asp Arg Asp
                    85                  90                  95

Gly Asn Tyr Trp Val Thr Asp Val Ala Leu His Gln Val Phe Lys Leu
                100                 105                 110

Gly Ala Gly Lys Glu Thr Pro Leu Leu Val Leu Gly Arg Ala Phe Gln
            115                 120                 125

Pro Gly Ser Asp Arg Lys His Phe Cys Gln Pro Thr Asp Val Ala Val
130                 135                 140

Asp Pro Ile Thr Gly Asn Phe Phe Val Ala Asp Gly Tyr Cys Asn Ser
145                 150                 155                 160

Arg Ile Met Gln Phe Ser Pro Asn Gly Met Phe Ile Met Gln Trp Gly
                165                 170                 175

Glu Glu Thr Ser Ser Asn Val Pro Arg Pro Gly Gln Phe Arg Ile Pro
                180                 185                 190

His Ser Leu Thr Met Val Pro Asp Gln Gly Gln Leu Cys Val Ala Asp
            195                 200                 205

Arg Glu Asn Gly Arg Ile Gln Cys Phe His Ala Glu Thr Gly Asn Phe
210                 215                 220

Val Lys Gln Ile Lys His Gln Glu Phe Gly Arg Glu Val Phe Ala Val
225                 230                 235                 240

Ser Tyr Ala Pro Gly Gly Val Leu Tyr Ala Val Asn Gly Lys Pro Tyr
                245                 250                 255

Tyr Gly Tyr Ser Ala Pro Val Gln Gly Phe Met Leu Asn Phe Ser Asn
                260                 265                 270

Gly Asp Ile Leu Asp Thr Phe Ile Pro Ala Arg Lys Asn Phe Asp Met
            275                 280                 285

Pro His Asp Ile Ala Ala Ala Asp Asp Gly Thr Val Tyr Val Gly Asp
290                 295                 300

Ala His Ala Asn Ala Val Trp Lys Phe Ser Pro Ser Lys Ala Glu His
305                 310                 315                 320

Arg Ser Val

<210> SEQ ID NO 7
<211> LENGTH: 149
<212> TYPE: PRT
<213> ORGANISM: Thermotoga maritima

<400> SEQUENCE: 7

Met Lys Val Ile Leu Leu Arg Asp Val Pro Lys Ile Gly Lys Lys Gly
1               5                   10                  15

Glu Ile Lys Glu Val Ser Asp Gly Tyr Ala Arg Asn Tyr Leu Ile Pro
                20                  25                  30

Arg Gly Phe Ala Lys Glu Tyr Thr Glu Gly Leu Glu Arg Ala Ile Lys
            35                  40                  45

His Glu Lys Glu Ile Glu Lys Arg Lys Glu Arg Glu Arg Glu Glu
    50                  55                  60

Ser Glu Lys Ile Leu Lys Glu Leu Lys Lys Arg Thr His Val Val Lys
65                  70                  75                  80

Val Lys Ala Gly Glu Gly Gly Lys Ile Phe Gly Ala Val Thr Ala Ala
                85                  90                  95

Thr Val Ala Glu Glu Ile Ser Lys Thr Thr Gly Leu Lys Leu Asp Lys
                100                 105                 110

Arg Trp Phe Lys Leu Asp Lys Pro Ile Lys Glu Leu Gly Glu Tyr Ser
```

-continued

```
            115                 120                 125
Leu Glu Val Ser Leu Pro Gly Gly Val Lys Asp Thr Ile Lys Ile Arg
    130                 135                 140

Val Glu Arg Glu Glu
145

<210> SEQ ID NO 8
<211> LENGTH: 13
<212> TYPE: PRT
<213> ORGANISM: ARTIFICIAL
<220> FEATURE:
<223> OTHER INFORMATION: synthetic

<400> SEQUENCE: 8

Ser Ser Ser Gly Gly Ser Gly Ser Glu Val Leu Phe Gln
1               5                   10

<210> SEQ ID NO 9
<211> LENGTH: 11
<212> TYPE: PRT
<213> ORGANISM: ARTIFICIAL
<220> FEATURE:
<223> OTHER INFORMATION: synthetic

<400> SEQUENCE: 9

Ser Ser Ser Gly Ser Gly Glu Val Leu Phe Gln
1               5                   10

<210> SEQ ID NO 10
<211> LENGTH: 10
<212> TYPE: PRT
<213> ORGANISM: ARTIFICIAL
<220> FEATURE:
<223> OTHER INFORMATION: synthetic

<400> SEQUENCE: 10

Ser Ser Ser Gly Gly Ser Gly Gly Ser Gly
1               5                   10

<210> SEQ ID NO 11
<211> LENGTH: 10
<212> TYPE: PRT
<213> ORGANISM: Erythrobacter

<400> SEQUENCE: 11

Met Gly Ser Ser His His His His His His
1               5                   10

<210> SEQ ID NO 12
<211> LENGTH: 12
<212> TYPE: PRT
<213> ORGANISM: ARTIFICIAL
<220> FEATURE:
<223> OTHER INFORMATION: synthetic

<400> SEQUENCE: 12

Ser Ser Gly Gly Ser Gly Ser Glu Val Leu Phe Gln
1               5                   10

<210> SEQ ID NO 13
<211> LENGTH: 307
<212> TYPE: PRT
<213> ORGANISM: Erythrobacter

<400> SEQUENCE: 13
```

```
Glu Ala Pro Pro Val Thr Ile Asp Glu Ser Trp Pro Asp Ile Pro Glu
1               5                   10                  15

Ser Ala Val Phe Gly Glu Pro Thr Ala Ile Asp Val Asp Ser His Gly
            20                  25                  30

His Ile Phe Val Leu His Arg Ala Gly Arg Glu Trp Thr Gln Pro Phe
        35                  40                  45

Pro Ser Asp Pro Ile Ser Glu Pro Thr Val Phe Met Phe Ala Ala Asn
    50                  55                  60

Gly Lys Leu Leu Ser Lys Trp Gly Ala Gly Glu Leu Val Met Pro His
65                  70                  75                  80

Gly Leu Ser Ile Asp Gly Asp Asn Lys Val Trp Ile Thr Asp Val Ala
                85                  90                  95

Arg Glu Gln Val Leu Arg Phe Thr His Glu Gly Ala Glu Glu Leu Val
                100                 105                 110

Leu Gly Thr Arg Gly Glu Thr Gly Gln Asp Glu Ser His Phe Gly Arg
            115                 120                 125

Pro Ala Asp Val Thr Phe Val Gly Asp Arg Val Leu Val Ala Asp Gly
    130                 135                 140

Tyr Leu Asn Arg Arg Ile Met Val Phe Asp Arg Ala Gly Asn Phe Leu
145                 150                 155                 160

Glu Gln Trp Gly Lys Glu Gly Glu Asp Ala Gly Glu Phe Asn Leu Pro
                165                 170                 175

His Ala Ile Ala Ala Asp Ser Glu Arg Ile Tyr Val Ala Asp Arg Glu
            180                 185                 190

Asn Ala Arg Val Gln Val Leu Ser Leu Asp Gly Glu Pro Leu Ala Arg
            195                 200                 205

Trp Arg Gln Asp Gly Thr Gly His Pro Tyr Ala Val Lys Pro Ile Gly
210                 215                 220

Ser Gly Tyr Val Leu Ala Ile Glu Gly Arg Asp Arg Ala Gly Arg Asn
225                 230                 235                 240

Thr Ala Ile Gly Arg Ile Tyr Arg Ala Asp Gly Gly Leu Glu Arg Val
                245                 250                 255

Phe Asp Ala Gly Val Glu Pro His Thr Gly Thr Ser Leu Gly His Asp
            260                 265                 270

Val Ala Ile Gly Pro Asp Gly Ser Ala Tyr Met Val Asp Asn Lys Ala
            275                 280                 285

Asn Arg Val Ile Lys Phe Asp Leu Ser Arg Ala Gly Val Glu Glu Ala
            290                 295                 300

Asp Ala Asp
305

<210> SEQ ID NO 14
<211> LENGTH: 13
<212> TYPE: PRT
<213> ORGANISM: ARTIFICIAL
<220> FEATURE:
<223> OTHER INFORMATION: synthetic

<400> SEQUENCE: 14

Ser Ser Ser Gly Gly Ser Gly Ser Glu Thr Leu Phe Gln
1               5                   10

<210> SEQ ID NO 15
<211> LENGTH: 310
<212> TYPE: PRT
<213> ORGANISM: Erythrobacter
```

<400> SEQUENCE: 15

```
Ala Arg Glu Glu Ala Pro Pro Val Thr Ile Asp Glu Ser Trp Pro Asp
1               5                   10                  15

Ile Pro Glu Ser Ala Val Phe Gly Pro Thr Ala Ile Asp Val Asp
            20                  25                  30

Ser His Gly His Ile Phe Val Leu His Arg Ala Gly Arg Glu Trp Thr
            35                  40                  45

Gln Pro Phe Pro Ser Asp Pro Ile Ser Glu Pro Thr Val Phe Met Phe
50                  55                  60

Ala Ala Asn Gly Lys Leu Leu Ser Lys Trp Gly Ala Gly Leu Val
65                  70                  75                  80

Met Pro His Gly Leu Ser Ile Asp Gly Asp Asn Lys Val Trp Ile Thr
                85                  90                  95

Asp Val Ala Arg Glu Gln Val Leu Arg Phe Thr His Glu Gly Ala Glu
            100                 105                 110

Glu Leu Val Leu Gly Thr Arg Gly Glu Thr Gly Gln Asp Glu Ser His
            115                 120                 125

Phe Gly Arg Pro Ala Asp Val Thr Phe Val Gly Asp Arg Val Leu Val
130                 135                 140

Ala Asp Gly Tyr Leu Asn Arg Arg Ile Met Val Phe Asp Arg Ala Gly
145                 150                 155                 160

Asn Phe Leu Glu Gln Trp Gly Lys Glu Gly Glu Asp Ala Gly Glu Phe
                165                 170                 175

Asn Leu Pro His Ala Ile Ala Ala Asp Ser Glu Arg Ile Tyr Val Ala
            180                 185                 190

Asp Arg Glu Asn Ala Arg Val Gln Val Leu Ser Leu Asp Gly Glu Pro
            195                 200                 205

Leu Ala Arg Trp Arg Gln Asp Gly Thr Gly His Pro Tyr Ala Val Lys
210                 215                 220

Pro Ile Gly Ser Gly Tyr Val Leu Ala Ile Glu Gly Arg Asp Arg Ala
225                 230                 235                 240

Gly Arg Asn Thr Ala Ile Gly Arg Ile Tyr Arg Ala Asp Gly Leu
                245                 250                 255

Glu Arg Val Phe Asp Ala Gly Val Glu Pro His Thr Gly Thr Ser Leu
            260                 265                 270

Gly His Asp Val Ala Ile Gly Pro Asp Gly Ser Ala Tyr Met Val Asp
            275                 280                 285

Asn Lys Ala Asn Arg Val Ile Lys Phe Asp Leu Ser Arg Ala Gly Val
290                 295                 300

Glu Glu Ala Asp Ala Asp
305                 310
```

<210> SEQ ID NO 16
<211> LENGTH: 9
<212> TYPE: PRT
<213> ORGANISM: ARTIFICIAL
<220> FEATURE:
<223> OTHER INFORMATION: synthetic

<400> SEQUENCE: 16

```
Ser Ser Ser Gly Gly Ser Gly Gly Ser
1               5
```

<210> SEQ ID NO 17
<211> LENGTH: 129
<212> TYPE: PRT

```
<213> ORGANISM: ARTIFICIAL
<220> FEATURE:
<223> OTHER INFORMATION: synthetic

<400> SEQUENCE: 17

Met Ala His Lys Lys Ser Gly Gly Val Ala Lys Asn Gly Arg Asp Ser
1               5                   10                  15

Leu Pro Lys Tyr Leu Gly Val Lys Val Gly Asp Gly Gln Ile Val Lys
            20                  25                  30

Ala Gly Asn Ile Leu Val Arg Gln Arg Gly Thr Arg Phe Tyr Pro Gly
        35                  40                  45

Lys Asn Val Gly Val Gly Arg Asp Phe Thr Leu Phe Ala Leu Lys Asp
    50                  55                  60

Gly Arg Val Lys Phe Glu Thr Lys Asn Asn Lys Lys Tyr Val Ser Val
65                  70                  75                  80

Tyr Glu Glu Ser Ser Ser Asp Asp Asp Lys Lys Cys Asn Thr Ala
                85                  90                  95

Thr Cys Ala Thr Gln Arg Leu Ala Asn Phe Leu His His Ser Ser Asn
            100                 105                 110

Asn Phe Gly Pro Ile Leu Pro Pro Thr Asn Val Gly Ser Asn Thr Tyr
        115                 120                 125

Gly

<210> SEQ ID NO 18
<211> LENGTH: 23
<212> TYPE: PRT
<213> ORGANISM: ARTIFICIAL
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa can be any naturally occurring amino acid
      except for Cys
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
      except for Cys
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(22)
<223> OTHER INFORMATION: Xaa can be any naturally occurring amino acid

<400> SEQUENCE: 18

Xaa Val Xaa Asp Arg Xaa Xaa Xaa Arg Xaa Gln Xaa Xaa Xaa Xaa Xaa
1               5                   10                  15

Gly Xaa Xaa Xaa Xaa Xaa Trp
            20
```

PEPTIDYL α-HYDROXYGLYCINE α-AMIDATING LYASES

CROSS-REFERENCE TO RELATED APPLICATIONS

This application is a 35 U.S.C. §371 national stage application of International Patent Application PCT/EP2010/068630 (published as WO2011/067283), filed Dec. 1, 2010, which claimed priority of European Patent Application 09177593.2, filed Dec. 1, 2009; this application further claims priority under 35 U.S.C. §119 of U.S. Provisional Application 61/266,711, filed Dec. 4, 2009.

FIELD OF THE INVENTION

The present invention relates to isolated polypeptides having peptidyl-α-hydroxyglycine alpha-amidating lyase activity, methods for preparing such polypeptides and the use of such polypeptides in processes for producing C-terminal α-amidated peptides.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on May 16, 2012. The Sequence Listing is made up of 26.3 kilobytes, and the information contained in the attached "SEQUENCE LISTING" is identical to the information in the specification as originally filed. No new matter is added.

BACKGROUND OF THE INVENTION

In multicellular organisms certain peptides ("precursors"), like neuropeptides, are post-translationally modified in a series of enzymatic steps that cleave and further modify peptide substrates to yield fully functional bioreactive peptides. The process begins in the trans-Golgi apparatus and continues as immature secretory granules. A very important late stage post-translational modification for many of these peptides is carboxyterminal alpha amidation.

Alpha-amidation of C-terminal residues is pivotal for the activity of several peptide hormones involved in the human or animal metabolism. Several peptide hormones are today used as drugs in the treatment of humans, e.g. for control of obesity and/or diabetes, or are under development as potential drugs. An example of such a peptide hormone is amylin (e.g. Symlin®, pramlintide acetate, which is an analogue of human amylin). Human amylin is a 37 amino acid residue peptide which can be used for treating or preventing obesity and/or diabetes. Accordingly, the C-terminal of amylin needs to be amidated in order to obtain full biological activity. Likewise Peptide YY (PYY) should be alpha amidated to obtain full biological activity.

E. coli, and yeast are widely used for recombinant expression of peptides of eukaryote origin. However, due to the nature of the C-terminal α-amide group peptide hormones cannot be expressed in an active form using state of art microbial expression systems based on E. coli and yeast, as alpha amidating enzymes are not expressed naturally in these organisms. Therefore a C-terminal alpha amide must be introduced in the recombinantly expressed peptides using for an example an ex vivo modification with alpha amidating enzymes.

Enzymatic modification of peptide precursors with a C-terminal Gly to α-amide by means of a bifunctional peptidyl α-amidating monooxygenase (PAM) is found in several eukaryotic organisms. Multiple alternatively spliced transcript variants encoding different isoforms have been described for this enzyme. The enzyme has exclusively been described for multicellular organisms (Metazoa). The conversion of C-terminal Gly residue in a peptide to α-amide is a two-step process, where the N-terminal domain of PAM (named PHM) catalyses the conversion of Glycine to α-hydroxyglycine and the C-terminal domain of PAM (named PAL) catalysis the conversion of the α-hydroxyglycine to α-amide. In eukaryotic organisms the two catalytic domains work sequentially to catalyze neuroendocrine peptides to active alpha-amidated products. Two disulphidebridges are highly conserved in PAL domains from eukaryotic organisms.

While it may be possible to synthesize by chemical means small peptides which contain an amide group at the C-terminal end (alpha amide), larger alpha-amidated peptides are difficult and expensive to produce. Alpha amidating enzymes are thus useful in the conversion of recombinant precursor peptides to mature peptides.

U.S. Pat. No. 4,708,934 describes a peptidyl-glycine α-amidating monooxygenase extracted from medullary thyroid carcinoma cell lines and tissue samples.

U.S. Pat. No. 5,789,234 describes the production of an alpha-amidating enzyme by recombinant DNA techniques.

WO90/08194 relates to a process for production of C-terminal alpha amidated peptide from a precursor peptide by the use of a eukaryotic C terminal alpha amidating enzyme. Also described is a method for eukaryotic expression of these C terminal alpha amidating enzymes.

WO89/02460 describes a bovine derived PAM enzyme, its cloning, cDNA and expression by recombinant DNA technology.

EP0448513 describes a process for recombinant expression of a peptidylglycine alpha-hydroxylating monooxygenase derived from Xenopus Laevis, comprising culturing insect cells transfected with a recombinant baculovirus to which a DNA coding for the peptidylglycine alpha-hydroxylating monooxygenase has been incorporated to produce the enzyme.

EP0465404 describes an enzyme (PHL; PAL) derived from Xenopus Laevis catalysing the cleavage of the N—C bond in the α-hydroxylglycine moiety of a C-terminally α-hydroxylated peptide, the cloning of the enzyme and its recombinant expression in insect cells.

US 20060292672 describes a cell line for expressing PAM or one of its two catalytic domains.

EP2172550 describes a recombinant C-terminal alpha-amidating enzyme derivative which lack the formation of at one of the five disulfide bonds normally occurring in a C-terminal alpha-amidating enzyme derived from Xenopus laevis and method of producing said derivative recombinantly in E. coli where the inclusions body obtained is solubilized and subjected to a refolding procedure.

SUMMARY OF THE INVENTION

The invention concerns novel enzymes, which are capable of catalysing the conversion of a α-hydroxyglycine to an α-amide in a peptide (peptidyl-α-hydroxyglycine alpha-amidating lyase activity).

The novel enzymes are derived from prokaryotic organisms and have different physicochemical and structural properties than described for eukaryotic PAL enzymes.

Accordingly, the invention provides enzymes having peptidyl-α-hydroxyglycine alpha-amidating lyase activity characterised in that they are derived from a prokaryotic organism.

The invention also provides enzymes having peptidyl-α-hydroxyglycine alpha-amidating lyase activity characterised in that they can be expressed in *E. coli* as soluble enzymatically active proteins.

The invention also provides enzymes having peptidyl-α-hydroxyglycine alpha-amidating lyase activity characterised in that they have an amino acid sequence comprising no cysteine residues, or at most 1 or at most 2 cysteine residues.

The invention also provides an enzyming having peptidyl-α-hydroxyglycine alpha-amidating lyase activity characterised in that it can be produced by a method comprising the steps of: (i) cultivating a recombinant an *Escherichia coli* strain host cell comprising a nucleic acid construct comprising a nucleotide sequence encoding the enzyme, under conditions suitable for the expression of the enzyme; and (ii) recovering the enzyme from the supernatant after host cell disruption and centrifugation.

Also provided are enzymes capable of catalysing the conversion of a α-hydroxyglycine to an α-amide in a peptide, wherein said enzyme has an amino acid sequence comprising the following motif (named motif 1): $Xaa_1$ Val $Xaa_2$ Asp Arg $Xaa_3$ $Xaa_4$ $Xaa_6$ Arg $Xaa_6$ Gln $Xaa_7$ $Xaa_8$ $Xaa_6$ $Xaa_{10}$ $Xaa_{11}$ Gly $Xaa_{12}$ $Xaa_{13}$ $Xaa_{14}$ $Xaa_{15}$ $Xaa_{16}$ Trp; where $Xaa_1$ to $Xaa_{16}$ are selected independently from a natural occurring amino acid, provided that $Xaa_1$ and $Xaa_7$ are not Cys.

Also provided are enzymes capable of catalysing the conversion of a α-hydroxyglycine to an α-amide in a peptide, wherein said enzyme has an amino acid sequence comprising the following motif (named motif 2): Asp Gly Tyr $Xaa_{17}$ Asn $Xaa_{18}$ Arg $Xaa_{19}$ $Xaa_{20}$ $Xaa_{21}$ Phe $Xaa_{22}$ $Xaa_{23}$ $Xaa_{24}$ Gly $Xaa_{25}$ $Xaa_{26}$ $Xaa_{27}$ $Xaa_{28}$ $Xaa_{29}$ $Xaa_{30}$ $Xaa_{31}$ $Xaa_{32}$ $Xaa_{33}$ Gly $Xaa_{34}$ $Xaa_{35}$ $Xaa_{36}$ Gly $Xaa_{37}$ Phe, where $Xaa_{17}$ to $Xaa_{37}$ are selected independently from a natural occurring amino acid, provided that $Xaa_{17}$ is not Cys.

Also provided are enzymes having peptidyl-α-hydroxylycine alpha-amidating lyase activity which comprises an amino acid sequence having at least 80% identity to the amino acid sequence selected from: (a) amino acids 2-306 of SEQ ID No. 1; (b) amino acids 3-336 of SEQ ID No. 2; (c) amino acids 3-305 of SEQ ID No. 3; (d) amino acids 3-279 of SEQ ID No. 4; (e) SEQ ID No. 19; (f) SEQ ID No. 20; (g) SEQ ID No. 21; (h) SEQ ID No. 22; and (i) SEQ ID No. 23.

The invention further provides the use of the enzymes of the invention in a process for preparing an α-amidated peptide by catalysing the conversion of a C-terminal α-hydroxyglycine residue to an α-amide residue in a peptide. Provided is also methods for producing an α-amidated peptide using the enzymes of the invention. Additionally the invention concerns a method for producing the enzymes of the invention by recombinant technology by providing an isolated nucleic acid encoding the enzyme of the invention, a vector comprising the nucleic acid, and a host cell.

Although expression levels are comparable the *Erythrobacter* PAL-like domain is expressed as highly soluble protein, in contrast to the rat PAL, which is insoluble and will require refolding to obtain a functional enzyme.

FIG. 3: A: FPLC chromatogram, showing SP Sepharose FF purification profile of RL9_THEMA tagged *Erythrobacter* PAL-like domain. The fusion protein elutes with a NaCl conc. of ~0.25 M indicated by arrow. Stippled line indicates conductivity curve, solid line indicate UV absorption signal at 280 nm. Numbers at X-axis indicates fractions and ml.

B: SDS-PAGE gel showing fractions from the main peak on the chromatogram from FIG. 3A. Apl: Application loaded onto the column, Ft: Flow through fractions. The TAP tag provides efficient capture and high purity after one cation exchange chromatography step.

FIG. 4A: FPLC chromatogram showing Q Sepharose HP separation of mature *Exiguobacterium* PAL-like domain released from RL9_THEMA tag following processing of fusion protein with HRV14 3C protease. A major peak elutes at ~0.4 M NaCl as indicated by arrow. Stippled line indicates conductivity curve, solid line indicate UV signal at 280 nm. Numbers at X-axis indicates fractions and ml.

FIG. 4B: SDS-PAGE analysis of eluted fraction from FPLC separation shown in FIG. 4A. Apl: Application loaded onto the column, Ft: Flow through fractions. In the application lane two bands representing the mature *Exiguobacterium* PAL-like domain (~30 kDa) and the released purification tag (~18 kDa). The major peak from the purification almost exclusively contains the mature PAL (solid arrow), whereas the released TAP tag does not bind the anion exchange column and is present in the flow through fraction (stippled arrow).

FIG. 5: UPLC analysis of synthetic α-hydroxy hippuric acid and benzamide representing α-hydroxyglycine (Gly (OH)) and α-amide (—NH2), respectively (marked below the relevant peaks). α-hydroxy hippuric acid was incubated with bacterial PAL-like enzymes with or without TAP tags in the N-terminal for 3 hours at 37° C., with the addition of relevant cofactors. Bold arrows points at the most significant enzymatic conversions to the benzamide.

Figure 2:
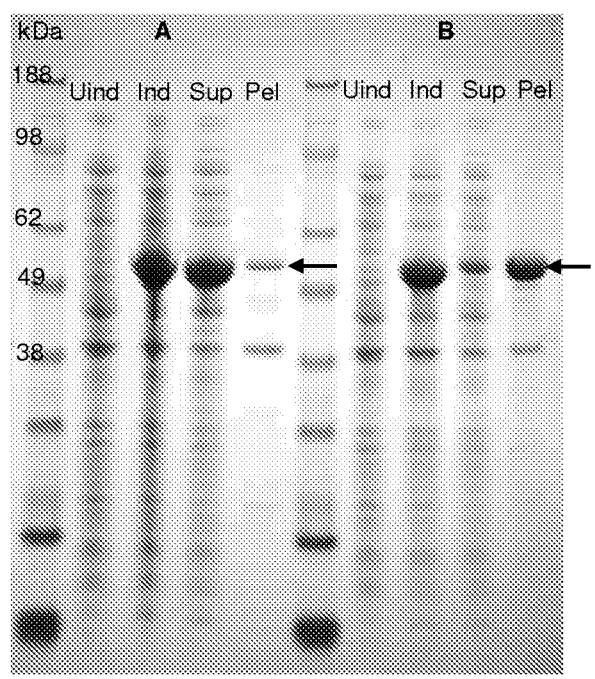
FIG. 2: SDS-PAGE showing the expression profile of RL9_THEMA TAP tagged *Erythrobacter* PAL-like domain (A) and rat PAL (B). Uind: Uninduced cell culture control (neg. control), Ind: After induction with 0.5 mM IPTG for 3 hours at 30° C., Sup: soluble fraction, Pel: Insoluble fraction. Arrow indicates molecular weight position of PAL bands on gels.

FIG. 5.A: Analysis of *Erythrobacter* PAL-like domain with (+TAP) (SEQ ID NO: 7) or without (−TAP) purification tag tested using acidic (MES pH 5.5) or basic (Tris pH 7.5) buffer conditions. Negative (neg.) control (ctrl) are the chromatograms for samples without addition of enzyme. Conversion of alphahydroxyhippuric acid to benzamide can occur spontaneously at high pH (FIG. 5A6/7) as previously described in literature. However, from the relative areas of α-hydroxy hippuric acid and benzamide substrate peak areas it is concluded that addition of enzyme can catalyze the conversion, most efficiently at pH 7.5 both with (FIG. 5A2/7) and without a TAP tag (FIG. 5A4/7).

Figure 1:
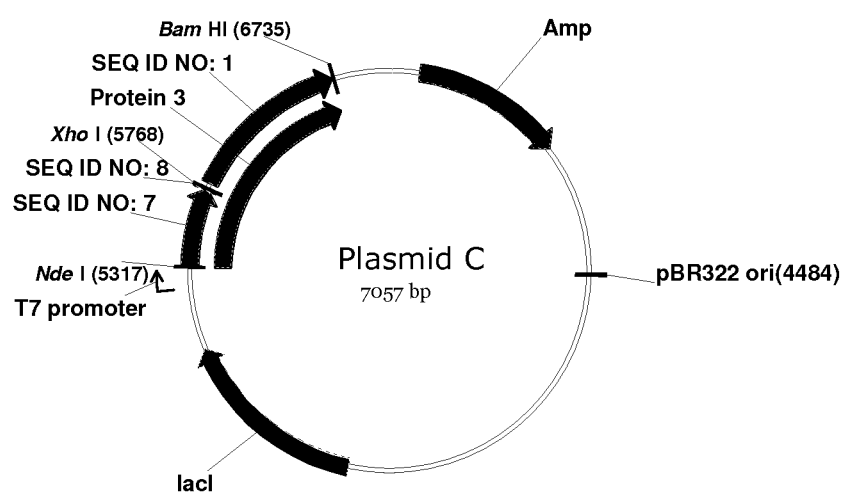
FIG. 1: Representative pET11a vector map of Plasmid C encoding bacterial PAL-like domain (without predicted signal peptides) from *Erythrobacter* (SEQ ID NO:1) with an N-terminal fusion partner (SEQ ID NO: 7) and a HRV14 3C protease cleavage site in the intervening linker region (SEQ ID NO: 8) (The entire fusion protein is marked with the feature Protein 3). NdeI, XhoI and BamHI restriction enzyme sites are depicted. T7 promoter region, Ampecillin resistance gene, lacI repressor region and origin of replication site are also shown in the vector map.

FIG. 5.B: Analysis of *Chthoniobacter* PAL-like domain with (+TAP) purification tag (SEQ ID NO: 7) tested using acidic (MES pH 5.5) or basic (Tris pH 7.5) buffer conditions. The *Chthoniobacter* enzyme is more active in the lower pH range compared to the *Erythrobacter* enzyme, as the benzamide peak area is significantly increased after incubation with the enzyme at pH 5.5 (FIG. 5B1/7) compared to the neg. ctrl. (FIG. 5B 3/7).

Figure 6:
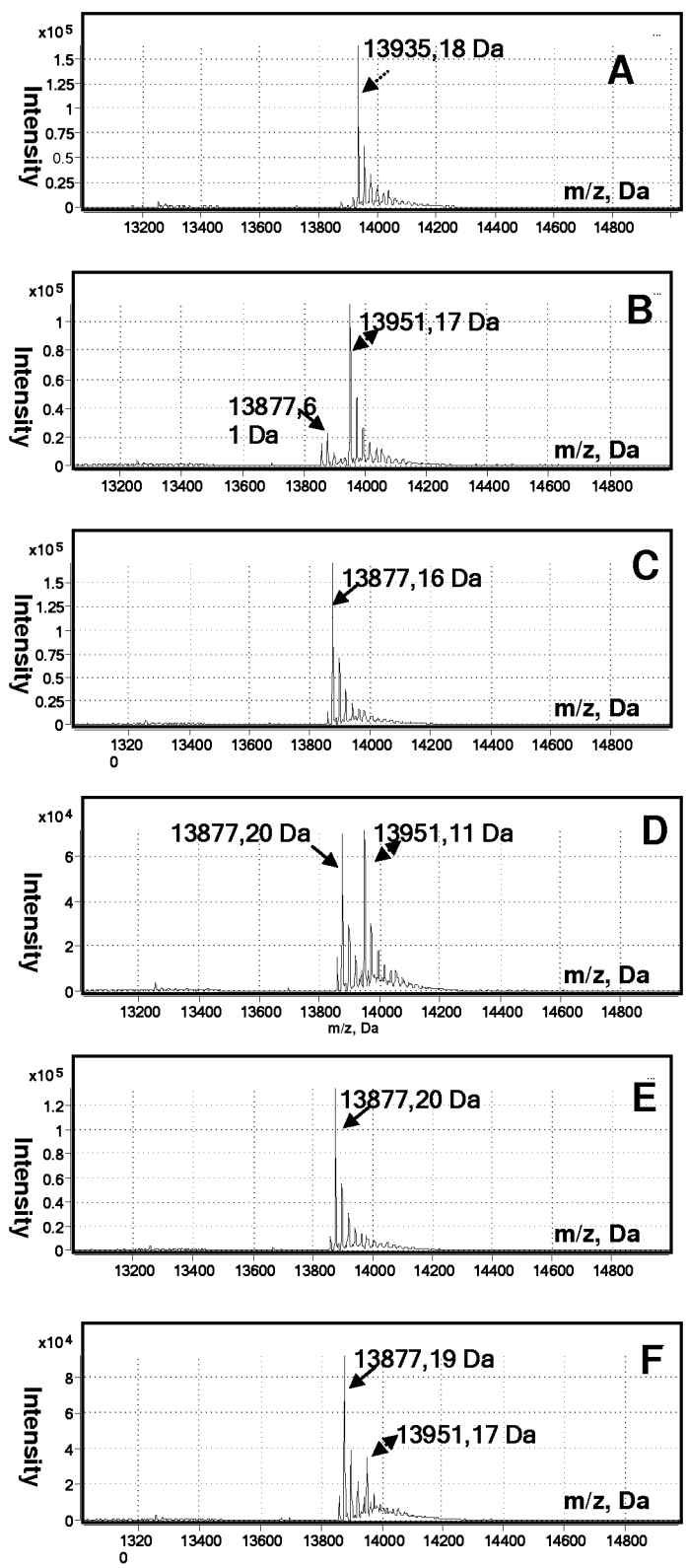

FIG. 6: Extracted and deconvoluted MS spectra of amylin analog model peptide confirming the PAL activity of bacterial PAL-like domains by co-incubations with rat PHM. X-axis: mass over charge ratios in Dalton. Y-axis: relative intensity of MS peaks. The masses of the prominent MS peaks are indicated in the spectrum; Precursor peptide control (containing a C-terminal Gly residue): 13934.66 Da, α-hydroxyglycine intermediate peptide (comprising a C-terminal α-hydroxyglycine): 13951 Da, α-amidated peptide: 13876.62 Da A: Untreated control, B: rat PHM alone (2 hours), C: *Planctomyces* PAL-like domain, protein 10 (2 hours), D: *Erythrobacter* PAL-like domain, protein 3 (2 hours), E: *Planctomyces* PAL-like domain, protein 10 (5 hours), F: *Erythrobacter* PAL-like domain, protein 3 (5 hours).

Figure 7D:
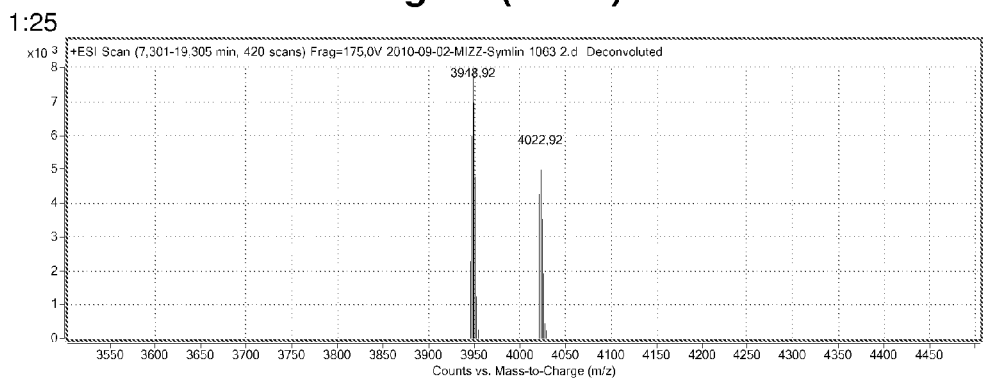

FIG. 7: Extracted and deconvoluted MS spectra of purified C-terminal alphahydroxy-glycine extended Pramlintide peptide incubated with four different bacterial PAL-like domains (SEQ ID NO: 1-4). X-axis: mass over charge ratios in Dalton. Y-axis: relative intensity of MS peaks. The masses of the two prominent MS peaks are indicated in the spectrum; α-hydroxyglycine intermediate peptide (comprising a C-terminal α-hydroxyglycine: ~4023 Da) peaks and α-amidated peptide (~3949 Da) peaks were all determined to be very close to the calculated average isotopic masses. Enzyme to substrate ratios (w/w) for each reaction is indicated.

A: *Erythrobacter* (SEQ ID NO: 1) i) PHM treated control (ctrl), ii) 1:1250, iii) 1:500, iv) 1:100

B: *Planctomyces* (SEQ ID NO: 4) i) PHM treated control (ctrl), ii) 1:1250, iii) 1:500, iv) 1:100.

C: *Chthoniobacter* (SEQ ID NO: 3) i) PHM treated control (ctrl), ii) 1:100, iii) 1:50, iv) 1:25.

D: *Exiquobacterium* (SEQ ID NO:2) i) PHM treated control (ctrl), ii) 1:100, iii) 1:50, iv) 1:25

DEFINITIONS

"PAM" or "peptidyl-glycine alpha-amidating monooxygenase" refers to the bifunctional enzyme catalyzing both conversions of a C-terminal Glycine residue to a α-hydroxyglycine and the conversion of a α-hydroxyglycine to an α-amide. The enzyme is also known as peptidylglycine 2-hydroxylase, peptidyl alpha-amidating enzyme, peptidylglycine alpha-hydroxylating monooxygenase and peptidyl-alpha-hydroxyglycine alpha-amidating lyase.

"PHM" or "peptidylglycine alpha-hydroxylating monooxygenase" is an enzyme, capable of catalysing the conversion of a C-terminal Glycine residue to a α-hydroxyglycine. Other terms for PHM are: peptidylglycine 2-hydroxylase, peptidylglycine alpha-amidating mono-oxygenase, peptidylglycine alpha-hydroxylase, peptidylglycine alpha-hydroxylating monooxygenase, peptidylglycine alpha-hydroxylating-monooxygenase, peptidylglycine alpha-monooxygenase, EC 1.14.17.3, and peptidylglycine monooxygenase.

As used herein "PAL enzyme", "PAL" or "peptidyl-α-hydrozyglycine alpha-amidating lyase" is an enzyme capable of catalysing the conversion of a α-hydroxyglycine to an α-amide. Synonyms for PAL are: Peptidylamidoglycolate lyase α-hydroxyglycine amidating dealkylase, HGAD, PGL, peptidylamidoglycolate peptidylamide-lyase, EC 4.3.2.5, and peptidylhydroxyglycine N—C lyase (PHL). The activity of the PAL enzyme can be demonstrated as described in Assay (I).

With "an enzyme capable of catalysing the conversion of a C-terminal α-hydroxyglycine to α-amide" is meant an enzyme which is capable of catalysing the reaction R-Gly (OH)→R—$NH_2$, where R is a peptide, a protein or a chemical compound.

As used herein the expression "an enzymes of the invention" means a polypeptide of the invention which has peptidyl-α-hydrozyglycine alpha-amidating lyase activity.

Nonpeptide substrates such as alpha-hydroxyhippuric acid also serve as substrates for PAL.

The term "PAL-like" is meant to denote an enzyme having the same activity as the known eukaryotic PAL enzyme.

By "target peptide" is meant the peptide, which is modified in an α-amidation process to obtain a C-terminal α-amide group. The target peptide should comprise a Gly residue in the C-terminal. The target peptide may be described as having the formula R'-X-Gly, where X represent any amino acid and where X is the amino acid to be converted to an amino acid amide, i.e. for which —COOH is to be converted to CO—$NH_2$ in the enzymatic α-amidation process reaction, R' represent a remaining portion of the peptide, and Gly represents a C-terminal glycine residue.

One example of a target peptide is a precursor of amylin, which in addition to the amylin sequence comprises a Gly residue in the C-terminal. Other non-limiting examples of Gly-extended peptide precursors relevant for the invention includes Neuropeptide Y (NPY), Peptide YY (PYY), PYY-3-36, Pancreatic polypeptide (PP), Glucagon like peptide (GLP-1), gastrin, calcitonin, calcitonin related peptide (CGRP), gastrin releasing peptide, vasopressin, oxytocin, neurokinin A, secretin, pancreastatin, pro-opiomelanocortin (POMC), alpha-melanocyte-stimulating hormone (alpha MSH), gamma-melanocyte-stimulating hormone (gamma 1MSH), and amidated hinge peptide (HP-N) or functional analogs thereof.

The term "isolated polypeptide" or "isolated polynucleotide" as used herein refers to a polypeptide or polynucleotide" that is isolated from its natural source.

A used herein, the terms "purified" or "recovered" refer to the removal of contaminants from a sample. For example, the PAL enzyme of the invention is purified by removal of contaminating proteins and other compounds within a solution or preparation. In some aspects the PAL enzyme of the invention is expressed using bacteria and these recombinant PAL enzymes are purified by the removal of other host cell constituents and the percentage of the recombinant PAL is thereby increased in the sample.

The term "substantially pure polypeptide" denotes herein a polypeptide preparation that contains at most 20%, at most 10% or at most at 5% by weight of other polypeptide material with which it is natively or recombinantly associated. It is, therefore, preferred that the substantially pure polypeptide is at least 80% pure, at least 90% pure or preferably at least 95% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

In one aspect "% Purity" is defined as the amount of the protein of interest divided by the amount of protein of interest+the amount of host cell contaminants×100. It may be determined by SDS-PAGE analysis or HPLC separations to determined amounts.

In one aspect, the polypeptide of the invention is at least 1% pure, e.g. at least 5% pure, at least 10% pure, at least 20% pure, at least 40% pure, at least 60% pure, at least 80% pure, at least 90% pure.

The term "recovered" or "recovering" as used herein for the polypeptide of the invention means in one embodiment that the polypeptide/enzyme is not associated with significant levels (e.g., at most 1%, at most 2%, at most 3%, at most 5%, at most 10% or at most 25%) of any extraneous and undesirable biological molecules contained within the system where the polypeptide was produced, e.g. a cell culture. A recovered polypeptide refers to a polypeptide of the invention that has passed through a stage of purity due to human intervention (whether automatic, manual, or both). It is understood that, within the invention is also recovered polypeptides of the invention and isolated polypeptides of the invention which is present in a composition. In other words, the term "recovered" or "isolated" is not meant to exclude artificial or synthetic mixtures with other compounds or materials.

The terms "protein", "peptide" and "polypeptide" are used interchangeably herein. Wherein a peptide is a portion of a protein, those skilled in the art understand the use of the term in context. The expressions "en enzyme of the invention" and "a polypeptide of the invention" are used interchangeably herein.

By "modification" of an amino acid sequence is meant a substitution, a deletion, and/or an addition (including insertions) of one or more amino acids in the sequence. In further aspects it also include replacements of one or more amino acid side chains.

The term "expression vector" is defined herein as a linear or circular DNA molecule that comprises a polynucleotide encoding a polypeptide of the present invention and is operably linked to additional nucleotides that provide for its expression. The term "plasmid", "expression vector" and "vector" are used interchangeably as the plasmid is the most commonly used form of vector at present. However the invention is intended to include such other forms of expression vectors that serve equivalent functions. As used herein "expression vector" or "vector" refers to a DNA construct containing a DNA sequence that is operably linked to a suitable control sequence capable of effecting the expression of the DNA in a suitable host. Such control sequences may, e.g., include a promoter to effect transcription, an optional operator sequence to control such transcription, a sequence encoding suitable mRNA ribosome binding sites and sequences which control termination of transcription and translation. The vector may, e.g., be a plasmid, a phage or simply a potential genomic insert. Once transformed into a suitable host, the vector may, e.g., replicate and function independently of the host genome, or may, in some instances, integrate into the genome itself.

The relatedness between two amino acid sequences is described by the parameter "identity" ("% identity"). Identity in the context of amino acid sequences of the invention can be determined by any suitable technique/programs, typically by a Needleman-Wunsch alignment analysis (see Needleman and Wunsch, J. Mol. Biol. (1970) 48:443-453) using the BLOSUM50 scoring matrix with an initial gap penalty of −12 and an extension penalty of −2. The output of Needle labeled "longest identity" (obtained using the -nobrief option) is used as the percent identity may be calculated as follows: (Identical Residues×100)/(Length of Alignment—Total Number of Gaps in Alignment). Because Needleman-Wunsch alignment provides an overall or global identity measurement between two sequences, it should be recognized that target sequences which may be portions or subsequences of larger peptide sequences may be used in a manner analogous to complete sequences or, alternatively, local alignment values can be used to assess relationships between subsequences, as determined by, e.g., a Smith-Waterman alignment (J. Mol. Biol. (1981) 147:195-197), which can be obtained through available programs. Other local alignment methods that may be suitable for analyzing identity include programs that apply heuristic local alignment algorithms such as FastA and BLAST programs.

When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence. The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

The term "nucleic acid molecule encoding", "nucleic acid sequence encoding", "DNA sequence encoding" and "DNA encoding" refer to the order or sequence of deoxyribonucleotides along a string of deoxyribonucleic acids. The order of these deoxyribonucleotides determines the order of amino acids along the protein chain. The DNA sequence thus encodes for the amino acid sequence of a protein, e.g. an enzyme. The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

The term "operably linked" denotes herein a configuration in which a control sequence is placed at an appropriate position relative to the coding sequence of the polynucleotide sequence such that the control sequence directs the expression of the coding sequence of a polypeptide. The term "expression" includes any step involved in the production of the polypeptide including, e.g., transcription, post-transcriptional modification, translation, post-translational modification, and secretion.

The term "derived from" as used herein in connection with deriving a polypeptide or a polynucleotide from a given source (i.e. a biological organism) means that the polynucleotide (the polynucleotide encoding the polypeptide) is identical to or a variant of a polynucleotide sequence naturally present in that source organism, irrespective if the polynucleotide sequence has been inserted into or the polypeptide is produced by another organism than the source organism. "Derived from" also means "identified from" in the context of the invention. "Derived from" in the context of the present invention also means identification of the enzymes of the invention from databases with bacterial nucleotide/protein sequences, i.e. by performing a computer assisted search in a protein databases, e.g. Uniprot, trEMBL, or Ref-SeqP.

By the term Wild type as used herein in the context of the present invention is meant the form (e.g. a gene or a protein sequence) as it occurs in nature. Also included are proteins being encoded by a nucleotide sequence deduced by searches in databases containing data of bacterial nucleotide/protein sequences. In one embodiment the term wild type includes the peptide sequence without signal peptide and leader peptide.

By the term "mature" as used herein (enzyme, polypeptide or amino acid sequence of the invention) is meant the putative minimal functional sequence of a polypeptide to which no natural or artificial amino acids extensions have been added (e.g. signal peptides or fusion partners).

The term "host cell", as used herein, includes any cell type that is susceptible to transformation, transfection, transduction, and the like with a nucleic acid construct or expression vector comprising a polynucleotide of the present invention.

The expression "purification tag" means a peptide sequence fused to an enzyme either at the N- or C-terminal end of the enzyme and is used for purifying the enzyme.

The expression "TAP" tag refers to a Thermostable Alkaline Protein tag derived from thermophilic bacteria, which when fused to the a peptide sequence of an enzyme either at the N- or C-terminal can be used to purifying the enzyme, as disclosed in international patent applications published under number WO 2006/108826 and WO 2008/043847.

The expression "fusion enzyme", "fusion protein" or "tagged enzyme" means an enzyme having a "fusion partner" attached to either the C-terminal or the N-terminal end of the enzyme. One example of a fusion partner is a protein tag, which may increase expression level, solubility or purification of the fusion protein.

With the expression "linker" is meant an amino acid sequence linking the fusion partner e.g. a purification tag and the enzyme together. The linker sequence may, e.g., comprise a sequence which promotes better folding of the target protein and/or a cleavage site for cleaving off the purification tag.

A "helix structure" is characterized by having an amino acid sequence which results in a coiled structure stabilized by interchain hydrogen bonds.

"% Solubility" is defined as the amount of soluble protein from host cell lysate divided by amount of soluble+insoluble protein from host cell lysate×100. It may be determined by SDS-PAGE analysis based comparison of insoluble and soluble fractions of cell lysates.

In the present context, the term "functional enzyme" is meant to indicate a protein with a similar function as the native enzyme. The protein may be structurally similar to the native enzyme and may be derived from the native enzyme by addition of one or more amino acids to either or both the C- and N-terminal end of the native enzyme, substitution of one or more amino acids at one or a number of different sites in the native amino acid sequence, deletion of one or more amino acids at either or both ends of the native enzyme or at one or several sites in the amino acid sequence, or insertion of one or more amino acids at one or more sites in the native amino acid sequence.

"Application" means a sample containing the enzyme which is loaded on a purification column. "Flow through" means the part of the application containing host cell proteins and contaminants which do not bind to the purification column. "Main peak" refers to the peak in a purification chromatogram which has the highest UV intensity and which contains the protein. "mAU" is milliabsorbance units. "UV 280" intensity" is the absorbance at a wavelength of 280 nm at which proteins will absorb, measured in milliabsorbance units. "IPTG" is isopropyl-β-D-thiogalactopyranoside. SDS-PAGE is sodium dodecylsulfate-polyacrylamide gel electrophoresis. FPLC (Fast protein liquid chromatography), is a form of liquid chromatography similar to high-performance liquid chromatography (HPLC) that is used to separate or purify proteins from complex mixtures. LC-MS (Liquid chromatography-mass spectrometry) is analytical technique that combines the physical separation capabilities of liquid chromatography (or HPLC) with the mass analysis capabilities of mass spectrometry.

Amino acids: In the present context the three-letter or one-letter indications of the amino acids have been used in their conventional meaning as indicated in table 1. Unless indicated explicitly, the amino acids mentioned herein are L-amino acids. Further, the left and right ends of an amino acid sequence of a peptide are, respectively, the N- and C-termini unless otherwise specified.

TABLE 1

Abbreviations for amino acids:

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

DETAILED DESCRIPTION OF THE INVENTION

Enzymatic modification of peptide precursors with a C-terminal Gly to an alpha-amidated peptide by means of a bifunctional peptidyl alpha-amidating monooxygenase (PAM) is found in several eukaryotic organisms. The natural substrates of PAM belonging to neurohormones or neurotoxins and the enzymes (PAM, PHM and PHL) involved in alpha amidation of peptides has exclusively been described for multicellular organisms (Metazoa). Organisms belonging to Bacteria or Archea has so far not been proven to posses polypeptides which can carry out the enzymatic steps needed to convert a C-terminal Gly to an alpha amide moiety in a peptide.

The eukaryotic PAL, PHM and PAM enzymes used for industrial in-vitro conversion of C-terminal Glycine extended peptide precursors to alpha amidated peptides has to be provided by recombinant expression in mammalian cell expression systems due to insufficient yield of active enzyme when expressed in other expression systems, such as, e.g. E. coli where they are expressed as insoluble proteins with the need of refolding.

Expression in mammalian cell expression systems give limited yield compared to expression in systems of bacterial, fungal or yeast origin. Further the sustainability of the expression processes in mammalian cells are limited, the culture time is often long with low expression yield per time unit. The expression of proteins in *E. coli* generally results in shorter fermentation cycles and yields per cell that are several factors larger compared to mammalian expression systems.

For the eukaryotic PAL, PHM or PAM enzymes it is difficult to design an economically sustainable process for providing high amounts of α-amidating enzyme for use in the industrial production of recombinant α-amidated peptides due to the need a mammalian cell expression system for production of correctly folded and active enzyme.

The eukaryotic PAM, PHM and PAL enzymes have many Cys residues as basis of their structural integrity and when these enzymes are expressed in the reducing cytosolic environment of *E. coli* cells they cannot form correct disulphide linkages as for the native enzymes. Kolhekar A. S et al. *Biochemistry* 2002, 41, 12384-12394 describes the characterization of the catalytical domain of rat PAL in terms of disulphide bridges. The two disulphide bridges in PAL are totally conserved between characterized PAL domains from eukaryots (p12388) indicating that the disulphide bridges are of importance the structural integrity of the enzyme. From Kolhekar A. S et al. *Biochemistry* 2002, 41, 12384-12394 it appears that reduction of the disulphide bridges with B-mercaptoethanol results in a reduction of enzymatic activity, thus supporting the structural importance of disulphide bridges in the eukaryotic PAL domains.

In WO90/08194 is described an attempt of enhancing the enzyme activity by treating an alpha amidating enzyme expressed in *E. coli* with a reducing agent such as dithiothreitol or 2-mercaptoethanol, in combination with a denaturating agent, and then oxidizing the reduced protein, but this method failed to enhance the enzyme activity.

EP2172550 describes a recombinant C-terminal alpha-amidating enzyme derivative which lack the formation of at least one of the five disulfide bonds normally occurring in a C-terminal alpha-amidating enzyme (PHM activity) derived from *Xenopus laevis* and method of producing said derivative recombinantly in *E. coli*.

The present invention as described herein provides novel enzymes (polypeptides of the invention), which are capable of catalysing the conversion of a α-hydroxyglycine to an α-amide. The novel enzymes of the invention are derived from a prokaryotic organisms and have different physicochemical properties and structural characteristics than described for eukaryotic PAL enzymes.

In particular is provided a sustainable way of producing α-amidating enzymes pivotal to the process economy of a recombinant process. The expression of the novel enzymes of the invention in *E. coli* results in higher final yields compared to mammalian expression PAM/PAL enzymes.

Characteristic of the enzymes of the invention is that they can be expressed in high yield as soluble proteins in *E. coli* and are very easy to handle in the downstream processing in contrast to their eukaryotic counterparts as they require no refolding to obtain activity.

Another important characteristic of the enzymes of the invention is that their activity are maintained despite fusion to N-terminal fusion partners. One example of these fusion partners is the TAP tags used in this invention, which allows easy purification of the enzymes and easy removal of the enzyme following the enzymatic step. Another example is the His6 tag. A number of TAP tagged enzymes were cloned and expressed *E. coli*. Thus, the enzymes according to the invention may be expressed in high yield as soluble TAP tagged fusion proteins in *E. coli* and are very easy to handle in the downstream processing in contrast to their eukaryotic counterparts.

Accordingly, the enzymes of the invention requires no potentially time-consuming and expensive refolding. Provided is thus a high yield production method of the enzymes in a non-mammalian host cell exemplified by *E. coli*.

In the following is described different aspects of the invention.

In one aspect of the invention the enzyme comprises the following motif 1: $Xaa_1$ Val $Xaa_2$ Asp Arg $Xaa_3$ $Xaa_4$ $Xaa_5$ Arg $Xaa_6$ Gln $Xaa_7$ $Xaa_8$ $Xaa_9$ $Xaa_{10}$ $Xaa_{11}$ Gly $Xaa_{12}$ $Xaa_{13}$ $Xaa_{14}$ $Xaa_{15}$ $Xaa_{16}$ Trp, where $Xaa_1$ and $Xaa_7$ can be any naturally occurring amino acid except for Cys and $Xaa_2$, $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$ can be any naturally occurring amino acid.

In one aspect $Xaa_4$ is Asn. In one aspect $Xaa_{14}$ is Leu. In one aspect $Xaa_7$ is Val or Ile. In one aspect $Xaa_8$ is Phe or Leu. In one aspect $Xaa_9$ is Asp or Ser.

In one aspect of the invention, the enzyme comprises the following motif 2: Asp Gly Tyr $Xaa_{17}$ Asn $Xaa_{18}$ Arg $Xaa_{19}$ $Xaa_{20}$ $Xaa_{21}$ Phe $Xaa_{22}$ $Xaa_{23}$ $Xaa_{24}$ Gly $Xaa_{25}$ $Xaa_{26}$ $Xaa_{27}$ $Xaa_{28}$ $Xaa_{29}$ $Xaa_{30}$ $Xaa_{31}$ $Xaa_{32}$ $Xaa_{33}$ Gly $Xaa_{34}$ $Xaa_{35}$ $Xaa_{36}$ Gly $Xaa_{37}$ Phe, where $Xaa_{17}$ to $Xaa_{37}$ are selected independently from a natural occurring amino acid, provided that $Xaa_{17}$ is not Cys.

Motif 1 is localised in a active site region and contains a Arg residue in a position similar to Arg706 in a active site region in rat (*Rattus norvegicus*) PAL. The amino acids in the region surrounding the Arg706 residue which is covered by Motif 1 shows limited sequence identity between rat PAL and the enzymes of the invention, but the Arg706 itself is being conserved in the characterized enzymes of the invention (SEQ ID NO 1-4). Chufan et al 2009 determined that the relative Vmax of rat PALcc R706A mutant was only 3% that of wild-type rat PALcc and shows that this residue is placed in the active site pocket, thus confirming the essential role of Arg706 (pp 969) for the enzymatic catalysis of PAL enzymes (Chufán E E, De M, Eipper B A, Mains R E, Amzel L M. Amidation of Bioactive Peptides: The Structure of the Lyase Domain of the Amidating Enzyme. Structure. 2009 Jul. 15; 17(7):965-73).

Motif 2 is localised in another active site region, which contains a Tyr residue in a position similar to Tyr654 in rat PAL, which is highly conserved and an essential residue for enzymatic catalysis as shown by mutagenesis and structural studies (De, M., Bell, J., Blackburn, N. J., Mains, R. E., and Eipper, B. A. (2006). Role for an essential tyrosine in peptide amidation. J. Biol. Chem. 281, 20873-20882.).

In one aspect the invention relates to an isolated polypeptide capable of catalysing the conversion of a α-hydroxyglycine to an α-amide, which polypeptide is selected from the group consisting of: a polypeptide comprising or consisting of an amino acid sequence having at least 70%, or at at least 75%, such as, e.g. of at least 80%, at least 85%, at least 90%, at least 95, at least 96%, or at least 98%, or 100% identity to the amino acid sequence selected from the group consisting of (a) amino acids 2-306 of SEQ ID NO:1; (b) amino acids 3-336 of SEQ ID NO:2; (c) amino acids 3-305 of SEQ ID NO:3; (d) amino acids 3-279 of SEQ ID NO:4; (e) SEQ ID NO: 13; (f) SEQ ID NO: 15; (g) SEQ ID NO:19; (h) SEQ ID NO:20; (i) SEQ ID NO:21; (j) SEQ ID NO:22; and (j) SEQ ID NO:23.

In one aspect the enzymes is derived from a prokaryotic organism, e.g. a bacterium.

In one aspect of the invention the enzyme is derived from *Burkholderia*, alpha *proteobacterium Methanosarcina, Sorangium, Mesorhizobium, Bradyrhizobium*, or *Solibacter* species.

In one aspect of the invention the enzyme is derived from an *Erythrobacter* species. In one aspect the enzyme is derived from an *Exiguobacterium* species. In one aspect the enzyme is derived from a *Chthoniobacter* species. In one aspect the enzyme is derived from a *Planctomyces* species.

In one aspect of the invention the enzyme is derived from an *Erythrobacter*, an *Exiguobacterium*, a *Chthoniobacter* or a *Planctomyces* species. In one aspect, the enzyme of the invention is derived from a prokaryotic organism selected from the group consisting of an *Erythrobacter*, an *Exiguobacterium*, a *Chthoniobacter* a *Planctomyces*, a *Burkholderia* species, an alpha *Proteobacterium*, a *Methanosarcina* species, a *Sorangium*, a *Salinispora* species, a *Mesorhizobium*, a *Bradyrhizobium*, and a *Solibacter* species.

In one aspect the enzyme is a wild type enzyme. In one aspect the polypeptide of the invention is the mature sequence without a signal peptide.

In one aspect the enzyme of the invention comprises up to 30 modifications compared to the wild type enzyme. In one aspect the enzyme comprises 1-30 modifications compared to the wild type enzyme. In one aspect the enzyme comprises 5-25 modifications compared to the wild type enzyme. In one aspect the enzyme comprises 10-20 modifications compared to the wild type enzyme. In one aspect the enzyme comprises 12-18 modifications compared to the wild type enzyme. In one aspect the number of modifications as described herein is compared to the mature wild type sequence.

In one aspect the enzyme of the invention comprises up to 30 modifications. In one aspect the enzyme comprises 1-30 modifications. In one aspect the enzyme comprises 5-25 modifications. In one aspect the enzyme comprises 10-20 modifications. In one aspect the enzyme comprises 12-18 modifications. It is understood that the sequences exemplified herein as being derived from a prokaryotic source can form the basis for such modifications (e.g. SEQ ID NO:1).

In one embodiment of the invention the enzyme is modified so at least one Cys residue is substituted or deleted for example by other suitable amino acid such as Ala, Ser or Val.

In one embodiment the polypeptide of the invention comprises a fusion partner.

One example of these fusion partners is a TAP tag, e.g. the TAP tags used in this invention, which allows easy purification of the enzymes and easy removal of the enzyme following the enzymatic step. Another example is a His tag, e.g His6 tag.

In one embodiment the enzyme according to the invention may comprise a purification tag. In one embodiment the enzyme according to the invention comprises a purification tag comprising a highly basic ribosomal protein derived from thermophilic bacteria as described in international patent applications published under number WO 2006/108826 and WO 2008/043847.

In embodiment the tag remains on the enzyme after purification.

In one embodiment of the invention the purification tag is immobilized metal affinity tags such as His6 or His8, Gluthathionine tranferase tags, tags recovered with antibodies such as FLAG tag, HA tag, MYC tag, biotin or streptavidin.

In one embodiment the tag will comprise a linker sequence which comprises a cleavage site for in vitro cleavage of the purification tag to give the enzyme.

In one embodiment of the invention the polypeptide of the invention comprises the fusion partner SEQ ID NO: 7 or SEQ ID NO: 11.

The linker may, e.g., have from 1-30, from 1-25, from 1-20 or from 1-15 amino acid residues and in one aspect the linker may comprise amino acid residues such as Leu, Pro and Ala, which increases alpha helix formation or other features resulting in structural rigidity. In another aspect the linker will comprise Gly and Ser residues, which gives flexibility to the linker In one embodiment the linker can be selected from the below group:

```
                                            (SEQ ID NO: 8)
Ser Ser Ser Gly Gly Ser Gly Ser Glu Val Leu Phe
Gln
                                            (SEQ ID NO: 9)
Ser Ser Ser Gly Ser Gly Glu Val Leu Phe Gln (SEQ ID NO: 10)
SER SER SER GLY GLY SER GLY GLY SER GLY (SEQ ID NO: 12)
Ser Ser Gly Gly Ser Gly Ser Glu Val Leu Phe Gln (SEQ ID NO: 14)
Ser Ser Ser Gly Gly Ser Gly Ser Glu Thr Leu Phe
Gln (SEQ ID NO: 16)
SER SER SER GLY GLY SER GLY GLY SER
```

The linker may be attached to either the C-terminal or the N-terminal end of the enzyme. The cleavage site may be any cleavage site which enables in vitro cleavage of the purification tag from the enzyme.

In one embodiment of the invention the enzyme comprises SEQ ID No. 1 and is capable of catalysing the conversion of a α-hydroxyglycine to an α-amide. In one aspect of the invention the enzyme comprises SEQ ID No. 2 and is capable of catalysing the conversion of a α-hydroxyglycine to an α-amide. In one aspect of the invention the enzyme comprises SEQ ID No. 3 and is capable of catalysing the conversion of a α-hydroxyglycine to an α-amide. In one aspect of the invention the enzyme comprises SEQ ID No. 4 and is capable of catalysing the conversion of a α-hydroxyglycine to an α-amide. In one aspect of the invention the enzyme comprises SEQ ID No. 13 and is capable of catalysing the conversion of a α-hydroxyglycine to an α-amide. In one aspect of the invention the enzyme comprises SEQ ID No. 15 and is capable of catalysing the conversion of a α-hydroxyglycine to an α-amide.

In one aspect of the invention the polypeptide of the invention comprises at most 2 cysteine residues. In one aspect of the invention the polypeptide of the invention comprises no cysteine residues. In one aspect of the invention the polypeptide of the invention comprises 1 cysteine residue.

In one aspect of the invention an α-amidation process is carried out in which the enzymes of the invention functions to catalyse the conversion a C-terminal α-hydroxyglycine of a target peptide to an α-amide.

In one aspect of the invention the enzyme of the invention is used in a process for preparing an α-amidated peptide.

In one aspect of the invention the first step of the α-amidation process is carried out by subjecting the protein to a enzyme with PHM activity and thereby allowing the C-terminal Gly residue to be converted to α-hydroxyglycine and then allowing the enzyme of the invention to catalyse the conversion of the α-hydroxyglycine to an α-amide.

Eukaryotic PHM activity is dependent on ascorbic acid and $Cu^{2+}$ and eukaryotic PAL activity is dependent on $Zn^{2+}$ and other divalent ions as cofactors. A similar dependency on $Zn^{2+}$ for activity was observed for the PAL like enzymes of the invention.

In one aspect of the invention, the α-amidation of a target peptide is carried out by a process comprising the steps of: i) subjecting a target peptide having a C-terminal Gly residue to an enzyme with PHM activity with the addition of $Cu^{2+}$ and/or ascorbic acid thereby allowing the C-terminal Gly residue of the peptide to be converted to α-hydroxyglycine; and ii) allowing an enzyme of the invention to catalyse the conversion of the α-hydroxyglycine to the α-amide of said peptide, wherein the reaction with said PHM and said enzyme of the invention on said peptide is performed either in two separate steps or simultaneously, In one aspect of the invention, the α-amidation of a target peptide is carried out by a process comprising the steps of i) subjecting a target peptide with a C-terminal Gly residue to an enzyme with PHM activity under conditions such that the PHM enzyme convert the C-terminal Gly residue to α-hydroxyglycine; and ii) using an enzyme of the invention to catalyse the conversion of the α-hydroxyglycine to the α-amide of said peptide. In one aspect the target peptide is subjected to an enzyme with PHM activity in the presence of $Cu^{2+}$ and/or ascorbic acid. In one aspect the target peptide is subjected to and enzyme with PHM activity and an enzyme of the invention at the same time. In one aspect, the target peptide is subjected to an enzyme with PHM activity and the enzyme of the invention at the same time and in the presence of $Cu^{2+}$ and/or ascorbic acid.

In one aspect the enzyme or the invention is capable of converting α-hydroxyhippuric acid to benzamide. The activity of the enzyme can be demonstrated by measuring the conversion of α-hydroxyhippuric acid to benzamide as described in Katopodis A G et al, Biochemistry. 1990, 29(26): 6115-6120 or as described in Assay (I).

In one aspect of the invention the enzyme is used in a process for preparing an α-amidated peptide. The biological activity of certain peptides is significantly increased when the peptides are α-amidated at the C-terminal. Examples of target peptides which benefit from being α-amidated at the C-terminal are amylin, Neuropeptide Y (NPY), Peptide YY (PYY), PYY-3-36, Pancreatic polypeptide (PP), gastrin, calcitonin, calcitonin related peptide (CGRP), gastrin releasing peptide, vasopressin, oxytocin, neurokinin A, secretin, pancreastatin, pro-opiomelanocortin (POMC), alpha-melanocyte-stimulating hormone (alpha MSH), gamma-melanocyte-stimulating hormone (gamma 1MSH), and amidated hinge peptide (HP-N).

In one aspect the peptide target is a C-terminal Gly-extended precursor of amylin or functional analogs thereof. In one aspect the peptide target is a C-terminal Gly-extended precursor of GLP-1 or functional analogs thereof. In one aspect the peptide target is a C-terminal Gly-extended precursor of PYY or functional analogs thereof.

In one aspect of the invention the enzyme is used together with an enzyme with PHM activity.

In one aspect the enzyme is used together with an enzyme with PHM activity and in the presence of $Cu^{2+}$ and/or ascorbic acid.

When preparing the α-amidated peptide with the enzymes according to the invention, the enzymes are allowed to react with a precursor of the peptide, which precursor has a C-terminal Gly residue. The Gly residue can be converted to α-hydroxyglycine by an enzymatic process in the presence of ascorbic acid and/or $Cu^{2+}$. One example of an enzyme capable of converting Gly to α-hydroxyglycine is an enzyme with PHM activity. The enzymes according to the invention catalyses the conversion of the α-hydroxyglycine to the α-amide.

In one aspect, the α-amidated peptide is used for the preparation of a medicament, such as, e.g, for the treatment or prevention of obesity, hyperglycemia including stress induced hyperglycemia, type 2 diabetes, impaired glucose tolerance, type 1 diabetes, burns, operation wounds, other diseases or injuries where an anabolic effect is needed in the treatment, myocardial infarction, stroke, coronary heart disease, other cardiovascular disorders, treatment of critically ill diabetic and non-diabetic patients and polyneuropathy.

In another aspect, the α-amidated peptide is used as a medicament for delaying or preventing disease progression in type 2 diabetes.

In one aspect of the invention, the α-amidated peptide is for used as a medicament for the treatment or prevention of obesity, hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, stroke, coronary heart disease and other cardiovascular disorders is provided.

In a further aspect the invention is related to a method for the treatment or prevention of obesity, hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, coronary heart disease and other cardiovascular disorders, stroke, the method comprising administering to a patient in need of such treatment an effective amount for such treatment of an α-amidated peptide.

In one aspect the invention comprises a method for producing an α-amidated peptide comprising allowing a target peptide to react with an enzyme according to the invention and purifying the α-amidated peptide. In one aspect the method comprises the use of an enzyme with PHM activity.

In one aspect the method comprises selecting the target peptide from the group consisting of an amylin, a Neuropeptide Y (NPY), a Peptide YY (PYY), a PYY-3-36, a Pancreatic polypeptide (PP), a Glucagon like peptide (GLP-1), a gastrin, a calcitonin, a calcitonin related peptide (CGRP), a gastrin releasing peptide, a vasopressin, a oxytocin, a neurokinin A, a secretin, a pancreastatin, a pro-opiomelanocortin (POMC), an alpha-melanocyte-stimulating hormone (alpha MSH), a gamma-melanocyte-stimulating hormone (gamma 1MSH), and an amidated hinge peptide (HP-N) or functional analogs thereof.

In one aspect of the invention the invention concerns an isolated nucleic acid encoding the enzyme of the invention. In one aspect there is provided a recombinant nucleic acid comprising a promoter and the said isolated nucleic acid.

In one aspect said recombinant nucleic acid is provided, wherein the nucleic acid further encodes a purification tag.

In one aspect there is provided a vector comprising the said recombinant nucleic acid. In one aspect there is provided a host cell comprising the said recombinant nucleic acid. In one aspect of the invention the recombinant nucleic acid is present in the genome of the host cell or in a vector that autonomously replicates in the host cell.

In one embodiment the host cell is mammalian, such as, e.g. CHO cells. One embodiment the host cell is a non-mammalian host cell. In one aspect a bacteria, a fungus e.g. yeast is used as a host cell for the production of the polypeptide of the invention. Suitable host cells are, e.g species of

*Escherichia*, e.g. *E. coli*, *Bacillus*, *Saccharomyces*, e.g. *Saccharomyces cerevisiae*, or *Pichia*. In one aspect the host cell is *E. coli*.

In one aspect of the invention there is provided a method for producing an enzyme of the invention capable of catalysing the conversion of α-hydroxyglycine to an α-amide comprising maintaining a host cell of the invention as described herein under conditions suitable for the production of the enzymes according to the invention.

One embodiment of the invention relates to a method for producing an enzyme with peptidyl-α-hydroxyglycine alphaamidating lyase (PAL) activity comprising the steps of: (i) cultivating a recombinant expression host cell of non-mammalian origin, which comprises a nucleic acid construct comprising a nucleotide sequence encoding an enzyme of the invention as described herein under conditions suitable for the expression of the enzyme; and (ii) recovering the enzyme from (a) the supernatant after cell disruption and centrifugation and/or (b) the growth media; wherein the host cell is a of non-mammalian origin, e.g. an *Escherichia coli* strain, and wherein the enzyme is soluble when recovered in step (ii). In one embodiment the enzyme is in a catalytically active form when recovered in step (ii) such that the enzyme does not require a step of refolding for obtaining catalytic activity (PAL like activity as described herein). Accordingly, within the invention is a method for production of the polypeptide of the invention, e.g. in *E. coli*, which does not comprise a step of refolding the polypeptide. In one aspect the polypeptide of the invention produced in a recombinant host cell as described herein, e.g. *E. coli*, is a least 50% or at least 80% soluble, i.e. without the need of refolding for obtaining catalytic activity.

In one aspect the host cell is *E. coli*, which comprises a vector comprising a recombinant nucleic acid encoding the enzyme of the invention, a purification tag and a promoter and the host cell is kept under conditions suitable for the production of the said enzymes.

In one aspect the enzyme is purified from the fermentation broth by the use of one cationexchange chromatographic step resulting in a purity of about 80%, e.g. of at least 80%.

In *E. coli* the majority of abundant proteins are found in a pl cluster ranging from pl 4-7 and 8-10 in which the majority of the proteins as well as the most abundant proteins are found in the pl 4-7 range. The TAP tags which may be used to purify the enzymes of the invention are highly alkaline and will when fused to an enzyme significantly increase the overall positive charge and pl of the enzyme so that it is clearly distinguished from the major bulk of host cell contaminants. This will allow the enzyme to be eluted at salt concentrations or at a pl at which the host cell contaminants will not be able to bind to a given cation exchange matrix. In one embodiment the purification tag has a pl above about 9, e.g. above 9. In one embodiment the purification tag has a pl above about 10, i.e. above 10. In one embodiment the pl of the purification tag will be between about 9 and about 12.5, i.e. in the range of 9-12.5 and in a further aspect the pl is about 10, ie. the pl is 10.

Any suitable cation exchange matrix can be used in the method according to the invention and a non limiting list of suitable cation exchange column material is: SP-Sepharose XL Amersham cat no 17-5073-01; Streamline SP XL Amersham cat no 17-5076-01; Streamline Direct CST Amersham cat no 17-5266-03; Obelix SP Amersham cat no 11-0010-86; 5-Support Unosphere, BioRad cat no 156-0113; SP-Sepharose High Performance Amersham cat no 17-1087-03; Source30S Amersham cat no 17-1273-02 and Toyopearl SP650S Toso-Haas cat no 08437

The TAP tags will contribute differently to the overall charge of a specific enzyme depending on the pl and charge of the chosen purification tag. Thus, purification of a specific target protein can be optimized by choosing a purification tag which enables elution of the fusion protein at a salt concentration or at a pH at which only minimal amounts of the host cell contaminants will co-elute.

The amino acid residues in the linker can be selected from such amino acid residues which will provide a less flexible structure to the tagged enzyme. Hereby the interference between the enzyme and the purification tag may be minimized. In one embodiment, the linker may comprise structural elements such as alpha helix structure.

The expressed tagged enzyme produced by the cells may be recovered from the culture medium by conventional procedures including separating the host cells from the medium by centrifugation or filtration, releasing the fusion protein by mechanical cell disruption, such as ultrasonication or pressure, precipitating the proteinaqueous components of the supernatant or filtrate by means of a salt, e.g. ammonium sulphate. After a cation-exchange chromatography capture step, the tagged enzyme may be eluted in a salt gradient and eluate fractions containing the fusion protein were collected.

A polypeptide of the invention expressed as an un-tagged enzyme may be recovered by means of purification such as, e.g., anion exchange chromatography, hydrophobic interaction chromatography and gel filtration chromatography (see, for example, Scopes, R., Protein Purification, Springer-Verlag, N.Y., 1982).

Purity of the polypeptide of the invention may, e.g., be evaluated by analyzing Coomasie stained PAGE gels using gel image analysis software or analysis of HPLC UV 214 nm chromatograms.

After the first purification step the purification tag can be cleaved off directly with a suitable processing enzyme (e.g. EK). If the salt concentration is too high the enzyme may be desalted before cleavage. The cleavage site can be any cleavage site which will enable efficient in vitro cleavage after isolating the purified enzyme. The most commonly used enterokinase cleavage site has the sequence DDDDK, where cleavage occurs after K. Other non-limiting processing enzymes cleavage sites include the Factor Xa cleavage site, which is most commonly IEGR, where cleavage occurs after R; the thrombin cleavage site, which is most commonly LVPRG or LVPRGS where cleavage occurs after the R; the Tobacco etcs virus (TEV) protease cleavage site, which is most commonly ENLYFQG/S, where cleavage occurs after Q and the HRV14 3C protease cleavage site, which is most commonly LEVLFQ/GP where cleavage occurs after Q. Reference is made to patent application WO 2006/108826.

The steps following cleavage may include a further cation exchange column purification as in the first step. In such scenario the purification tag released by the processing enzyme will have an extremely high pl leading to very efficient binding to the cation exchange matrix. The cleaved enzyme can now be collected in the flow through from the column, whereas the cleaved off purification tag and remaining highly charged contaminants from the production cell line will be retained on the cation exchange column.

Purification steps following cleavage may also comprise other means of purification such as anion exchange chromatography, hydrophobic interaction chromatography and gel filtration chromatography (see, for example, Scopes, R., Protein Purification, Springer-Verlag, N.Y., 1982).

In one aspect of the invention the enzyme is purified to at least about 90 to 95% homogeneity (i.e. to 90 to 95% homogeneity), to at least about 98% homogeneity (i.e. to 98% homogeneity). Purity may be assessed by e.g. gel electrophoresis, amino acid analysis or other HPLC based methods.

The recombinant nucleic acid encoding the enzyme with or without tag may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesised, e.g. in an automatic DNA synthesiser, purified, annealed, ligated and cloned in suitable vectors. The DNA sequences encoding the enzyme with or without tag may also be prepared by polymerase chain reaction such as splicing by overlap extension PCR using specific primers, for instance as described in U.S. Pat. No. 4,683,202, Saiki et al., Science 239 (1988), 487-491, or Sambrook et al., supra.

Furthermore, the recombinant nucleic acid may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The DNA sequences encoding the enzyme are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the enzyme is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide of the invention, such as, e.g. as a fusion protein.

Expression vectors for use in expressing the enzyme will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for directing the transcription of the DNA in mammalian cells are the SV40 promoter (Subramani et al., Mol. Cell Biol. 1 (1981), 854-864), the MT-1 (metallothionein gene) promoter (Palmiter et al., Science 222 (1983), 809-814), the CMV promoter (Boshart et al., Cell 41:521-530, 1985) or the adenovirus 2 major late promoter (Kaufman and Sharp, Mol. Cell. Biol, 2:1304-1319, 1982).

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4-c (Russell et al., Nature 304 (1983), 652-654) promoters.

Examples of suitable promoters for use in filamentous fungus host cells are, for instance, the ADH3 promoter (McKnight et al., The EMBO J. 4 (1985), 2093-2099) or the tpiA promoter. Examples of other useful promoters are those derived from the gene encoding A. oryzae TAKA amylase, Rhizomucor miehei aspartic proteinase, A. niger neutral alpha-amylase, A. niger acid stable alpha-amylase, A. niger or A. awamori glucoamylase (gluA), Rhizomucor miehei lipase, A. oryzae alkaline protease, A. oryzae triose phosphate isomerase or A. nidulans acetamidase. Preferred are the TAKA-amylase and gluA promoters. Suitable promoters are mentioned in, e.g. EP 238 023 and EP 383 779.

Examples of suitable promoters for use in bacterial host cells include the promoter of the Bacillus stearothermophilus maltogenic amylase gene, the Bacillus licheniformis alpha-amylase gene, the Bacillus amyloliquefaciens BAN amylase gene, the Bacillus subtilis alkaline protease gen, or the Bacillus pumilus xylosidase gene, or the phage Lambda $P_R$ or $P_L$ promoters or promoters used for expression in E. coli eg. lac, trp, phoA, araBAD, tac, bacteriophage T7 and cspA.

The vector may also comprise a selectable marker, e.g. a gene product which complements a defect in the host cell, such as the gene coding for dihydrofolate reductase (DHFR) or the Schizosaccharomyces pombe TPI gene (described by P. R. Russell, Gene 40, 1985, pp. 125-130), or a marker gene which confers resistance to a drug, e.g. ampicillin, kanamycin, tetracyclin, chloramphenicol, neomycin, hygromycin or methotrexate. For filamentous fungi, selectable markers include amdS, pyrG, argB, niaD and sC.

The DNA sequences encoding the enzyme may also, if necessary, be operably connected to a suitable terminator, such as the human growth hormone terminator (Palmiter et al., Science 222, 1983, pp. 809-814) or the TPI1 (Alber and Kawasaki, J. Mol. Appl. Gen. 1, 1982, pp. 419-434) or ADH3 (McKnight et al., The EMBO J. 4, 1985, pp. 2093-2099) terminators. Expression vectors may also contain a set of RNA splice sites located downstream from the promoter and upstream from the insertion site for the polypeptide sequence itself, such as, e.g. as a fusion protein. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nucl. Acids Res. 9:3719-3730, 1981). The expression vectors may also include a non coding viral leader sequence, such as the adenovirus 2 tripartite leader, located between the promoter and the RNA splice sites; and enhancer sequences, such as the SV40 enhancer.

To direct the enzyme into the secretory pathway of the host cells, a secretory signal sequence (also known as a leader sequence, prepro sequence or pre sequence) may be provided in the recombinant vector. The secretory signal sequence is joined to the DNA sequences encoding the enzyme in the correct reading frame. Secretory signal sequences are commonly positioned 5' to the DNA sequence encoding the peptide. The secretory signal sequence may be that, normally associated with the enzyme or may be from a gene encoding another secreted protein.

For secretion from yeast cells, the secretory signal sequence may encode any signal peptide, which ensures efficient direction of the expressed polypeptides into the secretory pathway of the cell. The signal peptide may be naturally occurring signal peptide, or a functional part thereof, or it may be a synthetic peptide. Suitable signal peptides have been found to be the alpha-factor signal peptide (cf. U.S. Pat. No. 4,870,008), the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897), the yeast BAR1 signal peptide (cf. WO 87/02670), or the yeast aspartic protease 3 (YAP3) signal peptide (cf. M. Egel-Mitani et al., Yeast 6, 1990, pp. 127-137).

For efficient secretion in yeast, a sequence encoding a leader peptide may also be inserted downstream of the signal sequence and upstream of the DNA sequence encoding the polypeptides. The function of the leader peptide is to allow the expressed peptide to be directed from the endoplasmic reticulum to the Golgi apparatus and further to a secretory vesicle for secretion into the culture medium (i.e. exportation of the polypeptides across the cell wall or at least through the cellular membrane into the periplasmic space of the yeast cell). The leader peptide may be the yeast alpha-factor leader (the use of which is described in e.g. U.S. Pat. Nos. 4,546,082, 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral alpha-amylase, *A. niger* acid-stable amylase, or *A. niger* glucoamylase. Suitable signal peptides are disclosed in, e.g. EP 238 023 and EP 215 594.

The host cell into which the DNA encoding the enzyme is introduced may be any cell which is capable of producing the present enzyme and includes bacteria, yeast, fungi and higher eukaryotic cells.

Examples of bacterial host cells which, on cultivation, are capable of producing the polypeptide of the invention are gram positive bacteria such as strains of *Bacillus*, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of *Streptomyces*, such as *S. lividans* or *S. murinus*, or gramnegative bacteria such as strains of *Echerichia coli*. The transformation of the bacteria may be effected by protoplast transformation or by using competent cells in a manner known per se (cf. Sambrook et al., supra).

Examples of suitable yeasts cells include cells of *Saccharomyces* spp. or *Schizosac-charomyces* spp., in particular strains of *Saccharomyces cerevisiae* or *Saccharomyces kluyveri*. Methods for transforming yeast cells with heterologous DNA and producing heterologous polypeptides there from are described, e.g. in U.S. Pat. Nos. 4,599,311, 4,931, 373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. Further examples of suitable yeast cells are strains of *Kluyveromyces*, such as *K. lactis*, *Hansenula*, e.g. *H. polymorpha*, or *Pichia*, e.g. *P. pastoris* (cf. Gleeson et al., J. Gen. Microbiol. 132, 1986, pp. 3459-3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae, A. nidulans* or *A. niger*. The use of *Aspergillus* spp. for the expression of proteins is described in, e.g., EP 272 277, EP 238 023, EP 184 438 The transformation of *F. oxysporum* may, for instance, be carried out as described by Malardier et al., 1989, Gene 78: 147-156. The trans-formation of *Trichoderma* spp. may be performed for instance as described in EP 244 234.

When a filamentous fungus is used as the host cell, it may be transformed with the recombinant nucleic acid of the invention, conveniently by integrating the nucleic acid in the host chromosome to obtain a recombinant host cell. This integration is generally considered to be an advantage as the recombinant nucleic acid is more likely to be stably maintained in the cell. Integration of the recombinant nucleic acid into the host chromosome may be performed according to conventional methods, e.g. by homologous or heterologous recombination.

The transformed or transfected host cell is then cultured in a suitable nutrient medium under conditions permitting expression of the enzyme after which all or part of the resulting enzyme may be recovered from the culture, e.g. the untagged enzyme. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

The invention is further summarized in the following paragraphs (embodiments):

1a. An isolated polypeptide capable of catalysing the conversion of a α-hydroxyglycine to an α-amide, wherein said polypeptide has an amino acid sequence comprising the following motif 1:

$Xaa_1$ Val $Xaa_2$ Asp Arg $Xaa_3$ $Xaa_4$ $Xaa_5$ Arg $Xaa_6$ Gln $Xaa_7$ $Xaa_8$ $Xaa_9$ $Xaa_{10}$ $Xaa_{11}$ Gly $Xaa_{12}$ $Xaa_{13}$ $Xaa_{14}$ $Xaa_{15}$ $Xaa_{16}$ Trp;

where $Xaa_1$, $Xaa_2$, $Xaa_3$, $Xaa_4$, $Xaa_5$, $Xaa_6$, $Xaa_7$, $Xaa_8$, $Xaa_9$, $Xaa_{10}$, $Xaa_{11}$ $Xaa_{12}$, $Xaa_{13}$, $Xaa_{14}$, $Xaa_{15}$, and $Xaa_{16}$ ($Xaa_1$ to $Xaa_{16}$) are selected independently from a natural occurring amino acid, provided that $Xaa_1$ and $Xaa_7$ are not Cys.

2a. The polypeptide of paragraph 1a, wherein $Xaa_4$ is Asn.

3a. The polypeptide of paragraph 1a or 2a, wherein $Xaa_{14}$ is Leu

4a. The polypeptide of any of paragraphs 1a-3a, wherein $Xaa_7$ is Val or Ile.

5a. The polypeptide of any of paragraphs 1a-4-a, wherein $Xaa_8$ is Phe or Leu.

6a. The polypeptide of any of paragraphs 1a-5a, wherein $Xaa_9$ is Asp or Ser.

7a. The polypeptide of paragraph 1a, wherein $Xaa_4$ is Asn, $Xaa_{14}$ is Leu, $Xaa_7$ is Val or Ile, $Xaa_8$ is Phe or Leu and $Xaa_9$ is Asp or Ser.

8a. An isolated polypeptide capable of catalysing the conversion of a α-hydroxyglycine to an α-amide, wherein said polypeptide has an amino acid sequence comprising the following motif 2: Asp Gly Tyr $Xaa_{17}$ Asn $Xaa_{18}$ Arg $Xaa_{19}$ $Xaa_{20}$ $Xaa_{21}$ Phe $Xaa_{22}$ $Xaa_{23}$ $Xaa_{24}$ Gly $Xaa_{25}$ $Xaa_{26}$ $Xaa_{27}$ $Xaa_{28}$ $Xaa_{29}$ $Xaa_{30}$ $Xaa_{31}$ $Xaa_{32}$ $Xaa_{33}$ Gly $Xaa_{34}$ $Xaa_{35}$ $Xaa_{36}$ Gly $Xaa_{37}$ Phe where $Xaa_{17}$, $Xaa_{18}$, $Xaa_{19}$, $Xaa_{20}$, $Xaa_{21}$, $Xaa_{22}$, $Xaa_{23}$, $Xaa_{24}$, $Xaa_{25}$, $Xaa_{26}$, $Xaa_{27}$, $Xaa_{28}$, $Xaa_{29}$, $Xaa_{30}$, $Xaa_{31}$, $Xaa_{32}$, $Xaa_{33}$, $Xaa_{34}$, $Xaa_{35}$, $Xaa_{36}$, $Xaa_{37}$ ($Xaa_{17}$ to $Xaa_{37}$) are selected independently from a natural occurring amino acid, provided that $Xaa_{17}$ is not Cys.

9a. The polypeptide of any of paragraphs 1a-8a, which polypeptide is derived from a prokaryotic organism.

10a. The polypeptide of paragraph 9a, wherein said prokaryotic organism is selected from the group consisting of an *Erythrobacter*, an *Exiguobacterium*, a *Chthoniobacter* and a *Planctomyces* species, or wherein said prokaryotic organism is selected from the group consisting of an *Erythrobacter*, an *Exiguobacterium*, a *Chthoniobacter* a *Planctomyces*, a *Burkholderia* species, an alpha *Proteobacterium*, a *Methanosarcina* species, a *Sorangium*, a *Salinispora* species, a *Mesorhizobium*, a *Bradyrhizobium*, and a *Solibacter* species.

11a. The polypeptide of paragraph 9a or 10a, wherein said polypeptide is a wild type sequence.

12a. The polypeptide of paragraph 11a, wherein said polypeptide is a mature sequence without a signal peptide.

13a. The polypeptide of any of paragraphs 1a-12a, wherein said polypeptide comprises 0, 1 or 2 cysteine residues.

14a. An isolated polypeptide capable of catalysing the conversion of a α-hydroxyglycine to an α-amide, which polypeptide is selected from the group consisting of:
(a) a polypeptide comprising or consisting of an amino acid sequence having at least 75% identity to amino acids 2-306 of SEQ ID NO: 1;
(b) a polypeptide comprising or consisting of an amino acid sequence having at least 75% identity to amino acids 3-336 of SEQ ID NO: 2,
(c) a polypeptide comprising or consisting of an amino acid sequence having at least 750% identity to amino acids 3-305 of SEQ ID NO: 3; and
(d) a polypeptide comprising or consisting of an amino acid sequence having at least 750% identity to amino acids 3-279 of SEQ ID NO: 4,
(e) a polypeptide comprising or consisting of an amino acid sequence having at least 75% identity to amino acids of SEQ ID NO: 13; and
(f) a polypeptide comprising or consisting of an amino acid sequence having at least 75% identity to amino acids of SEQ ID NO: 15.

15a. The polypeptide of paragraph 14a, which is a polypeptide comprising or consisting of an amino acid sequence having a degree of identity to amino acids 2-306 of SEQ ID NO:1 of at least 75%, such as, e.g. of at least 80%, at least 85%, at least 90%, at least 95, at least 96%, or at least 98%.

16a. The polypeptide of paragraph 14a, which is a polypeptide comprising or consisting of an amino acid sequence having a degree of identity to amino acids 3-336 of SEQ ID NO:2 of at least 75%, such as, e.g., of at least 80%, at least 85%, at least 90%, at least 95, at least 96%, or at least 98%.

17a. The polypeptide of paragraph 14a, which is a polypeptide comprising or consisting of an amino acid sequence having a degree of identity to amino acids 3-305 of SEQ ID NO:3 of at least 75%, such as of at least 80%, at least 85%, at least 90%, at least 95, at least 96%, or at least 98%.

18a. The polypeptide of paragraph 14a, which is a polypeptide comprising or consisting of an amino acid sequence having a degree of identity to amino acids 3-279 of SEQ ID NO:4 of at least 75%, such as, e.g., of at least 80%, at least 85%, at least 90%, at least 95, at least 96%, or at least 98%.

19a. The polypeptide of any of paragraphs 14a-18a, wherein said amino acid sequence comprises 0, 1 or 2 cysteine residues.

20a. The polypeptide of paragraph 1a in combination with any of paragraphs 14a-19a.

21a. The polypeptide of any of paragraphs 2a-12a in combination with any of paragraphs 14a-19a.

22a. The polypeptide of any of paragraphs 1a-13a, wherein said amino acid sequence comprises up to 30 modifications compared to a wild type amino acid sequence derived from a prokaryotic organism.

23a. The polypeptide of any of paragraphs 1a-13a, wherein said amino acid sequence comprises modifications in the range of 1-30 modifications, 1-25 modifications, 5-25 modifications, 1-20 modifications, 10-20 modifications, 1-12 modifications, 1-18 modifications, or 12-18 modifications compared to the amino acid sequence of a mature wild type PAL like enzyme derived from a prokaryotic organism.

24a. An isolated polypeptide capable of catalysing the conversion of a α-hydroxyglycine to an α-amide, which polypeptide is selected from the group consisting of:
(a) a polypeptide comprising or consisting of an amino acid sequence with modifications compared to amino acids 2-306 of SEQ ID NO: 1,
(b) a polypeptide comprising or consisting of an amino acid sequence with modifications compared to amino acids 3-336 of SEQ ID NO: 2,
(c) a polypeptide comprising or consisting of an amino acid sequence with modifications compared to 3-305 SEQ ID NO: 3, and
(d) a polypeptide comprising or consisting of an amino acid sequence with modifications compared to amino acids 3-279 SEQ ID NO: 4,
wherein said modifications are 1-30 amino modifications, 1-25 modifications, 5-25 modifications, 1-20 modifications, 10-20 modifications, 1-12 modifications, 1-18 modifications, or 12-18 modifications.

25a. The polypeptide of any of paragraphs 22a-24a, wherein said modification consist of one or more substitution(s), deletion(s), addition(s), including insertion (s), of one or more amino acids in the sequence, 26a. An isolated polypeptide selected from the group consisting of:
(i) An isolated polypeptide which is an enzyme capable of catalysing the conversion of a α-hydroxyglycine to an α-amide, characterised by the enzyme being derived from a prokaryotic organism,
(ii) An isolated polypeptide which is an enzyme capable of catalysing the conversion of a α-hydroxyglycine to an α-amide, wherein said polypeptide is characterized in that it is expressible in *E. coli* as a soluble protein,
(iii) An isolated polypeptide having peptidyl-α-hydroxyglycine alpha-amidating lyase activity characterised in that it can be expressed as a soluble protein in *E. coli*.
(iv) An isolated polypeptide having peptidyl-α-hydroxyglycine alpha-amidating lyase activity characterised in that it comprises 0, 1, or 2 cysteine residues,
(v) An isolated polypeptide having peptidyl-α-hydroxyglycine alpha-amidating lyase activity characterised in that it comprises no cysteine residues.

27a. The polypeptide of paragraph 26a(i), wherein the enzyme comprises up to 30 modifications compared to the wild type enzyme.

28a. The polypeptide of paragraphs 27a, wherein said amino acid sequence comprises modifications in the range of 1-30 modifications, 1-25 modifications, 5-25 modifications, 1-20 modifications, 10-20 modifications, 1-12 modifications, 1-18 modifications, or 12-18 modifications compared to the amino acid sequence of a mature wild type PAL like enzyme derived from said prokaryotic organism.

29a. An isolated polypeptide capable of catalysing the conversion of a α-hydroxyglycine to an α-amide, which polypeptide comprises or consist of the amino acid sequence 2-306 of SEQ ID NO. 1.

30a. An isolated polypeptide capable of catalysing the conversion of a α-hydroxyglycine to an α-amide, which polypeptide comprises or consist of the amino acid sequence 3-336 of SEQ ID NO. 2.

31a. An isolated polypeptide capable of catalysing the conversion of a α-hydroxyglycine to an α-amide, which polypeptide comprises or consist of the amino acid sequence 3-305 of SEQ ID NO. 3.

32a. An isolated polypeptide capable of catalysing the conversion of a α-hydroxyglycine to an α-amide, which polypeptide comprises or consist of the amino acid sequence 3-279 of SEQ ID NO. 4.

33a. An isolated polypeptide capable of catalysing the conversion of a α-hydroxyglycine to an α-amide, which polypeptide comprises or consist of the amino acid sequence SEQ ID NO. 13.

34a. An isolated polypeptide capable of catalysing the conversion of a α-hydroxyglycine to an α-amide, which polypeptide comprises or consist of the amino acid sequence SEQ ID NO. 15.

35a. An isolated polypeptide having peptidyl-α-hydrozyglycine alpha-amidating lyase activity which polypeptide is obtainable by a method comprising the steps of:
(i) cultivating a recombinant expression host cell of non-mammalian origin, which host cell comprises a nucleic acid construct comprising a nucleotide sequence encoding a polypeptide with peptidyl-α-hydroxyglycine alpha-amidating lyase (PAL) activity, under conditions suitable for the expression of said polypeptide; and
(ii) recovering the polypeptide from (a) the supernatant after cell disruption and centrifugation and/or (b) the growth media,
wherein the host cell is a of non-mammalian origin, such as, e.g. an *Escherichia coli* strain, and wherein the polypeptide is soluble and in and active form when recovered in step (ii) meaning that the polypeptide does not require a step of refolding for obtaining catalytic activity.

36a. An isolated polypeptide having peptidyl-α-hydroxyglycine alpha-amidating lyase activity which polypeptide is obtainable by a method comprising the steps of:
(i) cultivating a recombinant expression host cell of non-mammalian origin, which host cell comprises a nucleic acid construct comprising a nucleotide sequence encoding a polypeptide with peptidyl-α-hydroxyglycine alpha-amidating lyase (PAL) activity, under conditions suitable for the expression of said polypeptide; and
(ii) recovering the polypeptide from (a) the supernatant after cell disruption and centrifugation and/or (b) the growth media,
wherein the host cell is of non-mammalian host, such as, e.g. an *Escherichia coli* strain.

37a. The polypeptide of paragraph 35a or 36a further characterised by paragraph 1a.

38a. The polypeptide of paragraph 35a or 36a further characterised by any of paragraphs 2a-14a.

39a. The polypeptide of paragraph 365 or 36a, wherein said polypeptide comprises 0, 1 or 2 cysteine residues.

40a. The polypeptide of paragraph 35a or 36a or 39a, which polypeptide is derived from a prokaryotic organism.

41a. The polypeptide of paragraph 40a, wherein said prokaryotic organism is selected from the group consisting of an *Erythrobacter*, an *Exiguobacterium*, a *Chthoniobacter* a *Planctomyces*, a *Burkholderia* species, an alpha *Proteobacterium*, a *Methanosarcina* species, a *Sorangium*, a *Mesorhizobium*, a *Bradyrhizobium*, a *Salinispora* species and a *Solibacter* species, preferably said prokaryotic organism is an *Erythrobacter*, an *Exiguobacterium*, a *Chthoniobacter* or a *Planctomyces* species, 42a. The polypeptide of paragraph 40a or 41a, wherein said polypeptide is a wild type sequence.

43a. The polypeptide of paragraph 42a, wherein said polypeptide is a mature wild type sequence not containing a signal peptide.

44a. The polypeptide of any of paragraphs 40a-43a, wherein said amino acid sequence of said polypeptide comprises modifications in the range of 1-30 modifications, 1-25 modifications, 5-25 modifications, 1-20 modifications, 10-20 modifications, 1-12 modifications, 1-18 modifications, or 12-18 modifications compared to the amino acid sequence of the mature wild type PAL like enzyme derived from said prokaryotic organism.

45a. The polypeptide of paragraph 44a wherein said modification consist of one or more substitution(s), deletion (s), addition(s), including insertion(s) of one or more amino acids in the sequence.

46a. The polypeptide of any of paragraphs 40a-43a, wherein said amino acid sequence has at least 80% identity, at least 85%, at least 90%, at least 95, at least 96%, or at least 98%. to the amino acid sequence of the mature wild type PAL like enzyme derived from said prokaryotic organism.

47a. The polypeptide of any of paragraphs 1a-46a, wherein the polypeptide is capable of converting α-hydroxyhippuric acid to benzamide.

48a. The polypeptide of any of paragraphs 1a-46a, wherein said α-hydroxyglycine is a C-terminal-α-hydroxyglycine of formula R-Gly(OH), where R is a peptide and Gly(OH) is an α-hydroxyglycine residue linked to the C-terminus of said peptide, and wherein said α-amide is of formula R—NH$_2$.

49a. The polypeptide of any of paragraphs 1a-46a, which polypeptide is a peptidyl-α-hydroxyglycine alpha-amidating lyase (PAL).

50a. The polypeptide of any of paragraphs 1a-49a, wherein the polypeptide comprises a fusion partner.

51a. The polypeptide of any of paragraphs 1a-49a, wherein the polypeptide comprises a TAP tag.

52a. The polypeptide of any of paragraphs 1a-49a, wherein the polypeptide comprises a purification tag, e.g. selected from the group consisting of immobilized metal affinity tags (His6 or His8), Gluthathionine tranferase tags, tags recovered with antibodies (FLAG tag, HA tag, MYC tag), biotin and streptavidin.

53a. The polypeptide of any of paragraphs 50a-52a, wherein the enzyme is attached to the fusion partner by a linker sequence.

54a. The polypeptide of paragraph 53a, wherein the linker sequence has from 1 to 30, from 1 to 25, from 1 to 20 or from 1 to 15 amino acids.

55a. The polypeptide of any of paragraphs 1a-54a, wherein said polypeptide is substantially pure.

56a. The polypeptide of any of paragraphs 1a-54a, wherein the polypeptide preparation: (i) contains at most 50%, or at most 10% or at most 5% by weight of other polypeptide material with which it is natively or recombinantly associated, or (ii) the polypeptide is at least 50% pure, least 90% pure or at least 95% pure by weight compared to other polypeptide material with which it is natively or recombinantly associated.

57a. The polypeptide of any of paragraphs 1a-54a, wherein said polypeptide is at least 5% pure, at least 10% pure, at least 25% pure, at least 50 pure, at least 75% pure, at least 80% pure, at least 90% pure compared to of other polypeptide material as determined by SDS-PAGE.

58a. An isolated polynucleotide comprising a nucleotide sequence that encodes the polypeptide of any of paragraphs 1a-57a or 73a.

59a. An isolated recombinant nucleic acid construct comprising the polynucleotide of paragraph 58a.

60a. The nucleic acid construct of paragraph 59a, wherein the nucleotide sequence is operably linked to one or more control sequences that direct the production of the polypeptide in an expression host.

61a. The nucleic acid construct of paragraph 60a or 61a comprising a promoter.

62a. The nucleic acid of any of paragraphs 59a-61a, wherein the nucleic acid further encodes a purification tag and/or a linker.

63a. A recombinant expression host cell comprising the nucleic acid construct of any of paragraphs 59a-62a.

64a. The host cell of paragraph 63a, wherein the recombinant nucleic acid is present in the genome of the host cell or in a vector that autonomously replicates in the host cell.

65a. The host cell of paragraph 63a or 64a, wherein the host cell is selected from the group consisting of: (i) a bacteria or a fungus, (ii) a yeast, (iii) a mammalian host cell, and (iv) a prokaryotic host cell.

66a. The host cell according to any of paragraphs 63a-65a, wherein the host cell is *E. coli*.

67a. A method for producing an enzyme capable of catalysing the conversion of α-hydroxyglycine to an α-amide comprising maintaining the host cell of any of paragraphs 63a-66a under conditions suitable for the production of said enzyme.

68a. A method of producing the polypeptide of any of paragraphs 1a-57a or 73a comprising (i) cultivating a host cell comprising a nucleic acid construct comprising a nucleotide sequence encoding said polypeptide under conditions conducive for production of the polypeptide; and (ii) recovering the polypeptide.

69a. The method of claim 68a wherein the polypeptide is recovered in a soluble form from the supernatant after cell disruption.

70a. A method for producing an enzyme with peptidyl-α-hydroxyglycine alpha-amidating lyase (PAL) activity comprising the steps of:
i) cultivating a recombinant expression host cell of non-mammalian origin which comprises a nucleic acid construct comprising a nucleotide sequence encoding the enzyme, under conditions suitable for the expression of the enzyme; and
ii) recovering the enzyme from
a) the supernatant after cell disruption and centrifugation and/or
b) the growth media wherein the host cell is of non-mammalian origin such as, e.g., an *Escherichia coli* strain and wherein the enzyme is soluble when recovered in step ii).

71a. The method of paragraph 70a, wherein the enzyme has an amino acid sequence comprising 0, 1 or 2 Cys residues.

72a. The method of paragraph 70a or 71a, wherein the enzyme is in a catalytically active form when recovered in step ii) meaning that the enzyme does not require a step of refolding for obtaining catalytic activity.

73a. An isolated polypeptide which is an enzyme with peptidyl-α-hydrozyglycine alpha-amidating lyase activity obtainable by the method of any of paragraph 70a-72a and wherein said enzyme is capable of catalysing the reaction: R-Gly(OH)→R—NH$_2$, where R is a peptide and Gly(OH) is an α-hydroxyglycine residue linked to the C-terminus of said peptide.

74a. Use of a polypeptide of any of paragraphs 1a-57a or 73a for catalysing the conversion of a C-terminal α-hydroxyglycine residue to an α-amide residue in a peptide.

75a. Use of paragraph 74a, wherein the polypeptide is used in a process for preparing an α-amidated peptide.

76a. Use of paragraph 74a or 75a, wherein Cu$^{2+}$ ions and/or ascorbic acid are present when using said polypeptide.

77a. Use of any of paragraphs 74a-76a, wherein an enzyme with PHM activity is used in the process for preparing an α-amidated peptide.

78a. A method for producing an α-amidated peptide comprising the steps of: (i) allowing a target peptide with a C-terminal glycine residue to react with both a peptidylglycine alpha-hydroxylating monooxygenase (PHM) and a polypeptide of any of paragraphs 1a-57a or 73a under conditions suitable for enzymatic activity, wherein the reaction with said PHM and said polypeptide on said target peptide is performed either in two separate steps or simultaneously; (ii) recovering the C-terminally α-amidated peptide.

79a. A method for producing an α-amidated peptide comprising
(i) producing a precursor (target peptide) of an amidated peptide by recombinant expression of the peptide in a prokaryotic host, wherein said precursor has a C-terminal Glu residue;
ii) treating said precursor with a PHM like enzyme to obtain a C-terminal α-hydroxyglycine of said peptide;
iii)) treating said C-terminal α-hydroxyglycine with a polypeptide of any of paragraphs 1a-57a or 73a
iv) recovering the C-terminal α-amidated peptide.

80a. The use or method of any of paragraphs 74a-79a, wherein the amino acid sequence of the enzyme with PHM is derived from a mammalian organism.

81a. The use or method of any of paragraphs 74a-80a, wherein the recovered α-amidated peptide is to be used as a medicament.

82a. The use or method of claim 81a, comprising a step (iii) of preparing a pharmaceutical formulation comprising the recovered C-terminally α-amidated peptide.

83a. The use or method of any of paragraphs any of paragraphs 74a-82a, wherein said target peptide is selected from the group consisting of amylin, Neuropeptide Y (NPY), Peptide YY (PYY), PYY-3-36, Pancreatic polypeptide (PP), Glucagon like peptide (GLP-1), gastrin, calcitonin, calcitonin related peptide (CGRP), gastrin releasing peptide, vasopressin, oxytocin, neurokinin A, secretin, pancreastatin, pro-opiomelanocortin (POMC), alpha-melanocyte-stimulating hormone (alpha MSH), gamma-melanocyte-stimulating hormone (gamma 1MSH), and amidated hinge peptide (HP-N) or functional analogs thereof.

84a. The use or method of any of paragraphs 74a-83a, where the α-amidated peptide is used for treating or preventing one of the following conditions and/or diseases: obesity, hypertension, hyperglycemia including stress induced hyperglycemia, type 2 diabetes, impaired glucose tolerance, type 1 diabetes, burns, operation wounds, other diseases or injuries where an anabolic effect is needed in the treatment, myocardial infarction, stroke, coronary heart disease, other cardiovascular disorders, treatment of critically ill diabetic and non-diabetic patients and polyneuropathy.

85a. An isolated polypeptide capable of catalysing the conversion of a α-hydroxyglycine to an α-amide, wherein said polypeptide has an amino acid sequence comprising the following motif (named motif 2): Asp Gly Tyr $Xaa_{17}$ Asn $Xaa_{18}$ Arg $Xaa_{19}$ $Xaa_{20}$ $Xaa_{21}$ Phe $Xaa_{22}$ $Xaa_{23}$ $Xaa_{24}$ Gly $Xaa_{25}$ $Xaa_{26}$ $Xaa_{27}$ $Xaa_{28}$ $Xaa_{29}$ $Xaa_{30}$ $Xaa_{31}$ $Xaa_{32}$ $Xaa_{33}$ Gly $Xaa_{34}$ $Xaa_{35}$ $Xaa_{36}$ Gly $Xaa_{37}$ Phe, where $Xaa_{17}$ to $Xaa_{37}$ are selected independently from a natural occurring amino acid, provided that $Xaa_{17}$ is not Cys 86a. The isolated polypeptide of paragraph 85a, which polypeptide is derived from a prokaryotic organism.

87a. The polypeptide of paragraph 85a or 86a, wherein said polypeptide comprises 0, 1 or 2 cysteine residues.

88a. The polypeptide of any of paragraphs 85a-87a, wherein said α-hydroxyglycine is a C-terminal-α-hydroxyglycine of formula R-Gly(OH), where R is a peptide and Gly(OH) is an α-hydroxyglycine residue linked to the C-terminus of said peptide, and wherein said α-amide is of formula R—$NH_2$.

89a. An isolated polypeptide having peptidyl-α-hydroxyglycine alpha-amidating lyase activity which polypeptide comprises or consist of the amino acid sequence SEQ ID NO: 19 (PNSQPNPYRTVEGWFQMPAGRTMGST-SAVFVAPGGHIWVAERCGANTCAGSDVAPL LEFDTAGKVVSSFGAGMFQFPHGIWIEP-DGSIWLTDGQGANGKGHQVFKFSPQGKVLM TLGKAGVAGDGPDTFNQPNAVAVSANGD-VFISDGHNAGRGNARVLKYSKDGTFIKQW GGHGSGPGQFEVPHTLAFDSKGR-LFVGDRANNRIQIFDQDGKFLDEWKQF-GRPSGIFI DRNDAMYVTDSESTDRDGYGHNPG-WKRGIRIGSAKDGSVTAFIPDPSPGAGATSAAEG VAADAKGNVYGAEVGPKDVKKYVRK, derived from *Solibacter* sp).

90a. An isolated polypeptide having peptidyl-α-hydroxyglycine alpha-amidating lyase activity which polypeptide comprises or consist of the amino acid sequence SEQ ID NO: 20 (TVSDPAVGAIPEDRLLRPWGRLPATARI-GTGITVGPTGEIALLHRAGTAFAYDAVIDTDT VVVLNPRDGTVRQTWGAGRFRSPHSI-TADSEGRYWVTDVSTNKITTFDAAGRQVGELG HDYPTGLETALRVRNVLSNLPCTLDEYI-FARPTDVAVSADGSIVVADGYRNSRVARFDT HRVLTGQWGELGDQPAQFNIPHGVALD-SNGAVYVADRRNARVQVFNADGSVRHVWH SSALGRPYDVAIGPDDAVYVLDGGDLL-DENNGEQRGYVCRLSTTGRVTHRWALADQR ANPHQLAIGVRGEIYVAALAGAPLWRWAPQ, derived from *Salinispora* sp).

91a. An isolated polypeptide having peptidyl-α-hydroxyglycine alpha-amidating lyase activity which polypeptide comprises or consist of the amino acid sequence SEQ ID NO: 21 (MLTSGHGMYITAQDDLFVVTYDAHQVL-HFDPNQELVKALGTFNEPHWEAPFNHPTDVA VGAEGDIYVADGYGNAQVHRFASDGSYL-NGWGTPGISAGEFSTPHAIWVLPDERVLW DRDNDRIQVFDRNGAVLDEWRGLVRPM-DIWADPEGQRIYVTEQAPRITCLDSAGVVIGR ARTFGIYPHGIWGAPDGSLYVAEQGYPH-QIVKYERI, derived from *Burkholdia* sp).

92a. An isolated polypeptide having peptidyl-α-hydroxyglycine alpha-amidating lyase activity which polypeptide comprises or consist of the amino acid sequence SEQ ID NO: 22 (MLPGPSVITDGQYRYHADQHWAK-LPAGQQFGPISQLAVDASNRVIWQRDTPAVLVFS HDGTLELAWHHPKLTSVHGLCVAP-DESLFIVSFDAHQVLKFSRSGELLLEL-GKFSSPNWI EPFNHPTDVAVANDGEIYVTDGYG-NARVHRFAADGTYIGGWGQHGNKTGEFSCPHGI WIDEDVGRVLAVDRDNDRVQVFDRS-GQYLSEWTGFRRPMDIWGTPNGTFYIVDQAPG LSIVDRNGRLRARARMYPTYSHGIG-GDANGNLFVAAQGPSRVVRLERLDNEE, derived from *Burkholdia* sp.).

93a. An isolated polypeptide having peptidyl-α-hydroxyglycine alpha-amidating lyase activity which polypeptide comprises or consist of the amino acid sequence SEQ ID NO: 23 QLGPSDAYRTTYGWEKMPAGRALGVSS-GVFPDRDGKHIWILARCGGNNCAGSDADPIL KFDMAGNLVTSFGKGVLAFPHGFFIDAE-GNVWVTEGAPVGDRRGDAGFKIGKGHQVFK FSPEGKLLMTLGVAGVAGDDNKHFNGPS-GVAIAPNGDIVVVVDGHRGGNNRVVRFSKD GKFIRAIGGGVGSESADTGRFSDPHGI-AIDSAGRIFVADRGNNRIQILDPEGNFLAEWKQ FGKPSGVYIDARDRIYVGDGMSTPERN-PGVVPGIRVGDAKTGKVTAFIPDNEKYKQGES GVEFLAADADGNIYAGEVTRQRFGKHIPLK.

94a. An isolated polypeptide having peptidyl-α-hydroxyglycine alpha-amidating lyase activity, which polypeptide comprises or consist of an amino acid sequence having a degree of identity to SEQ ID NO: 19 of at least 75%, such as of at least 80%, at least 85%, at least 90%, at least 95, at least 96%, or at least 98%.

95a. An isolated polypeptide having peptidyl-α-hydroxyglycine alpha-amidating lyase activity, which polypeptide comprises or consist of an amino acid sequence having a degree of identity to SEQ ID NO: 20 of at least 75%, such as of at least 80%, at least 85%, at least 90%, at least 95, at least 96%, or at least 98%.

96a. An isolated polypeptide having peptidyl-α-hydroxyglycine alpha-amidating lyase activity, which polypeptide comprises or consist of an amino acid sequence having a degree of identity to SEQ ID NO: 21 of at least 75%, such as of at least 80%, at least 85%, at least 90%, at least 95, at least 96%, or at least 98%.

97a. An isolated polypeptide having peptidyl-α-hydroxyglycine alpha-amidating lyase activity, which polypeptide comprises or consist of an amino acid sequence having a degree of identity to SEQ ID NO: 22 of at least 75%, such as of at least 80%, at least 85%, at least 90%, at least 95, at least 96%, or at least 98%.

98a. An isolated polypeptide having peptidyl-α-hydroxyglycine alpha-amidating lyase activity, which polypeptide comprises or consist of an amino acid sequence having a degree of identity to SEQ ID NO: 23 of at least 75%, such as of at least 80%, at least 85%, at least 90%, at least 95, at least 96%, or at least 98%.

99a. The polypeptide of any of paragraphs 89a-98a, wherein said amino acid sequence comprises 0, 1 or 2 cysteine residues.

100a. The polypeptide of any of paragraphs 85a-99a, wherein the polypeptide comprises a fusion partner.

101a. The polypeptide of any of paragraphs 85a-100a, wherein said polypeptide is capable of catalysing the conversion of a α-hydroxyglycine to an α-amide, where said α-hydroxyglycine is a C-terminal-α-hydroxyglycine of formula R-Gly(OH), where R is a peptide and Gly(OH) is an α-hydroxyglycine residue linked to the C-terminus of said peptide, and said α-amide is of formula R—NH$_2$.

102a. Use of a polypeptide defined in any of paragraphs 85a-101a in a use or a method as defined in any of paragraphs 74a-84a.

103a. An isolated polynucleotide comprising a nucleotide sequence that encodes the polypeptide of any of paragraphs 85a-101a.

104a. An isolated recombinant nucleic acid construct comprising the polynucleotide of paragraph 85a-101a.

105a. The nucleic acid construct of paragraph 104a, wherein the nucleotide sequence is operably linked to one or more control sequences that direct the production of the polypeptide in an expression host.

106a. The nucleic acid construct of paragraph 104a or 105a comprising a promoter.

107a. The nucleic acid of any of paragraphs 104a-106a, wherein the nucleic acid further encodes a purification tag and/or a linker.

108a. A recombinant expression host cell comprising the nucleic acid construct of any of paragraphs 104a-107a.

109a. The host cell of paragraph 108a, wherein the recombinant nucleic acid is present in the genome of the host cell or in a vector that autonomously replicates in the host cell.

110a. The host cell of paragraph 107a or 109a, wherein the host cell is selected from the group consisting of: (i) a bacteria or a fungus, (ii) a yeast, (iii) a mammalian host cell, and (iv) a prokaryotic host cell.

111a. The host cell according to any of paragraphs 108a-110a, wherein the host cell is *E. coli*.

The invention is further summarized in the following paragraphs:

1. An enzyme capable of catalysing the conversion of a α-hydroxyglycine to an α-amide, characterised by the enzyme being derived from a prokaryotic organism.
2. An enzyme according to paragraph 1, wherein the enzyme comprises the following motif: Xaa$_1$ Val Xaa$_2$ Asp Arg Xaa$_3$ Xaa$_4$ Xaa$_6$ Arg Xaa$_6$ Gln Xaa$_7$ Xaa$_8$ Xaa$_9$ Xaa$_{10}$ Xaa$_{11}$ Gly Xaa$_{12}$ Xaa$_{13}$ Xaa$_{14}$ Xaa$_{15}$ Xaa$_{16}$ Trp; where Xaa$_{16}$ and Xaa$_7$ can be any naturally occurring amino acid except for Cys and Xaa$_2$, Xaa$_3$, Xaa$_4$, Xaa$_6$, Xaa$_6$, Xaa$_8$, Xaa$_9$, Xaa$_{10}$, Xaa$_{11}$, Xaa$_{12}$, Xaa$_{13}$, Xaa$_{14}$, Xaa$_{15}$, Xaa$_{16}$ can be any naturally occurring amino acid.
3. An enzyme according to paragraph 2, wherein Xaa$_4$ can be Asn.
4. An enzyme according to paragraph 2 or 3, wherein Xaa$_{14}$ can be Leu.
5. An enzyme according to paragraphs 2-4, wherein Xaa$_7$ can be Val or Ile.
6. An enzyme according to paragraphs 2-5, wherein Xaa$_8$ is Phe or Leu.
7. An enzyme according to paragraphs 2-6, wherein Xaa$_9$ can be Asp or Ser.
8. An enzyme according to paragraphs 1-7, wherein the enzyme is isolated from *Erythrobacter, Exiguobacterium, Chthoniobacter* or *Planctomyces* species.
9. An enzyme according to paragraphs 1-3, wherein the enzyme is capable of converting α-hydroxyhippuric acid to benzamide.
10. An enzyme according to paragraphs 1-9, wherein the enzyme is a wild-type enzyme.
11. An enzyme according to paragraph 1-5, wherein the enzyme comprises up to 30 modifications compared to the wild type enzyme.
12. An enzyme according to paragraphs 1-11, wherein the enzyme comprises 1-30 modifications.
13. An enzyme according to paragraphs 1-12, wherein the enzyme comprises 5-25 modifications.
14. An enzyme according to paragraphs 1-13, wherein the enzyme comprises 10-20 modifications.
15. An enzyme according to paragraphs 1-14, wherein the enzyme comprises 12-18 modifications.
16. An enzyme according to paragraphs 1 and 11-15, wherein at least one Cys residue is substituted or deleted.
17. An enzyme according to paragraphs 1-16, wherein the enzyme comprises a fusion partner.
18. An enzyme according to paragraphs 1-17, wherein the enzyme comprises a TAP tag.
19. An enzyme according to paragraphs 1-17, wherein the enzyme comprises a purification tag selected from the group consisting of: immobilized metal affinity tags (His6 or His8), Gluthathionine tranferase tags, tags recovered with antibodies (FLAG tag, HA tag, MYC tag) biotin or streptavidin.
20. An enzyme according to paragraphs 17-19, wherein the enzyme is attached to the fusion partner by a linker sequence.
21. An enzyme according to paragraph 20, wherein the linker sequence has from 1 to 30, from 1 to 25, from 1 to 20 or from 1 to 15 amino acids.
22. An enzyme according to any of paragraphs 1-21, wherein Xaa$_4$ can be Asn, Xaa$_{14}$ can be Leu, Xaa$_7$ can be Val or Ile, Xaa$_8$ is Phe or Leu and Xaa$_9$ can be Asp or Ser.
23. An enzyme comprising SEQ ID No. 1, which enzyme is capable of catalysing the conversion of a α-hydroxyglycine to an α-amide
24. An enzyme comprising SEQ ID No. 2, which enzyme is capable of catalysing the conversion of a α-hydroxyglycine to an α-amide.
25. An enzyme comprising SEQ ID No. 3, which enzyme is capable of catalysing the conversion of a α-hydroxyglycine to an α-amide.
26. An enzyme comprising SEQ ID No. 4, which enzyme is capable of catalysing the conversion of a α-hydroxyglycine to an α-amide.
27. An enzyme comprising SEQ ID No. 13, which enzyme is capable of catalysing the conversion of a α-hydroxyglycine to an α-amide.
28. An enzyme comprising SEQ ID No. 15, which enzyme is capable of catalysing the conversion of a α-hydroxyglycine to an α-amide.
29. An enzyme according to paragraphs 23-27, wherein the enzyme comprises 1-30 modifications.
30. An enzyme according to paragraphs 23-28, wherein the enzyme comprises 5-25 modifications.
31. An enzyme according to paragraphs 23-29, wherein the enzyme comprises 10-20 modifications.
32. An enzyme according to paragraphs 23-30, wherein the enzyme comprises 12-18 modifications.

33. An enzyme according to paragraphs 23-31, wherein at least one Cys residue is substituted or deleted.
34. Use of an enzyme according to any of paragraphs 1-33 for catalysing the conversion of a C-terminal α-hydroxyglycine to an α-amide in a peptide.
35. Use according to paragraph 34 in a process for preparing an α-amidated peptide.
36. Use according to paragraphs 34-35, wherein $Cu^{2+}$ ions and/or ascorbic acid are present.
37. Use according to paragraphs 34-36, wherein an enzyme with PHM activity is used in the process for preparing an α-amidated peptide.
38. Use according to paragraphs 34-37, wherein the peptide is a target peptide selected from the group consisting of amylin, NPY, PYY-3-36, PP, GLP-1, gastrin, calcitonin, gastrin releasing peptide, vasopressin, oxytocin, neurokinin A, secretin, POMC, alpha MSH, gamma 1MSH, and HP-N or functional analogs thereof.
39. Use according to paragraphs 34-38, wherein the α-amidated peptide is used for treating or preventing on of the following conditions: obesity, hypertension, hyperglycemia including stress induced hyperglycemia, type 2 diabetes, impaired glucose tolerance, type 1 diabetes, burns, operation wounds, other diseases or injuries where an anabolic effect is needed in the treatment, myocardial infarction, stroke, coronary heart disease, other cardiovascular disorders, treatment of critically ill diabetic and non-diabetic patients and polyneuropathy.
40. A method for producing an α-amidated peptide comprising allowing a target peptide to react with an enzyme according to paragraphs 1-33 and purifying the α-amidated peptide.
41. A method according to paragraph 40, wherein an enzyme with PHM activity is used in the method.
42. A method according to paragraphs 40-41, wherein the target peptide is selected from the group consisting of amylin, NPY, PYY-3-36, PP, GLP-1, gastrin, calcitonin, gastrin releasing peptide, vasopressin, oxytocin, neurokinin A, secretin, POMC, alpha MSH, gamma 1 MSH, and HP-N or functional analogs thereof.
43. An isolated nucleic acid encoding the enzyme of any of paragraphs 1-33.
44. A recombinant nucleic acid comprising:
   a. A promoter
   b. The isolated nucleic acid of paragraph 43.
45. A recombinant nucleic acid according to paragraph 44, wherein the nucleic acid further encodes a purification tag.
46. A recombinant nucleic acid according to paragraphs 44-45, wherein the nucleic acid further encodes a linker.
47. A vector comprising the recombinant nucleic acid of paragraphs 44-46.
48. A host cell comprising the recombinant nucleic acid of paragraphs 44-46.
49. The host cell of paragraph 48, wherein the recombinant nucleic acid is present in the genome of the host cell or in a vector that autonomously replicates in the host cell.
50. The host cell according to paragraphs 48-49, wherein the host cell is a bacteria, a fungus e.g. a yeast.
51. The host cell according to paragraphs 48-50, wherein the host cell is *E. coli*.
52. A method for producing an enzyme capable of catalysing the conversion of α-hydroxyglycine to an α-amide comprising maintaining the host cell of paragraph 47 under conditions suitable for the production of said enzyme.

EXAMPLES

All examples of enzymes of the invention identified by use of databases and the characterizations below, contained a signal peptide predicted with high confidence using Signal P (Henrik Nielsen et al., "Identification of prokaryotic and eukaryotic signal peptides and prediction of their cleavage sites" Protein Engineering 10, 1-6 (1997)). As the signal peptide is normally not part of the mature functional enzyme these were removed from the original sequence according the prediction. The enzymes in examples 1-6 described below was designed with a GlyPro N-terminal extension to facilitate removal of the TAP fusion partner with a HRV14 3C protease that recognizes the sequence GluValLeuPheGln/GlyPro.

Example 1

Cloning of Fusion Proteins with Ribosomal Protein L9 as Purification Tag and PAL-like Domain from *Erythrobacter* sp. SD-21

Four sequence variants of the *Erythrobacter* PAL-like domain were cloned, expressed and evaluated. The variants were made to evaluate whether different fusion partners, linkers or extension to the N-terminal of the PAL-like domain affected expression and solubility.

Protein 1:

SEQ ID NO:13 encodes a PAL-like domain derived from the *Erythrobacter* sp. SD-21 bacterium. The molecular weight of the protein was calculated to 33467.1 Da. When fused to a Thermostable Alkaline Protein (TAP) purification tag (SEQ ID NO: 7) via a Gly/Ser-rich flexible linker (SEQ ID NO: 10) the fusion enzymes will have a molecular weight of 51231.7 Da and represent protein 1 as described in table 1.

To obtain plasmid A encoding protein 1, a XhoI/BamHI gene fragment encoding SEQ ID NO:13 was codon optimized for expression in *E. coli* and obtain as a synthesized gene fragment with 5' end XhoI and 3' end BamHI cloning sites (GeneScript). In the 5'-end a short fragment encoding the linker (SEQ ID NO: 10) partner was introduced directly upstream of the nucleotide fragment encoding the PAL-like domain (SEQ ID NO: 13).

The XhoI/BamHI fragment was ligated into a pET11a (Novagen) expression vector already encoding a purification tag comprised in a NdeI/XhoI fragment (Ribosomal Protein L9 from *T. maritima*, described in international patent applications published under number WO 2006/108826 and WO 2008/043847 (SEQ ID NO 7) using the LigaFast™ Rapid Ligation System (Promega) by methods described by the manufacteror. The ligation products were used to transform TOP10 (Invitrogen) competent *E. coli* cells and incubated overnight on LB (Luria-Bertani) medium with 150 micrograms per milliter Ampicillin agar plates. Plasmid A encoding the fusion protein of interest were obtained from culture positive clones following plasmid propagation in liquid medium and standard minipreperations of plasmids. Correct nucleotide sequence of plasmid A was verified by DNA sequencing with T7 promoter/terminator sequence specific primers.

Protein 2:

Another variant of the *Erythrobacter* sp. SD-21 PAL-like domain (plasmid B) were obtained by ligating a ~110 bp XhoI/NcoI synthetic fragment (Geneart) comprising minor changes in the linker region and N-terminal part of the *Erythrobacter* PAL-like domain into a XhoI/NcoI site in the plasmid A, thus giving rise to the protein 2. Protein 2 comprises the same purification tag SEQ ID NO 7 as described for protein 1, but has a linker with a HRV14 3C protease cleavage site (ELTFQ) (SEQ ID NO: 14) and changes in the N-terminal of the PAL-like domain (SEQ ID NO: 15). The theoretical molecular weight of the fusion protein is 52092.6 Da and 33823.5 Da for the HRV14 3C protease released PAL-like domain.

Protein 3:

Another variant of the *Erythrobacter* PAL-like domain (plasmid C, examplified on vector map in FIG. 1) were obtained by ligating a XhoI/NcoI synthetic fragment (Geneart) comprising minor changes in the linker region and N-terminal part of the *Erythrobacter* PAL-like domain into a XhoI/NcoI site in the plasmid B, thus giving rise to the protein 3. Protein 3 comprises the SEQ ID NO 7 purification tag, but has a slightly modified linker (SEQ ID NO: 8) allowing cleavage with HRV14 3C protease compared to protein 2 and a PAL-like *Erythrobacter* domain truncated by 4 amino acids (SEQ ID NO: 1) compared to protein 2 and one amino acid compared to protein 1 and comprising a N-terminal Gly residue (SEQ ID NO: 1). The theoretical molecular weight of the fusion protein is 51591.1 Da and 33324 Da for the HRV14 3C protease released PAL-like domain.

Cloning of Fusion Protein with His6 Purification Tag and PAL-Like Domain from *Erythrobacter* sp. SD-21

Protein 4

Another variant of the *Erythrobacter* sp. SD-21 PAL-like domain SEQ ID NO: 1 was obtained by exicising a XhoI/BamHI fragment from vector C and ligating this fragment into a vector comprising the fusion partner encoding a consecutive SEQ ID NO: 9 and 10 sequence to obtain plasmid D. The encoded fusion protein comprises an N-terminal Histidine 6 tag (SEQ ID NO:9) and a linker with HRV14 3C protease cleavage site (SEQ ID NO: 12) in front of the *Erythrobacter* PAL-like domain SEQ ID NO: 1 and has a theoretical molecular weight of 35645.4 Da.

Cloning of Eukaryotic PAL Domains for Comparative Analysis

In order to compare novel PAL-like domains from bacteria disclosed in the present invention with well-described PAL domains, *Rattus norvegicus* (Plasmid E encoding protein 5 and plasmid F encoding protein 6 comprising differences in linker) and *Xenopus laevis* (plasmid G encoding protein 7) PAL domains were cloned essentially as described for protein 1 using the same fusion partner (SEQ ID NO: 7) to evaluate expression profiles for typical eukaryotic PAL containing two disulphide bridges described previously (e.g. Stoffers, D. A et al.: Proc. Natl. Acad. Sci. U.S.A. 86:735-739 (1989) and Mizuno K et al.: Biochem. Biophys. Res. Commun. 148:546-552 (1987)).

The following constructs were made (Table 1):

| Protein name | Plasmid no | Species | Fusion partner | Linker | PAL-like sequence |
|---|---|---|---|---|---|
| 1 | A | *Erythrobacter* | SEQ ID NO: 7 | SEQ ID NO: 10 | SEQ ID NO: 13 |
| 2 | B | *Erythrobacter* | SEQ ID NO: 7 | SEQ ID NO: 14 | SEQ ID NO: 15 |
| 3 | C | *Erythrobacter* | SEQ ID NO: 7 | SEQ ID NO: 8 | SEQ ID NO: 1 |
| 4 | D | *Erythrobacter* | SEQ ID NO: 11 | SEQ ID NO: 12 | SEQ ID NO: 1 |
| 5 | E | *Rattus norvegicus* | SEQ ID NO: 7 | SEQ ID NO: 9 | SEQ ID NO: 5 |
| 6 | F | *Rattus norvegicus* | SEQ ID NO: 7 | SEQ ID NO: 16 | SEQ ID NO: 5 |
| 7 | G | *Xenopus laevis* | SEQ ID NO: 7 | SEQ ID NO: 9 | SEQ ID NO: 6 |

The nucleotide sequences are described below:

```
Plasmid no: A (Erythrobacter 1):
                                                      SEQ ID NO: 26
ATGAAAGTGATTCTGCTGCGTGATGTGCCGAAAATTGGCAAAAAAGGCGAAATCAAAGAAGTGA

GCGACGGCTACGCGCGTAACTATCTGATTCCGCGTGGCTTTGCGAAAGAATATACCGAAGGCCT

GGAACGTGCGATTAAACACGAAAAAGAAATCGAAAAACGCAAAAAAGAACGCGAACGTGAAGAA

AGCGAAAAAATCCTGAAAGAACTGAAAAAACGTACCCATGTGGTGAAAGTGAAAGCGGGCGAAG

GCGGCAAAATTTTTGGCGCGGTGACCGCGGCGACCGTGGCGGAAGAAATTAGCAAAACCACCG

GCCTGAAACTGGATAAACGCTGGTTCAAACTGGACAAACCGATTAAAGAACTGGGCGAATATAGC

CTGGAAGTGAGCCTGCCGGGTGGCGTGAAAGATACCATTAAAATTCGCGTGGAACGCGAAGAAA

GCTCGAGCGGTGGCAGCGGCGGTAGCGGTGAAGCCCCGCCGGTTACCATCGATGAAAGCTGGC

CGGATATTCCGGAAAGCGCCGTGTTTGGCGAACCGACCGCCATTGATGTGGATAGCCATGGCCA

TATCTTTGTGCTGCATCGTGCCGGTCGCGAATGGACCCAGCCGTTTCCGAGCGATCCGATTAGCG

AACCGACCGTGTTCATGTTCGCCGCGAACGGCAAACTGCTGAGCAAATGGGGCGCGGGCGAACT

GGTTATGCCGCATGGTCTGAGCATTGATGGTGATAACAAAGTGTGGATTACCGATGTGGCGCGT

GAACAGGTTCTGCGTTTTACCCATGAAGGTGCGGAAGAACTGGTTCTGGGCACCCGTGGCGAAA

CCGGCCAGGATGAAAGCCATTTCGGCCGTCCGGCGGATGTTACCTTTGTGGGTGATCGTGTGCT

GGTGGCCGATGGCTATCTGAACCGTCGTATTATGGTGTTTGATCGCGCGGGCAACTTCCTGGAA
```

-continued

CAGTGGGGTAAAGAAGGTGAAGATGCGGGCGAATTTAATCTGCCGCATGCGATCGCGGCCGATA

GCGAACGTATTTATGTGGCGGATCGTGAAAACGCGCGTGTTCAGGTGCTGAGCCTGGATGGTGA

ACCGCTGGCCCGCTGGCGCCAGGATGGCACCGGCCATCCGTATGCCGTGAAACCGATTGGCAG

CGGCTATGTTCTGGCGATTGAAGGCCGCGATCGCGCGGGTCGCAATACCGCCATTGGCCGCATT

TATCGTGCGGATGGTGGCCTGGAACGTGTGTTTGATGCGGGCGTTGAACCGCATACCGGCACCA

GCCTGGGCCATGATGTGGCGATTGGTCCGGATGGTAGCGCGTATATGGTCGACAACAAAGCGAA

TCGTGTTATTAAATTTGATCTGAGCCGCGCCGGCGTTGAAGAAGCGGATGCGGAT

Plasmid no: B: (Erythrobacter 2):

SEQ ID NO: 27

ATGAAAGTGATTCTGCTGCGTGATGTGCCGAAAATTGGCAAAAAAGGCGAAATCAAAGAAGTGA

GCGACGGCTACGCGCGTAACTATCTGATTCCGCGTGGCTTTGCGAAAGAATATACCGAAGGCCT

GGAACGTGCGATTAAACACGAAAAAGAAATCGAAAAACGCAAAAAAGAACGCGAACGTGAAGAA

AGCGAAAAAATCCTGAAAGAACTGAAAAAACGTACCCATGTGGTGAAAGTGAAAGCGGGCGAAG

GCGGCAAAATTTTTGGCGCGGTGACCGCGGCGACCGTGGCGGAAGAAATTAGCAAAACCACCG

GCCTGAAACTGGATAAACGCTGGTTCAAACTGGACAAACCGATTAAAGAACTGGGCGAATATAGC

CTGGAAGTGAGCCTGCCGGGTGGCGTGAAAGATACCATTAAAATTCGCGTGGAACGCGAAGAAA

GCTCGAGCGGCGGCAGCGGTAGCGAAACCCTGTTTCAGGCGCGTGAAGAAGCGCCGCCGGTTA

CCATTGATGAAAGCTGGCCGGATATTCCGGAAAGCGCGGTGTTTGGCGAACCGACCGCGATTGA

TGTGGATAGCCATGGCCATATTTTTGTGCTGCATCGCGCGGGCCGCGAATGGACCCAGCCGTTT

CCGAGCGATCCGATTAGCGAACCGACCGTGTTTATGTTTGCGGCGAACGGCAAACTGCTGAGCA

AATGGGGCGCGGGCGAACTGGTGATGCCGCATGGCCTGAGCATTGATGGCGATAACAAAGTGT

GGATTACCGATGTGGCGCGCGAACAGGTGCTGCGCTTTACCCATGAAGGCGCGGAAGAACTGGT

GCTGGGCACCCGCGGCGAAACCGGCCAGGATGAAAGCCATTTTGGCCGCCCCGGCGGATGTGAC

CTTTGTGGGCGATCGCGTGCTGGTGGCGGATGGCTATCTGAACCGCCGCATTATGGTGTTTGAT

CGCGCGGGCAACTTTCTGGAACAGTGGGGCAAAGAAGGCGAAGATGCGGGCGAATTTAACCTG

CCGCATGCGATTGCGGCGGATAGCGAACGCATTTATGTGGCGGATCGCGAAAACGCGCGCGTG

CAGGTGCTGAGCCTGGATGGCGAACCGCTGGCGCGCTGGCGCCAGGATGGCACCGGCCATCCG

TATGCGGTGAAACCGATTGGCAGCGGCTATGTGCTGGCGATTGAAGGCCGCGATCGCGCGGGC

CGCAACACCGCGATTGGCCGCATTTATCGCGCGGATGGCGGCCTGGAACGCGTGTTTGATGCGG

GCGTGGAACCGCATACCGGCACCAGCCTGGGCCATGATGTGGCGATTGGCCCGGATGGCAGCG

CGTATATGGTCGACAACAAAGCGAACCGCGTGATTAAATTTGATCTGAGCCGCGCGGGCGTGGA

AGAAGCGGATGCGGAT

Plasmid no: C (Erythrobacter 3):

SEQ ID NO: 28

ATGAAAGTGATTCTGCTGCGTGATGTGCCGAAAATTGGCAAAAAAGGCGAAATCAAAGAAGTGA

GCGACGGCTACGCGCGTAACTATCTGATTCCGCGTGGCTTTGCGAAAGAATATACCGAAGGCCT

GGAACGTGCGATTAAACACGAAAAAGAAATCGAAAAACGCAAAAAAGAACGCGAACGTGAAGAA

AGCGAAAAAATCCTGAAAGAACTGAAAAAACGTACCCATGTGGTGAAAGTGAAAGCGGGCGAAG

GCGGCAAAATTTTTGGCGCGGTGACCGCGGCGACCGTGGCGGAAGAAATTAGCAAAACCACCG

GCCTGAAACTGGATAAACGCTGGTTCAAACTGGACAAACCGATTAAAGAACTGGGCGAATATAGC

CTGGAAGTGAGCCTGCCGGGTGGCGTGAAAGATACCATTAAAATTCGCGTGGAACGCGAAGAAA

GCTCGAGCGGCGGCAGCGGTAGCGAAGTGCTGTTTCAGGGCCCGCCGGTTACCATTGATGAAA

GCTGGCCGGATATTCCGGAAAGCGCGGTGTTTGGCGAACCGACCGCGATTGATGTGGATAGCCA

-continued

```
TGGCCATATCTTTGTGCTGCATCGTGCCGGTCGCGAATGGACCCAGCCGTTTCCGAGCGATCCG

ATTAGCGAACCGACCGTGTTCATGTTCGCCGCGAACGGCAAACTGCTGAGCAAATGGGGCGCGG

GCGAACTGGTTATGCCGCATGGTCTGAGCATTGATGGTGATAACAAAGTGTGGATTACCGATGTG

GCGCGTGAACAGGTTCTGCGTTTTACCCATGAAGGTGCGGAAGAACTGGTTCTGGGCACCCGTG

GCGAAACCGGCCAGGATGAAAGCCATTTCGGCCGTCCGGCGGATGTTACCTTTGTGGGTGATCG

TGTGCTGGTGGCCGATGGCTATCTGAACCGTCGTATTATGGTGTTTGATCGCGCGGGCAACTTCC

TGGAACAGTGGGGTAAAGAAGGTGAAGATGCGGGCGAATTTAATCTGCCGCATGCGATCGCGGC

CGATAGCGAACGTATTTATGTGGCGGATCGTGAAAACGCGCGTGTTCAGGTGCTGAGCCTGGAT

GGTGAACCGCTGGCCCGCTGGCGCCAGGATGGCACCGGCCATCCGTATGCCGTGAAACCGATT

GGCAGCGGCTATGTTCTGGCGATTGAAGGCCGCGATCGCGCGGGTCGCAATACCGCCATTGGCC

GCATTTATCGTGCGGATGGTGGCCTGGAACGTGTGTTTGATGCGGGCGTTGAACCGCATACCGG

CACCAGCCTGGGCCATGATGTGGCGATTGGTCCGGATGGTAGCGCGTATATGGTCGACAACAAA

GCGAATCGTGTTATTAAATTTGATCTGAGCCGCGCCGGCGTTGAAGAAGCGGATGCGGAT
```

Plasmid no: D (Erythrobacter 4);:
SEQ ID NO: 29

```
ATGGGCAGCAGCCATCATCATCATCATCACTCGAGCGGCGGCAGCGGTAGCGAAGTGCTGTTTC

AGGGCCCGCCGGTTACCATTGATGAAAGCTGGCCGGATATTCCGGAAAGCGCGGTGTTTGGCGA

ACCGACCGCGATTGATGTGGATAGCCATGGCCATATCTTTGTGCTGCATCGTGCCGGTCGCGAAT

GGACCCAGCCGTTTCCGAGCGATCCGATTAGCGAACCGACCGTGTTCATGTTCGCCGCGAACGG

CAAACTGCTGAGCAAATGGGGCGCGGGCGAACTGGTTATGCCGCATGGTCTGAGCATTGATGGT

GATAACAAAGTGTGGATTACCGATGTGGCGCGTGAACAGGTTCTGCGTTTTACCCATGAAGGTGC

GGAAGAACTGGTTCTGGGCACCCGTGGCGAAACCGGCCAGGATGAAAGCCATTTCGGCCGTCC

GGCGGATGTTACCTTTGTGGGTGATCGTGTGCTGGTGGCCGATGGCTATCTGAACCGTCGTATTA

TGGTGTTTGATCGCGCGGGCAACTTCCTGGAACAGTGGGGTAAAGAAGGTGAAGATGCGGGCG

AATTTAATCTGCCGCATGCGATCGCGGCCGATAGCGAACGTATTTATGTGGCGGATCGTGAAAAC

GCGCGTGTTCAGGTGCTGAGCCTGGATGGTGAACCGCTGGCCCGCTGGCGCCAGGATGGCACC

GGCCATCCGTATGCCGTGAAACCGATTGGCAGCGGCTATGTTCTGGCGATTGAAGGCCGCGATC

GCGCGGGTCGCAATACCGCCATTGGCCGCATTTATCGTGCGGATGGTGGCCTGGAACGTGTGTT

TGATGCGGGCGTTGAACCGCATACCGGCACCAGCCTGGGCCATGATGTGGCGATTGGTCCGGAT

GGTAGCGCGTATATGGTCGACAACAAAGCGAATCGTGTTATTAAATTTGATCTGAGCCGCGCCGG

CGTTGAAGAAGCGGATGCGGAT
```

Plasmid no: E (rat 1):
SEQ ID NO: 30

```
ATGAAAGTGATTCTGCTGCGTGATGTGCCGAAAATTGGCAAAAAGGCGAAATCAAAGAAGTGA

GCGACGGCTACGCGCGTAACTATCTGATTCCGCGTGGCTTTGCGAAAGAATATACCGAAGGCCT

GGAACGTGCGATTAAACACGAAAAAGAAATCGAAAAACGCAAAAAAGAACGCGAACGTGAAGAA

AGCGAAAAAATCCTGAAAGAACTGAAAAAACGTACCCATGTGGTGAAAGTGAAAGCGGGCGAAG

GCGGCAAAATTTTTGGCGCGGTGACCGCGGCGACCGTGGCGGAAGAAATTAGCAAAACCACCG

GCCTGAAACTGGATAAACGCTGGTTCAAACTGGACAAACCGATTAAAGAACTGGGCGAATATAGC

CTGGAAGTGAGCCTGCCGGGTGGCGTGAAAGATACCATTAAATTCGCGTGGAACGCGAAGAAA

GCTCGAGCGGGAGCGGCGAAGTTCTGTTTCAGGGCGATTTTCATGTGGAAGAGGAACTGGATTG

GCCGGGTGTTTATCTGCTGCCGGGGCAGGTGAGCGGCGTTGCCCTGGATAGTAAAAACAACCTG
```

-continued

```
GTGATTTTCCACCGTGGAGATCATGTGTGGGATGGTAACTCATTCGATAGCAAATTTGTCTATCA

GCAGCGCGGCCTGGGTCCTATTGAAGAAGATACCATCCTGGTTATCGATCCGAATAATGCGGAA

ATTCTGCAAAGTTCTGGAAAAAACCTGTTCTACCTGCCTCATGGGCTGAGCATCGATACCGATGG

TAACTACTGGGTTACCGATGTAGCCCTGCATCAGGTCTTCAAACTGGACCCACATTCAAAAGAAG

GTCCGCTGCTGATTCTGGGACGTTCTATGCAGCCTGGCAGCGATCAGAACCATTTTTGCCAACCA

ACAGATGTCGCCGTGGAGCCGTCGACTGGTGCTGTGTTTGTGTCGGACGGCTACTGTAACTCCC

GTATCGTCCAGTTTAGCCCGTCAGGTAAATTTGTTACACAGTGGGGCGAAGAGTCGTCTGGCTCT

AGTCCGCGCCCGGGCCAGTTTTCGGTGCCGCATAGCCTGGCCCTGGTGCCGCATCTGGACCAGC

TGTGTGTGGCCGACCGTGAGAACGGCCGCATTCAATGCTTTAAAACTGATACAAAGGAATTTGTT

CGCGAAATTAAACACGCCAGCTTTGGACGTAATGTTTTCGCGATTTCATACATTCCAGGCTTTCTG

TTTGCAGTCAACGGCAAACCATATTTTGGCGATCAGGAACCGGTACAGGGTTTTGTTATGAATTTT

TCATCGGGCGAAATTATTGATGTTTTTAAACCTGTGCGCAAACATTTCGATATGCCACATGATATT

GTGGCTAGCGAGGACGGTACGGTTTATATTGGGGATGCGCACACGAACACCGTGTGGAAATTCA

CCCTGACCGAAAAAATGGAACACCGTTCGGTC
```

Plasmid no: F (rat2):

SEQ ID NO: 31

```
ATGAAAGTGATTCTGCTGCGTGATGTGCCGAAAATTGGCAAAAAAGGCGAAATCAAAGAAGTGA

GCGACGGCTACGCGCGTAACTATCTGATTCCGCGTGGCTTTGCGAAAGAATATACCGAAGGCCT

GGAACGTGCGATTAAACACGAAAAAGAAATCGAAAAACGCAAAAAAGAACGCGAACGTGAAGAA

AGCGAAAAAATCCTGAAAGAACTGAAAAAACGTACCCATGTGGTGAAAGTGAAAGCGGGCGAAG

GCGGCAAAATTTTTGGCGCGGTGACCGCGGCGACCGTGGCGGAAGAAATTAGCAAAACCACCG

GCCTGAAACTGGATAAACGCTGGTTCAAACTGGACAAACCGATTAAAGAACTGGGCGAATATAGC

CTGGAAGTGAGCCTGCCGGGTGGCGTGAAAGATACCATTAAAATTCGCGTGGAACGCGAAGAAA

GCTCGAGCGGGGTAGCGGCGGCTCTGGCGATTTTCATGTGGAAGAGGAACTGGATTGGCCGG

GTGTTTATCTGCTGCCGGGGCAGGTGAGCGGCGTTGCCCTGGATAGTAAAAACAACCTGGTGAT

TTTCCACCGTGGAGATCATGTGTGGGATGGTAACTCATTCGATAGCAAATTTGTCTATCAGCAGC

GCGGCCTGGGTCCTATTGAAGAAGATACCATCCTGGTTATCGATCCGAATAATGCGGAAATTCTG

CAAAGTTCTGGAAAAAACCTGTTCTACCTGCCTCATGGGCTGAGCATCGATACCGATGGTAACTA

CTGGGTTACCGATGTAGCCCTGCATCAGGTCTTCAAACTGGACCCACATTCAAAAGAAGGTCCGC

TGCTGATTCTGGGACGTTCTATGCAGCCTGGCAGCGATCAGAACCATTTTTGCCAACCAACAGAT

GTCGCCGTGGAGCCGTCGACTGGTGCTGTGTTTGTGTCGGACGGCTACTGTAACTCCCGTATCG

TCCAGTTTAGCCCGTCAGGTAAATTTGTTACACAGTGGGGCGAAGAGTCGTCTGGCTCTAGTCCG

CGCCCGGGCCAGTTTTCGGTGCCGCATAGCCTGGCCCTGGTGCCGCATCTGGACCAGCTGTGTG

TGGCCGACCGTGAGAACGGCCGCATTCAATGCTTTAAAACTGATACAAAGGAATTTGTTCGCGAA

ATTAAACACGCCAGCTTTGGACGTAATGTTTTCGCGATTTCATACATTCCAGGCTTTCTGTTTGCA

GTCAACGGCAAACCATATTTTGGCGATCAGGAACCGGTACAGGGTTTTGTTATGAATTTTTCATCG

GGCGAAATTATTGATGTTTTTAAACCTGTGCGCAAACATTTCGATATGCCACATGATATTGTGGCT

AGCGAGGACGGTACGGTTTATATTGGGGATGCGCACACGAACACCGTGTGGAAATTCACCCTGA

CCGAAAAAATGGAACACCGTTCGGTC
```

Plasmid no: G (Xenopus):

SEQ ID NO: 32

```
ATGAAAGTGATTCTGCTGCGTGATGTGCCGAAAATTGGCAAAAAAGGCGAAATCAAAGAAGTGA

GCGACGGCTACGCGCGTAACTATCTGATTCCGCGTGGCTTTGCGAAAGAATATACCGAAGGCCT
```

-continued

```
GGAACGTGCGATTAAACACGAAAAAGAAATCGAAAAACGCAAAAAAGAACGCGAACGTGAAGAA

AGCGAAAAAATCCTGAAAGAACTGAAAAAACGTACCCATGTGGTGAAAGTGAAAGCGGGCGAAG

GCGGCAAAATTTTTGGCGCGGTGACCGCGGCGACCGTGGCGGAAGAAATTAGCAAAACCACCG

GCCTGAAACTGGATAAACGCTGGTTCAAACTGGACAAACCGATTAAAGAACTGGGCGAATATAGC

CTGGAAGTGAGCCTGCCGGGTGGCGTGAAAGATACCATTAAAATTCGCGTGGAACGCGAAGAAA

GCTCGAGCGGGAGCGGCGAAGTTCTGTTTCAGGGCGATGTGCATCTGGAAGAAGATACCGACTG

GCCGGGTGTGAACCTTAAAGTGGGCCAGGTGAGCGGGCTAGCCCTGGACCCGAAAAACAACCT

GGCCATTTTTCATCGTGGCGATCATGTGTGGGATGAAAACAGCTTTGATCGCAACTTTGTGTATC

AGCAGCGTGGCATTGGCCCGATTCAGGAAAGCACCATTCTGGTTGTTGATCCGAGCAGCAGCAA

AGTGCTGAAAAGCACCGGCAAAAACCTGTTTTTTCTGCCGCATGGCCTGACCATTGATCGTGATG

GCAACTATTGGGTGACCGATGTGGCGCTGCATCAGGTGTTTAAACTGGGTGCGGGCAAAGAAAC

CCCGCTGCTGGTGCTGGGTCGTGCGTTTCAGCCGGGCAGCGATCGTAAACATTTTTGCCAGCCG

ACCGATGTTGCGGTTGATCCGATTACCGGCAACTTTTTTGTGGCGGATGGCTATTGCAACAGCCG

TATTATGCAGTTTAGCCCGAACGGCATGTTTATTATGCAGTGGGGCGAAGAAACCAGCAGCAACG

TGCCGCGTCCGGGCCAGTTTCGTATTCCGCACAGCCTGACCATGGTGCCGGATCAGGGCCAGCT

GTGCGTGGCGGATCGTGAAAACGGCCGTATTCAGTGCTTTCATGCGGAAACCGGCAATTTTGTG

AAACAAATCAAACATCAGGAATTTGGCCGCGAAGTTTTTGCGGTGAGCTATGCGCCGGGTGGTG

TGCTGTATGCGGTGAACGGCAAACCGTATTATGGCTATAGCGCACCGGTGCAGGGCTTTATGCT

GAACTTTAGCAACGGCGATATTCTGGATACCTTTATTCCGGCGCGTAAAAACTTTGATATGCCGCA

TGATATTGCGGCAGCGGATGATGGCACCGTGTATGTGGGCGATGCGCATGCGAACGCGGTGTG

GAAATTTAGCCCGAGCAAAGCGGAACATCGGTCCGTG
```

Expression of Constructs:

Plasmids with the correct DNA sequence were transformed into *E. coli* expression strain BL21 (DE3), which were plated on LB/ampicillin plates overnight. BL21 (DE3) host cells with plasmids were propagated in LB medium protein expression was induced using the T7/IPTG expression system.

*E. coli* BL21 (DE3) cells transformed with plasmids encoding fusion constructs were grown to a optical density (OD600 nm) of ~0.4-0.6 at 37° C. in LB/Ampecillin medium using shaker flasks. If the tested induction temperature was 18° C. or 30° C., the temperature was lowered accordingly to 18° C. or 30° C. for approximately 30 min, and 0.5 mM IPTG was added to the culture for 3 hours. Following protein induction, cultures were pelleted and cells were lysed by ultrasonication in 25 mM NaPO4 pH 7 buffer. SDS-PAGE analysis of was carried out of lysate samples in sample buffer containing induced and uninduced cells, as well as soluble and insoluble fractions of induced cells (obtained by ultrasonication and centrifugation in a buffer consisting of 25 mM NaPO$_4$ pH 7). The analysis was performed to evaluate expression level and solubility of the variant.

Expression Profile of *Erythrobacter* Variants and Comparison to Well-Described Eukaryotic PAL Domains from *Rattus norvegicus* and *Xenopus laevis*

When expressed from plasmids in BL21 (DE3) for 3 hours at 30° C. in 1 L baffled shaker flasks, the protein 3, protein 1 or protein 2 *Erythrobacter* protein variants showed expected molecular weights around 50 kDa and very similar expression levels. A consistently high degree of solubility (~80%) at neutral pH was observed (in a buffer containing 25 mM NaPO4 pH 7, exemplified for protein 2 in FIG. 2A).

Same expression levels were observed for PAL from rat (protein 6) or *Xenopus* PAL (protein 7) using the same N-terminal tag and linker as protein 1. However, in contrast to the *Erythrobacter* PAL-like domains, the PAL domains from rat and *Xenopus* consistently resulted in insoluble protein, when using the same expression conditions ((Exemplified for protein 6 in FIG. 2B). Rat PAL with a different linker (protein 5) did not change the expression profile, but still resulted in an insoluble protein using the same expression conditions. Comparison of expression profiles (protein 3 against protein 6), at expression conditions at 18° C., 30° C. or 37° C. showed that the *Erythrobacter* protein was soluble protein at all three temperatures, whereas the rat PAL was insoluble at all three temperatures. This shows the advantage of expressing the prokaryotic PAL, which contains no disulphide bridges compared to the eukaryotic PAL, which is more likely to make aggregates during expression. The *Erythrobacter* PAL-like domain can also be made as soluble fusion protein despite variations in the 5 aa region of the N-terminal of the PAL protein and in the linker region.

The His tagged variant of *Erythrobacter* protein (protein 4) resulted in a soluble protein when expressed both at 30° C. and 37° C., thus demonstrating that the high solubility of the *Erythrobacter* protein is not dependent on the nature of the N-terminal fusion tag used, but is rather an inherent property of the protein.

Purification of SEQ ID NO: 7 tagged *Erythrobacter* PAL-like fusion proteins on SP Sepharose FF:

Following expression of PAL-like enzymes (protein 1, protein 2 or protein 3) or rat PAL (protein 6) in 1-2 L baffled shaker flasks for 3 hours at 30° C. as described above purification by cation exchange chromatography using SP Sepharose FF 5 ml columns was carried out as described in the following:

Cell culture pellets (from 80 ml of culture OD600: ~1.6-1.8) of the enzyme variants were disrupted by ultrasonication in a total of 20 ml 25 mM $NaPO_4$ pH 7 buffer. Cell debris was spun down by centrifugation (4000 rpm, 15 min). Supernatants were sterile filtrated (0.45 uM filters) and diluted to a total volume of 40 ml with 25 mM $NaPO_4$ pH 7 buffer to obtain the protein application. Purification was carried out using a AKTA explorer 100 purification system (GE Healthcare). A prepacked SP Sepharose FF HiTrap column with a 5 ml column volume (GE Healthcare, product no: 17-5157-01) was used for the separation at a flow rate of 3 ml/min using the following buffers:

Buffer A: 50 mM sodium phosphate, pH 7
Buffer B: 50 mM sodium phosphate, pH 7+1M NaCl The column was initially equilibrated for 7 column volumes of buffer A. After loading of the application, unbound protein was removed by washing using 7 column volumes of buffer A. A linear gradient from 0-100% buffer B for 20 column volumes was used to elute the enzymes from the column.

Application, flow through fractions and fractions representing protein eluted within the gradient were separated by SDS-PAGE and gels were analyzed following Coomassie Brilliant Blue staining or LC-MS analysis.

Both protein 1, protein 2 or protein 3 eluted from the column at a salt concentration of ~0.3 M NaCl in a single peak, which according to SDS-PAGE had high purity of ~80% (FIGS. 3A and B exemplified for protein 3). No significant amount of protein was observed in the flow through fraction indicating that the *Erythrobacter* variants were all efficiently captured by the SP Sepharose FF column.

In contrast, attempts to purify rat (protein 6) or *X. laevis* PAL (protein 7) fusion proteins, using the exact same conditions for sample preparation and purification failed indicating that the eukaryotic PAL adopts an incorrectly folded confirmation upon expression in *E. coli*, which does not readily allow purification by cation chromatography.

Fractions containing eluted *Erythrobacter* PAL-like enzymes were pooled together and concentrated and desalted in a buffer containing 50 mM Tris pH 7.5 using Vivaspin MWCO10.000 columns (Vivaspin) according to the manufacturers instructions. Glycerol was added to a total conc. of 10% and enzymes were stored until used at 20° C.

Purification and LC-MS Analysis of Mature *Erythrobacter* PAL-Like (SEQ ID NO:1) without Purification Tag Cleavage with TAP Tagged HRV14 3C Protease To remove the purification tag from protein 3, ~1.5 mg of the fusion protein present in 50 mM Tris HCl pH 7.5, 10% glycerol buffer, 1 mM TCEP was cleaved overnight at 30° C. using a TAP tagged HRV14 3C protease (from WO 2008/043847) at an enzyme to substrate ratio of 1:25 in a reaction volume of 3 ml (ratios were estimated following protein concentration measurement using NanoDrop2000, Thermo Scientific according to the instructions of the manufacturer). Coomassie stained SDS-PAGE gels and LC-MS analysis was used to confirm that enzymatic cleavage occurred using the following protocol: The LC-MSD_TOF (Agilent technologies) instrument, was used with MS settings recommended by the manufacturer, to analyze the samples using an analytical Poroshell 300SB-C8, Micro Bore 1.0×75 mm, 5 micron (Agilent Technologies) column at standard HPLC conditions with a flow of 0.3 ml/min and a column temperature of 40° C.: A gradient elution was formed in a 20 min. run using 8.8 mM ammonium formate in 0.1% formic acid water (Buffer A) and Acetonitrile (Buffer B) as follows:

| Time (min) | % Buffer B |
|---|---|
| 0 | 22 |
| 3 | 22 |
| 15 | 75 |
| 15.1 | 90 |
| 20 | 90 |

LC-MS analysis of overnight HRV14 3C protease digests of protein 3 resulted in two fragments determined to 33323 Da and 18284.78 Da corresponding to the released PAL-like domain (SEQ ID NO 1, calculated mass 33323.97 Da) and to the released purification tag and HRV14 3C linker (SEQ ID NO: 7+SEQ ID NO:8, calculated mass: 18285.18 Da), respectively. No visible degradation products were observed either in the uncleaved control nor in the digest by SDS-PAGE analysis indicating high stability of both the mature PAL-like domain as well as the fusion protein.

Purification of Mature Domains on Q-Sepharose HP

Digests containing the released mature PAL-domains were diluted 1:3 with 25 mM $NaPO_4$ pH 7 and the sample application was loaded on a 1 ml HiTrap Q Sepharose High Performance (HP) anion exchange column (GE Healthcare 17-1153-01) and separated using the AKTA Explorer 100 system (GE Healthcare) with the following purification buffers:

Buffer A: 50 mM sodium phosphate, pH 7
Buffer B: 50 mM sodium phosphate, pH 7+1M NaCl The column was initially equilibrated for 7 column volumes of buffer A. After loading of the application, unbound protein was removed by washing using 7 column volumes of buffer A. A linear gradient from 0-100% buffer B for 20 column volumes was used to elute the enzymes from the column.

A single peak was observed within the gradient at a NaCl conc. of ~0.3 M

SDS-PAGE of the Application, Flow through fractions and fractions covering the eluted protein showed that the released SEQ ID NO: 7+SEQ ID NO: 8 fragment representing the purification tag and HRV14 3C linker, was present in the flow through, and the released PAL-like domain (SEQ ID NO: 1) was present in the single major peak eluated from the gradient. The purity of the eluted protein was estimated to be ~90% showing that the mature PAL-like domain can be purified to high purity in only two chromatographic steps.

Fractions containing eluted mature enzyme (SEQ ID NO: 1) were pooled together and up-concentrated and desalted in a buffer containing 50 mM Tris pH 7.5, 10% Glycerol using Vivaspin MWCO 10,000 Da columns (Vivaspin) and stored at 20° C. until used.

Example 1 shows that the PAL Enzymes of the invention can be made as soluble protein even with variations in the 5 aa region of the N-terminal of the PAL protein.

Example 2

Cloning, Expression Fusion Protein with Ribosomal Protein L9 as Purification Tag and PAL-Like Domain from *Exiguobacterium* sp. (Strain ATCC BAA-1283/AT1b) and Purification of Fusion Protein and Mature PAL-Like Domain Protein 8 is a Exiguibacterium PAL-like domain (SEQ ID NO: 2) with an N-terminal purification tag (SEQ ID NO 7) and HRV14 3C protease site containing linker (SEQ ID NO 8). The fusion protein has an calculated molecular weight of 56,115 Da and the mature PAL-like domain has an calculated molecular weight of 37848.5 Da The following construct were made:

described in example 1. Expression at 30° C. for 3 hours and SDS-PAGE analysis was performed as described in Example 1.

The expression levels of protein 8 was very similar to the *Erythrobacter* variants. The protein was again highly soluble, with almost no protein detected in the insoluble fraction of the cell lysate.

Cation exchange capture, cleavage with HRV14 3C and purification of mature *Exiguobacterium* PAL-like domain was performed essentially as described in Example 1. Following the capture on SP Sepharose FF a major peak eluted at a NaCl conc. of ~0.25 M and based on SDS-PAGE analysis the capture was highly efficient as well as the initial purity of the purified fusion protein ~80%.

| Protein name | Plasmid no | Species | Fusion partner | Linker | PAL-like sequence |
|---|---|---|---|---|---|
| 8 | H | *Exiguobacterium* | SEQ ID NO: 7 | SEQ ID NO: 8 | SEQ ID NO: 2 |

Plasmid no: H (*Exiguobacterium*): SEQ ID NO: 33
ATGAAAGTGATTCTGCTGCGTGATGTGCCGAAAATTGGCAAAAAAGGCGAAATCAAAGAAGTGA

GCGACGGCTACGCGCGTAACTATCTGATTCCGCGTGGCTTTGCGAAAGAATATACCGAAGGCCT

GGAACGTGCGATTAAACACGAAAAAGAAATCGAAAAACGCAAAAAAGAACGCGAACGTGAAGAA

AGCGAAAAAATCCTGAAAGAACTGAAAAAACGTACCCATGTGGTGAAAGTGAAAGCGGGCGAAG

GCGGCAAAATTTTTGGCGCGGTGACCGCGGCGACCGTGGCGGAAGAAATTAGCAAAACCACCG

GCCTGAAACTGGATAAACGCTGGTTCAAACTGGACAAACCGATTAAAGAACTGGGCGAATATAGC

CTGGAAGTGAGCCTGCCGGGTGGCGTGAAAGATACCATTAAAATTCGCGTGGAACGCGAAGAA

GCTCGAGCGGCGGCAGCGGTAGCGAAGTGCTGTTTCAGGGTCCGCGTACCGATCCGATTTTTAA

AGATGAATATGATGAAAAAGCCAAAAGCAGCCGTTATACCAGCAGCTGGGTTTGGCCTGAAAAAG

ATAGCGTTAGCCATCGTGGTGGTGAAGGTAGCGGTGTTAGCACCAGCCCGAGCGGTTATGTTTA

TTATCTGCATCGTGGTGATGGTAGCTATGCAAATGAAGAACTGATTACCACCCCGACCATTACCG

TTTTTGATCCGAATACCAATGAAATTGTGGATGAATTTGGCGATAACCTGTTTCAGTCTCCGCATG

GTATTGAAGTTGATAGCCAGAATAATATTTGGGTGACCGATATTATGCTGAATAAAGTGTTTAAAC

TGGATGAACGTGGTAATGTTCTGGCCACCTTTGGTGATGATTATCGTCTGGGCACCGAAACCAGC

CTGCGTATTCGTAATGAACTGCCGAATTTTCCGGTTCCGATGAATGAATACACCTTTGCACGTCCG

ACCGATGTTACCGTTATGGAAGATGGCAGCTTTATTGTTGCAGATGGCTATCGCAATCATCGTATT

GTGAAATTTAATCGTGATGGCAATATTCAGTGGGAAGTTGATGCATATGGTAGCTCTGATGGCGA

ATTTAATCTGCCGCATGGCATTACCCATGATCAGAGCGGCAATATTTATGTTGCCGATCGCAATAA

TGCACGTATTCAGGTGTTTGATCAGGATGGTCAGCATCTGAGCACCTGGGATGATACCGAAATTG

GCCGTCCTTATGGAATCGATGCAGGCAATGATGGTAATATTTATCTGGTGGATGGTGGCGATTAT

CTGAATGGTGAACGTGAAACCCCGAAAAGCCAGATTGTTGTTCTGAGCCCGAAAGGTGAAGTTAT

TGAACGTTTTGGTAGCTGGGGTAACAAAATGGGTCAGCTGCGTATTCCGCATGATCTGACCGTGC

TGGAAGATGGTACAATTTTTGTTGCCGAACTGCTGAATGAACGTCTGCAGAAATTTACCATTACCG

AA

Plasmid H encoding protein 8 was obtained by ligating a synthetic XhoI/BamHI fragment encoding the linker and PAL-like region into an pET11a already encoding a TAP tag (SEQ ID NO: 7) and performing the verification steps as Purification of mature *Exiguobacterium* PAL-like protein (SEQ ID NO: 2) following HRV14 3C protease cleavage of pooled and concentrated fusion protein (using 1:25 enzyme to substrate ratio overnight) was performed with the same efficiency as described in Example 1. The mature PAL-like domain eluted from the Q Sepharose HP column at a NaCl conc. of ~0.5 M (FIG. 4A). SDS-PAGE analysis showed that two fragments corresponding to the mature Exiguibacterium PAL-like domain (SEQ ID NO:2) (upper band) and the released TAP tag (SEQ ID NO:7-SEQ ID NO:8) (lower band) was present in the application (FIG. 4B). Following anion exchange separation, the mature *Exiguobacterium* PAL-like domain was found in the major peak (fractions 12-15) eluting from the gradient and the released tag was present in the flow through fractions (FIG. 4B).

Fractions containing eluted enzymes were pooled together and up-concentrated and desalted in a buffer containing 50 mM Tris pH 7.5 using Vivaspin MWCO 10,000 Da columns (Vivaspin) and stored at 20° C. until used.

Example 3

Cloning, Expression and Purification of Fusion Protein with Ribosomal Protein L9 as Purification Tag and PAL-Like Domain from *Chthoniobacter flavus* Ellin428

Protein 9 is a *Chthoniobacter flavus* Ellin428 (SEQ ID NO: 3) with an N-terminal purification tag (SEQ ID NO: 7) and HRV14 3C protease site containing linker (SEQ ID NO: 8). The fusion protein has an calculated molecular weight of 51650.4 Da and the mature PAL-like domain with Gly-Pro N-terminal has an calculated molecular weight of 33383.3 Da The following constructs were made:

| Protein name | Plasmid no | Species | Fusion partner | Linker | PAL-like sequence |
|---|---|---|---|---|---|
| 9 | I | *Chthoniobacter* | SEQ ID NO: 7 | SEQ ID NO: 8 | SEQ ID NO: 3 |

Plasmid no: I (*Chthoniobacter*): SEQ ID NO: 34
ATGAAAGTGATTCTGCTGCGTGATGTGCCGAAAATTGGCAAAAAAGGCGAAATCAAAGAAGTGA

GCGACGGCTACGCGCGTAACTATCTGATTCCGCGTGGCTTTGCGAAAGAATATACCGAAGGCCT

GGAACGTGCGATTAAACACGAAAAAGAAATCGAAAAACGCAAAAAAGAACGCGAACGTGAAGAA

AGCGAAAAAATCCTGAAAGAACTGAAAAAACGTACCCATGTGGTGAAAGTGAAAGCGGGCGAAG

GCGGCAAAATTTTTGGCGCGGTGACCGCGGCGACCGTGGCGGAAGAAATTAGCAAAACCACCG

GCCTGAAACTGGATAAACGCTGGTTCAAACTGGACAAACCGATTAAAGAACTGGGCGAATATAGC

CTGGAAGTGAGCCTGCCGGGTGGCGTGAAAGATACCATTAAAATTCGCGTGGAACGCGAAGAAA

GCTCGAGCGGCGGCAGCGGTAGCGAAGTGCTGTTTCAGGGTCCGGAAAGCCGTTATGAAGTTGT

TCCGCATTGGCCTGTTCTGCCGGAAGGTCGTAGCCTGGGTGTTTGTGCAGGTGTTGGTGTTGATA

GCCATGGTAATGTGTTTGTGTTTCATCGTAATGAACGTAATTGGACCGCAGCATTTCCGGAAGAA

CCGATTGCAGAACCGACCATTTCTGTTTTTGATGGTCAGAGCGGCAAACTGCTGACCGAATGGGG

TGCAGGTGAATTTATTATGCCGCATGGTCTGACCCTGGATCGTGAAGATAATGTTTGGCTGACCG

ATGTTGGTCGTCAGCAGGTTTTTAAATATGCCCATGATGGTCATCTGCTGCTGACCCTGGGTGAA

CGTGGTGTTGCAGGTAGCGATCAGACCCATTTTAATCTGCCGACCGATGTTGCAGTGCTGCCTGA

TGGAAGCTTTTATGTGTCTGATGGCTATCGTAATACCCGTGTGGTTAAATTTGATGCCGCAGGCC

ATTATCAGTTTGAATGGGGTGGTAAAGGCACCGAACCGGGTAAATTTCGTCTGCCTCATGGAGTT

GCAGTTGATTCTCATGGTCGTGTTTTTGTTTGCGATCGTACCAATAGCCGTCTGCAGGTTTTTGAT

CCGAAAGGTAAATTTCTGGCCGAATGGAAAGGTCCGCAGGTTGGTCGTCCGTATGGTGTTAGCG

TTGCAGCAAATGATCATGTGTTTGTGATTGATGGTGGTGATCAGCTGCCGAATCAGCCGGAACAT

GCAAAAGCAGTTGAACTGGACCCTGAAGGTAATGTTGTTCCGCGTTTTGGTAGCTATGGTCGTGA

TCCGGGTCAGTTTCAGCTGGGTCATGATATTGCAGTTGCACCGGATGGTTCTGTTTATGTTGGTG

ATGCCAAAGGTAAACGCGTTCAGAAATTTGTTCCGGTGCATCCG

Plasmid I encoding protein 9 was obtained by ligating a synthetic XhoI/BamHI fragment encoding the linker and PAL-like region into an pET11a already encoding a purification tag (SEQ ID NO 7) and performing the verification steps as described in example 1. Expression at 30° C. for 3 hours and SDS-PAGE analysis was performed as described in Example 1.

The expression levels of protein 9 was lower than *Erythrobacter* and *Exiguobacterium* PAL-like variants. However, the protein was predominantly soluble at neutral pH.

By cation exchange capture on SP Sepharose FF a major peak was observed at a NaCl conc. of ~0.25 M. The capture was however less efficient as observed for the two previous domains all though the purity was comparably high based on SDS-PAGE analysis.

Fractions containing eluted enzymes were pooled together and up-concentrated and desalted in a buffer containing 50 mM Tris pH 7.5 using Vivaspin MWCO 10,000 Da columns (Vivaspin) and stored at 20° C. until used.

Example 4

Cloning, Expression and Purification of Fusion Protein with Ribosomal Protein L9 as Purification Tag and PAL-Like Domain from *Planctomyces* Mares DSM 8797

Protein 10 is a PAL-like domain from *Planctomyces* DSM 8797 (SEQ ID NO: 4) with an N-terminal purification tag (SEQ ID NO: 7) and HRV14 3C protease site containing linker (SEQ ID NO: 8). For the *Planctomyces* PAL-like domain the two Cys residues occurring in the wild type sequence was replaced with an Alanine and a Valine residue.

The fusion protein has an calculated molecular weight of 48678.56 Da and the mature PAL-like domain with Gly-Pro N-terminal has an calculated molecular weight of 30411.4 Da.

The following construct were made:

| Protein name | Plasmid no | Species | Fusion partner | Linker | PAL sequence |
|---|---|---|---|---|---|
| 10 | J | *Planctomyces* | SEQ ID NO: 7 | SEQ ID NO: 8 | SEQ ID NO: 4 |

Plasmid no: J *Planctomyces*: SEQ ID NO: 35

```
ATGAAAGTGATTCTGCTGCGTGATGTGCCGAAAATTGGCAAAAAAGGCGAAATCAAAGAAGTGA

GCGACGGCTACGCGCGTAACTATCTGATTCCGCGTGGCTTTGCGAAAGAATATACCGAAGGCCT

GGAACGTGCGATTAAACACGAAAAAGAAATCGAAAAACGCAAAAAAGAACGCGAACGTGAAGAA

AGCGAAAAAATCCTGAAAGAACTGAAAAAACGTACCCATGTGGTGAAAGTGAAAGCGGGCGAAG

GCGGCAAAATTTTTGGCGCGGTGACCGCGGCGACCGTGGCGGAAGAAATTAGCAAAACCACCG

GCCTGAAACTGGATAAACGCTGGTTCAAACTGGACAAACCGATTAAAGAACTGGGCGAATATAGC

CTGGAAGTGAGCCTGCCGGGTGGCGTGAAAGATACCATTAAAATTCGCGTGGAACGCGAAGAAA

GCTCGAGCGGTGGTAGCGGTAGCGAAGTTCTGTTTCAGGGTCCGGCAGATAAAATTGATTTTGA

ACCGGCAGCCATTAATATTGAACTGCCGGAAGGTCTGGCACTGGGTCCTGCAAGCGCAGTTGAT

TTTGATAGCAAAGGTCGCATGTACCTGTTTCATCGTGGTCCGCAGCCGATTCTGGTTTTTGATCAG

AGCGGTAAATTTGTTCGTAGCTGGGGTGATAAACTGATTAGCCAGGCACATGGCTTAAGAGTTGC

ACCGGATGAAACCATTTGGGTTACCGATATTGGCAACCACATGGTGTTTCAGTTTAACCCGGAAG

GTAAACTGCTGCTGGCCCTGGGTCAGGCAGGTAAACCGGGTGATAGCCAGGATCAGTTTAATAA

ACCGACCGATATTGCATTTGGTCCGCAGGGCGAATTCTATATTTCTGACGGCTATGGTAATAGCC

GTGTGATGAAATTTGCAGCCAATGGTAAAAATCTGGGTCAGTGGGGTACACCGGGTAAAGGTCC

GGGTGAATTTAATCTGCCGCATAGCATTCTGGTTGATGCAAAAGGTCGTGTTCTGGTTGGTGATC

GTGAAAATGATCGCGTGCAGATCTTTGATCTGGAAGGCAATCTGCTGGAAATTTGGACCGGTTTT

GCACCGTATGGTATGGAATTTGATAGCCGTGGTAACCTGTTTGTTGCAGATGGTCGTGCAAATAA

AGTTCTGCAGCTGAATGCAAGCGGTAAAGTTGAAAATAGCTGGGGTAAAACCGGCAAAGAACCG

GGTGAGTATAACCTGCCTCACATGCTGGCAGTCGACGCAGCAGGCAACCTGTTTGTGACCGAAA

TTGGTGGTAAACGTCTGCAGAAACTGCAGCGCAAA
```

Plasmid J encoding protein 10 was obtained by ligating a synthetic XhoI/BamHI fragment encoding the linker and PAL-like region into an pET11a already encoding a Purification tag (SEQ ID NO: 7) and performing the verification steps as described in Example 1. Expression in BL21 (DE3) resulted in a protein with an expected molecular mass as judged by LC-MS analysis as described in Example 1 and the expression levels and high solubility characteristics of protein 10 were similar to the *Erythrobacter* variants described in Example 1.

Cation exchange capture was performed essentially as described in Example 1. Following the capture on SP Sepharose FF a major peak was observed at a NaCl conc. of ~0.25 M and based on SDS-PAGE analysis. The capture was efficient, with very low amounts of protein detected in the flow through and the purity of the protein from the main peak was estimated to be ~80%.

Fractions containing eluted enzymes were pooled together and up-concentrated and desalted in a buffer containing 50 mM Tris pH 7.5 using Vivaspin MWCO 10,000 Da columns (Vivaspin) and stored at 20° C. until used.

Example 5

Enzyme Activity Assay for Estimating Conversion of α-Hydroxy Hippuric Acid and Benzamide Enzymatic Reaction:

An enzymatic assay for measuring PAL activity was previously described (Katopodis A G et al: Biochemistry. (1990) 29(26):6115-20), which measures the conversion of α-hydroxy hippuric acid to benzamide. In order to test the PAL-domains ability to convert α-hydroxy hippuric acid to benzamide enzymatic reactions were setup as follows:

Enzyme (described in above examples): ~0.2 mg/ml
α-hydroxy hippuric acid (Sigma): 1 mg/ml
$Zn_2SO_4$: 1 mM
Buffer: MES pH 5.5 or Tris pH 7.5: 100 mM The reaction was incubated for 3 hours at 37° C. and the peaks corresponding to α-hydroxy hippuric acid and benzamide was evaluated following separation using UPLC (Ultra Performance Liquid Chromatography) instead of HPLC described previously.

UPLC Separation Conditions

Waters ACQ-TUV Instrument setup:

Column: UPLC BEH300 C18, 1.7 mm, 2.1×150 mm column from Waters (part #186003687)
Solvent A: 0.1% TFA,
Solvent B: 90% MeCN, 0.1% TFA (v/v)

| Gradient table | | | | | |
| --- | --- | --- | --- | --- | --- |
| Step | Time (min) | Flow rate | % A | % B | Curve |
| 1 | Initial | 0.3 | 95 | 5 | |
| 2 | 5 | 0.3 | 85 | 15 | 6 |
| 3 | 5.50 | 0.3 | 10 | 90 | 6 |
| 4 | 6.50 | 0.3 | 10 | 90 | 6 |
| 5 | 7 | 0.3 | 95 | 5 | 6 |
| 6 | 8 | 0.3 | 95 | 55 | 6 |
| 7 | 20 | 0.020 | 95 | 5 | 11 |

UPLC analysis of the levels of synthetic α-hydroxy-hippuric acid and benzamide representing α-hydroxyglycine and α-amide, respectively following incubation with enzymes indicates whether the enzymes can convert a α-hydroxyglycine to α-amide group. An increase in the benazamide peak area compared to the α-hydroxy hippuric acid peak area compared to a control without enzyme verifies that the enzyme has the PAL activity. Based on the semiquantitative analysis of areas below the peaks representing the α-hydroxyhippuric acid and benzamide it was verified that all four enzymes (protein 3, protein 8, protein 9 and protein 10) can catalyze the transformation of α-hydroxyglycine to α-amide. PAL-like domains from *Erythrobacter* and *Exiguobacterium* (protein 3 and protein 8) are predominantly active at higher pH (pH 7.5), whereas PAL-like domains from *Chthoniobacter* and *Planctomyces* were significantly more active at lower pH (pH 5.5) indicating differences in pH optimum for the enzymes (as exemplified for *Erythrobacter* and *Chthoniobacter* PAL-like domains shown in FIG. 5). Analysis of mature and TAP tagged variants of *Erythrobacter* PAL-like protein (protein 3) and *Exiguobacterium* PAL-like protein (protein 8) shows that the TAP tagged PAL-like proteins are functional enzymes with activities comparable to the mature enzymes without an N-terminal fusion partner (SEQ ID NO: 7) (FIG. 5).

Example 6

Test of Activity of PAL-Like Domains on Tap Tagged C-Terminal Gly Extended Amylin Analog Substrate Co-Treated with Rat PHM In order to test whether the bacterial PAL-like domains are suitable for α-amidation of C-terminally Gly-extended recombinant peptides, enzymatic reactions were setup with bacterial PAL-like domains and a well-known PHM domain from rat (*Rattus norvegicus*). The rat PHM domain (comprising the amino acid sequence from 36 to 497 of the 976 aa full-length rat PAM sequence) was used to facilitate the formation of a C-terminal α-hydroxyglycine was purified following transient recombinant expression in HEK293 cells essentially as described in Husten E J et al. (1993) J. Biol. Chem.; 268(13):9709-17.

A relevant model peptide substrate for the enzymes were designed, which comprised a sequence as depicted in SEQ ID NO:17. The peptide consists of an N-terminal TAP tag comprising ribosomal protein L27 from *T. maritima*, an intervening linker with a Enterokinase site and an human amylin analog with a C-terminal Gly extension (containing the following amino acid substitutions: Val17His, Ala25Pro, Ser28Pro and Ser29Pro). A gene fragment comprising this sequence was codon optimized for expression in *E. coli* and ligated into a pET11a vector and expressed at 30° C. for 3 hours in BL21 (DE3). Purification was done using a SP Sepharose FF column with the buffers and settings essentially as described in Example 1. Fractions were pooled an upconc. in a buffer containing 100 mM Tris pH 7.5 to a conc. of 0.3 mg/ml.

The model peptide was incubated with the PAL-like domains and other relevant components as described below.

5 μL rat PHM-His (0.15 mg/ml)
5 μL PAL-like domain (protein 3 (0.4 mg/ml) or protein 10 (0.6 mg/ml))
10 μL 100 mM Tris pH 7.5
10 mM Ascorbic acid
10mM $ZnSO_4$
10mM $CuSO_4$
30 μg/ml Catalase
30 μL TAP-tagged Amylin Analog ((V17H)(0.3 mg/ml)

Samples were incubated at 37° C. and the enzymatic reaction was stopped with 3 μL 100% acetic acid and analyzed after 1 h, 2 h and 4 h and 5 h by LC-MS on Poroshell C8

SB300 1 mm×7.5 mm reverse phase columns by LC-MSD-TOF as described in Example 1.

The predicted average isotopic masses for the model protein SEQ ID NO 17 precusor was calculated (the initiator methionine is removed by *E. coli* methionine aminopeptidase due to alanine in second position of SEQ ID NO: 17):

Precursor form (containing a C-terminal Gly residue): 13934.66 Da

The intermediate form (comprising a C-terminal α-hydroxyglycine): 13951 Da

C-terminally alpha amidated form: 13876.62 Da

Following treatment of the model peptide with rat PHM for 2 hours alone it was observed, that the vast majority of the model peptide was on the intermediate form comprising a α-hydroxyglycine in the C-terminal as determined by LC-MS analysis (FIG. 6B). A small amount of alpha amidated product also appeared due to spontaneous conversion as observed for synthetic benzoul derivative substrates in Example 5. However, upon addition of PAL-like domain a significant conversion into the alpha amidated protein was observed, but with differences in the specific activity of the two tested enzymes. With protein 10 total conversion of the precursor was observed already after 1 h-2 h incubation using the described incubation conditions (FIG. 6C). In comparison near complete conversion to the alpha amidated form required 5 hours incubation with the protein 3 enzyme (FIGS. 6D and 6F). Altogether these data shows, that the bacterial PAL-like domains can catalyse the conversion of a recombinant C-terminal Gly-extended protein precursor to a fully C-terminally alpha amidated protein in the presence of an enzyme with PHM activity.

Example 7

Test of Activity of PAL-Like Domains on TAP Tagged C-Terminal Gly Extended Amylin Analog (Pramlintide) Substrate Bacterial PAL like domains were tested on the C-terminal Gly-extended peptide analog of human amylin referred to as Pramlintide (containing the following amino acid substitutions: Ala25Pro, Ser28Pro and Ser29Pro) (SEQ ID NO: 25), which was obtained by solid-phase peptide synthesis and lyophilized following purification. The theoretical average isotopic masses of the three forms of Pramlintide are:
Gly extended Pramlintide: 4007.5 Da
Alpha hydroxyglycine extended Pramlintide: 4023.5 Da
Alpha amidated Pramlintide 3949.4 Da
SEQ ID NO: 25: KCNTATCATQRLANFLVHSSNNFG-PILPPTNVGSNTYG
Preparation of Pramlintide C-Terminal Extended with Alpha-Hydroxy Glycine Using Rat PHM Synthetic C-terminally Gly-extended Pramlintide was dissolved in 100 mM Tris pH7.5 to a final concentration 1 mg/ml. The solution was incubated with rat PHM domain (used in Example 6) using an enzyme to substrate ratio of 1:20 (w/w) as described in the below table:

| PHM | Pramlintide | CuSO4(uM) | Catalase ug/ml | Ascorbic acid (mM) |
| --- | --- | --- | --- | --- |
| 0.2 mg | 4 mg | 5 | 20 | 10 |

The reaction was carried out for 37° C. for 2 h and then stopped by adding TFA to a final concentration 0.1%. After the reaction, 20 ul sample from the reaction mixture were analyzed by LC-MS (essentially as described in example 6, except that a C18 Reversed Phase column was used) and it was verified that the intermediate alpha-hydroxyglycine form of Pramlintide was obtained.

The rat PHM treated sample was purified by Reversed Phase C18 preparative HPLC using a Agilent Zorbac C18 Extend column on a Agilent 1100 HPLC instrument with the conditions and acetonitrile gradients listed in the below table.

| Buffer A: 95% H2O 5% ACN 0.1% TFA | | |
| --- | --- | --- |
| Buffer B: 70% ACN 20% Isopropanol 0.1% TFA. | | |
| Time (min) | B % | Flowrate (ml/min) |
| 0 | 0 | 0.3 |
| 4 | 0 | 0.3 |
| 4.5 | 10 | 0.3 |
| 15 | 100 | 0.3 |
| 16 | 100 | 0.3 |
| 17 | 10 | 0.3 |
| 20 | 10 | 0.3 |

The C-terminal alpha-hydroxyglycine extended Pramlintide intermediate was purified. Following collection of the peptide and pooling of relevant fractions the sample was dried down using a Therm DNA120 Speed Vac and the peptide re-dissolved in 1 mL 100 mM Tris pH 7.5 buffer. The final amount of alpha-hydroxy glycine extended Pramlintide was measured by UV280 absorption and the concentration was adjusted to 0.5 mg/ml peptide.

Estimating the Activity of Bacterial PAL-Like Domain on Pramlintide Alpha-Hydroxyglycine Intermediate Peptide In order to test the activity of the PAL-like domains (SEQ ID NO: 1, 2, 3 and 4), the following reactions in 100 mM Tris pH 7.5 buffer was setup using the prepared alpha-hydroxylated SEQ ID NO:25 as peptide substrate:

| PAL-like domain (ug) | Pramlintide_Gly(OH) (ug and mg/ml) | ZnSO$_4$ (uM) | Enzyme to substrate ratio (w/w) |
| --- | --- | --- | --- |
| 2 | 50 ug 0.5 mg/ml | 0.5 | 25 |
| 1 | 50 ug 0.5 mg/ml | 0.5 | 50 |
| 0.5 | 50 ug 0.5 mg/ml | 0.5 | 100 |
| 0.1 | 25 0.5 mg/ml | 0.5 | 250 |
| 0.05 | 25 0.5 mg/ml | 0.5 | 500 |
| 0.02 | 25 0.5 mg/ml | 0.5 | 1250 |

The reaction mixtures were incubated at 37° C. for 1 h and stopped by addition of TFA to 0.1% prior to LC-MS analysis on a then analysis the sample by LC/MS.

Two major peaks were observed on the deconvoluted spectra representing the alphahydroxyglycine intermediate and fully alpha amidated Pramlintide.

All four bacterial PAL like domains could convert the alphahydroxy Glycine intermediate of Pramlintide to alpha amidated Pramlintide. *Erythrobacter* (FIG. 7A) and *Planctomyces* (FIG. 7B) PAL like domain were significantly more efficient in catalyzing the reaction, as they could almost completely convert the peptide substrate to fully alpha-amidated peptide using a enzyme to substrate ratio of 1:100 under the tested condition. *Exiguobacterium* (FIG. 7C) and *Chthoniobacter* (FIG. 7D) PAL were not able to convert all the peptide substrate to alpha amidated peptide, but as observed for the relative peak intensities of the 4023 (alpha hydroxyglycine extended Pramlintide) and 3948 Da (Alpha amidated Pramlintide) it can be concluded, that they catalyze the reaction, but a slower rate needing higher concentrations of enzyme. The difference between the two sets of PAL like domains may be caused by the observed difference in pH preference described in example 5.

The results provides evidence that all four bacterial PAL-like domains has Peptidyl hydroxyglycine alpha amidating lyase activity and can catalyze the same reaction as previously described for eukaryotic PAL on a typical peptide substrate, which needs to be alpha amidated to obtain biological activity.

ASSAYS

Assay (I)

Evaluation of Activity

The activity of the PAL enzyme may be measured as described in Example 5. The activity of the PAL enzyme can be demonstrated by measuring the conversion of α-hydroxyhippuric acid to benzamide as described in Katopodis A G et al, Biochemistry. 1990, 29(26):6115-6120. Instead of using the HPLC method as described it is of advantage to use adapted UPLC method. The conditions for the UPLC method is describe in example 5.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A method for producing an α-amidated peptide comprising:
   (i) allowing a target peptide with a C-terminal glycine residue to react with both a peptidylglycine alpha-hydroxylating monooxygenase (PHM) and a polypeptide consisting of amino acids 2-306 of SEQ ID NO: 1, amino acids 3-336 of SEQ ID NO: 2, amino acids 3-305 of SEQ ID NO: 3, or amino acids 3-279 of SEQ ID NO: 4, wherein said polypeptide has peptidyl-α-hydroxyglycine alpha-amidating lyase (PAL) activity under conditions suitable for enzymatic activity, and optionally further comprises 1-30 substitution(s) or deletion(s), and wherein the reaction with said PHM and said polypeptide on said target peptide is performed either in two separate steps or simultaneously; and
   (ii) recovering the C-terminally α-amidated peptide.

2. The method of claim 1, wherein the polypeptide has been expressed in a recombinant *E. coli*.

3. The method of claim 1, wherein the polypeptide from a prokaryotic organism has an amino acid sequence comprising 0, 1 or 2 cysteine (Cys) residues.

4. The method of claim 1, wherein the polypeptide is in a catalytically active form and does not require a step of refolding for obtaining catalytic activity.

5. The method of claim 1, wherein the target peptide is selected from the group consisting of amylin, Neuropeptide Y (NPY), Peptide YY (PYY), PYY-3-36, Pancreatic polypeptide (PP), Glucagon like peptide (GLP-1), gastrin, calcitonin, calcitonin related peptide (CGRP), gastrin releasing peptide, vasopressin, oxytocin, neurokinin A, secretin, pancreastatin, pro-opiomelanocortin (POMC), alpha-melanocyte-stimulating hormone (alpha MSH), gamma-melanocyte-stimulating hormone (gamma 1MSH), and amidated hinge peptide (HP-N) or functional analogs thereof.

* * * * *

UNITED STATES PATENT AND TRADEMARK OFFICE
CERTIFICATE OF CORRECTION

| | | |
|---|---|---|
| PATENT NO. | : 9,096,843 B2 | Page 1 of 1 |
| APPLICATION NO. | : 13/513049 | |
| DATED | : August 4, 2015 | |
| INVENTOR(S) | : Allan C. Shaw | |

It is certified that error appears in the above-identified patent and that said Letters Patent is hereby corrected as shown below:

Claims

At column 77, claim number 1, line number 12, please amend to "...suitable for enzymatic activity, and..."

Signed and Sealed this
Twenty-second Day of December, 2015

Michelle K. Lee
*Director of the United States Patent and Trademark Office*